(12) United States Patent
Chorghade et al.

(10) Patent No.: US 6,306,895 B1
(45) Date of Patent: Oct. 23, 2001

(54) SUBSTITUTED OXYGEN ALICYCLIC COMPOUNDS, INCLUDING METHODS FOR SYNTHESIS THEREOF

(75) Inventors: Mukund Shankar Chorghade, Natick, MA (US); Mukund Keshao Gurjar, Pune; Palakodety Radha Krishna, Hyderabad, both of (IN); Sista Venkata Sai Lalitha, Sunnyvale, CA (US); Kashinath Sadalapure, Gulbarga (IN); Susanta Sekhar Adhikari, West Bengal (IN); Andappan Murugaiah Subbaiah Murugaiah, Tamilnadu (IN); Batchu Venkateswara Rao, Nellore (IN); Levadala Murali Krishna, Hyderabad (IN); Sunil Vyankatesh Mhaskar, Natick, MA (US); Gangavaram Vasantha Madhava Sharma, Hyderabad (IN); Tangallapally Rajendra Prasad, Warangal (IN); Punna Sreenivas, Nalgonda (IN); Vavilala Goverdhan Reddy, Mahabubnagar (IN); Aminul Islam, Hyderabad (IN); Alla Venkata Rama Rao, Hyderabad (IN); Hymavathi Lanka, Hyderabad (IN); Bethi Sridhar Reddy, Hyberabad (IN); Chittineni Hari Prasad, Hyderabad (IN)

(73) Assignee: Millenium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 09/347,113

(22) Filed: Jul. 2, 1999

Related U.S. Application Data
(60) Provisional application No. 60/091,694, filed on Jul. 3, 1998.

(51) Int. Cl.$^7$ .................................................. A01N 43/02
(52) U.S. Cl. .......................................... 514/450; 549/346
(58) Field of Search ............................. 514/450; 549/346

(56) References Cited

U.S. PATENT DOCUMENTS

| | | | |
|---|---|---|---|
| 5,037,853 | 8/1991 | Brooks et al. | 514/595 |
| 5,112,848 | 5/1992 | Brooks et al. | 514/424 |
| 5,169,854 | 12/1992 | Brooks et al. | 514/314 |
| 5,175,183 | 12/1992 | Brooks et al. | 514/438 |
| 5,183,818 | 2/1993 | Brooks et al. | 514/231.5 |
| 5,187,192 | 2/1993 | Brooks et al. | 514/445 |
| 5,288,751 | 2/1994 | Brooks et al. | 514/438 |
| 5,326,787 | 7/1994 | Brooks et al. | 514/507 |
| 5,358,938 | 10/1994 | Cai et al. | 514/231.5 |
| 5,434,151 | 7/1995 | Cai et al. | 514/231.5 |
| 5,463,083 | 10/1995 | Biftu et al. | 549/71 |
| 5,530,141 | 6/1996 | Shen et al. | 549/39 |
| 5,543,531 | 8/1996 | Funfschilling et al. | 549/62 |
| 5,639,782 | 6/1997 | Shen et al. | 574/440 |
| 5,681,966 | 10/1997 | Cai et al. | 549/65 |
| 5,703,093 | 12/1997 | Cai et al. | 514/473 |
| 5,741,809 | 4/1998 | Biftu et al. | 514/428 |
| 5,750,565 | 5/1998 | Cai et al. | 514/473 |
| 5,756,768 | 5/1998 | Kanou et al. | 549/66 |
| 5,780,503 | 7/1998 | Biftu et al. | 514/471 |
| 5,792,776 | 8/1998 | Biftu et al. | 514/303 |
| 5,856,323 | 1/1999 | Cai et al. | 514/231.5 |

FOREIGN PATENT DOCUMENTS

| | | |
|---|---|---|
| WO 92/15294 | 9/1992 | (WO) . |
| WO 94/01430 | 1/1994 | (WO) . |
| WO 94/06790 | 3/1994 | (WO) . |
| WO 95/18610 | 7/1995 | (WO) . |
| WO 96/00212 | 1/1996 | (WO) . |

*Primary Examiner*—Amelia Owens
(74) *Attorney, Agent, or Firm*—Peter F. Corless; Christine C. O'Day; Edwards & Angell, LLP

(57) ABSTRACT

The invention provides new methods for preparation of cyclic oxygen compounds, including 2,5-disubstituted tetahydrofurans, 2,6-disubstituted tetrahydropyrans, 2,7-disubstituted oxepanes and 2,8-oxocanes. The invention also provides new cyclic oxygen compounds and pharmaceutical compositions and therapeutic methods that comprise such compounds.

76 Claims, No Drawings

SUBSTITUTED OXYGEN ALICYCLIC COMPOUNDS, INCLUDING METHODS FOR SYNTHESIS THEREOF

The present application claims the benefit of U.S. provisional application No. 60/091,694, filed Jul. 3, 1998, which is incorporated herein by reference in its entirety.

BACKGROUND

1. Field of the Invention

The present invention provides new methods for preparation of various oxygen ring compounds (oxygen as an alicyclic ring member) including 2,5-disubstituted tetrahydrofurans, 2,6-disubstituted tetrahydropyrans, 2,7-disubstituted oxepanes and 2,8-oxocanes. The invention firer provides novel compounds and pharmaceutical compositions and therapeutic methods that comprise such compounds.

2. Background

Leukotrienes are recognized potent local mediators, playing a significant role in inflammatory and allegeric responses, including arthritis, asthma, psoriasis and thrombotic disease. Leukotrienes are produced by the oxidation of arachidonic acid by lipoxygenase. More particularly, arachidonic acid is oxidized by 5-lipooxygenase to the hydroperoxide 5-hydroperoxy-eicosatetraenoic acid (5-HPETE), that is converted to leukotriene $A_4$, that in tun can be converted to leukotriene $B_4$, $C_4$, or $D_4$. The slow-reacting substance of anaphylaxis is now known to be a mixture of leukotrienes $C_4$, $D_4$ and $E_4$, all of which are potent bronchoconstrictors.

Efforts have been made to identify receptor antagonists or inhibitors of leukotriene biosynthesis, to prevent or minimize pathogenic inflammatory responses mediated by leukotrienes.

For example, European Patent Application Nos. 901171171.0 and 901170171.0 report indole, benzofuran, and benzothiophene lipoxygenase inhibiting compounds.

Various 2,5-disubstituted tetrahydrofurans have exhibited significant biological activity, including as lipoxygenase inhibitors. See U.S. Pat. Nos. 5,703,093; 5,681,966; 5,648,486; 5,434,151; and 5,358,938.

While such compounds are highly useful therapeutic agents, current methods for synthesis of least some of the compounds require lengthy routes, and reagents and protocols that are less preferred in larger scale operations, such as to produce kilogram quantities.

It thus would be desirable to have improved methods to substituted tetrahydrofurans and other cyclic oxygen compounds, particularly new syntheses that facilitate larger scale production of such compounds.

SUMMARY OF THE INVENTION

We have now found new methods for preparation of cyclic oxygen compounds, including 2,5-disubstituted tetrahydrofurans, 2,6-disubstituted tetrahydropyrans, 2,7-disubstituted oxepanes and 2,8-oxocanes. These methods utilize reagents and synthetic protocols that facilitate large scale manufacture, and provide increased yields relative to prior approaches.

The methods of the invention are suitable for preparation of a variety of cyclic oxygen-containing compounds (i.e., alicyclic compounds having an oxygen ring member), including compounds of the following Formula I:

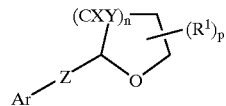

wherein Ar is optionally substituted carbocyclic aryl or optionally substituted heteroaryl;

each $R^1$, X and Y is independently hydrogen or a non-hydrogen substituent such as halogen, hydroxyl, optionally substituted alkyl preferably having from 1 to about 20 carbon atoms, optionally substituted alkenyl preferably having from 2 to about 20 carbon atoms, optionally substituted alkynyl preferably having from 2 to about 20 carbon atoms, optionally substituted alkoxy preferably having from 1 to about 20 carbon atoms, optionally substituted alkylthio preferably having from 1 to about 20 carbon atoms, optionally substituted alkylsulfinyl preferably having from 1 to about 20 carbon atoms, optionally substituted alkylsulfonyl preferably having from 1 to about 20 carbon atoms, optionally substituted aminoalkyl preferably having from 1 to about 20 carbon atoms, optionally substituted alkanoyl preferably having from 1 to about 20 carbon atoms, optionally substituted carbocyclic aryl having at least about 6 ring carbons, or substituted or unsubstituted aralkyl having at least about 6 ring carbons, and the like;

Z is a chemical bond, optionally substituted alkylene, optionally substituted alkenylene, optionally substituted alkynylene, optionally substituted heteroalkylene, optionally substituted heteroalkenylene, optionally substituted heteroalkenylene, or a hetero atom such as O, S, S(O), S(O)$_2$, or NR$^1$ wherein R$^1$ is the same as defined immediately above;

n is an integer from 1 to 11, and preferably is 1 to 9, more preferably 1 to 7;

p is an integer from 0 (where the α and β ring positions are fully hydrogen-substituted) to 4; and pharmaceutically acceptable salts thereof.

The methods of the invention are particularly suitable for synthesis of substituted tetrahydrofurans, including compounds of the following Formula II:

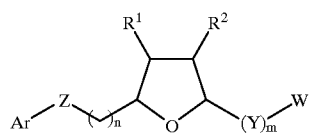

wherein Ar is optionally substituted aryl or heteroaryl;

m is 0 or 1; n is 1–6;

W is —AN(OM)C(O)N($R^3$)$R^3$, —N(OM)C(O)N($R^3$)$R^4$, —AN($R^3$)C(O)N(OM)$R^4$, —N($R^3$)C(O)N(OM)$R^4$, —AN(OM)C(O)$R^4$, —N(OM)C(O)$R^4$, —AC(O)N(OM)$R^4$, —C(O)N(OM)$R^4$, or —C(O)NHA; and A is lower alkyl, lower alkenyl, lower alkynyl, alkylaryl or arylalkyl, wherein one or more carbons optionally can be replaced by N, O or S, however —Y—A—, —A—, or —AW— should not include two adjacent heteroatoms;

M is hydrogen, a pharmaceutically acceptable cation or a metabolically cleavable leaving group;

X and Y are each independently O, S, S(O), S(O)$_2$, NR$^3$ or CHR$^5$;

Z is O, S, S(O), S(O)$_2$, or NR$^3$;

R$^1$ and R$^2$ are each independently hydrogen, lower alkyl, C$_{3-8}$ cycloalkyl, halolower alkyl, halo or —COOH;

R$^3$ and R$^4$ are independently hydrogen, alkyl, alkenyl, alkynyl, aryl, arylalkyl, C$_{1-6}$alkoxy-C$_{1-10}$alkyl, C$_{1-6}$ alkylthio-C$_{1-10}$ alkyl, heteroaryl, or heteroarylalkyl;

R$^5$ is hydrogen, lower alkyl, lower alkenyl, lower alkynyl, arylalkyl, alkaryl, —AN(OM)C(O)N(R$^3$)R$^3$, —AN(R$^3$)C(O)N(OM)R$^4$, —AN(OM)C(O)R$^4$, —AC(O)N(OM)R$^4$, —AS(O)$_x$R$^3$, —AS(O)$_x$CH$_2$C(O)R$^3$, —AS(O)$_x$CH$_2$CH(OH)R$^3$, or —AC(O)NHR$^3$, wherein x is 0–2; and pharmaceutically acceptable of such compounds.

Compounds of Formula II have been disclosed in U.S. Pat. No. 5,703,093. As disclosed in that patent, preferred compounds of Formula II include compounds where Ar is substituted by halo (including but not limited to fluoro), lower alkoxy (including methoxy), lower aryloxy (including phenoxy), W (as defined above in Formula II), cyano, or R$^3$ (as defined above in Formula II). Those substituents are also preferred Ar group substituents for compounds of other formulae disclosed herein. Specifically suitable Ar groups for the above Formula II as well as the other formulae disclosed herein include phenyl, trimethoxyphenyl, dimethoxyphenyl, fluorophenyl (specifically 4-fluorophenyl), difluorophenyl, pyridyl, dimethoxypyridyl, quinolinyl, furyl, imidazolyl, and thienyl. Additionally, in Formula II as well as other formulae disclosed herein, W suitably is lower alkyl, such as a branched alkyl group, e.g. —(CH2)$_n$C(alkyl)H—, wherein n is 1–5, and specifically —(CH$_2$)$_2$C(CH$_3$)H—, or lower alkynyl such as of the formula —C≡C—CH(alkyl)-, including —C≡C—CH(CH$_3$)—.

In particularly preferred aspect, methods of the invention are employed to synthesis the following compound 1, 2S,5S-trans-2-(4-fluorophenoxymethyl)-5-(4-N-hydroxyureidyl-1-butynyl)-tetrahydrofuran:

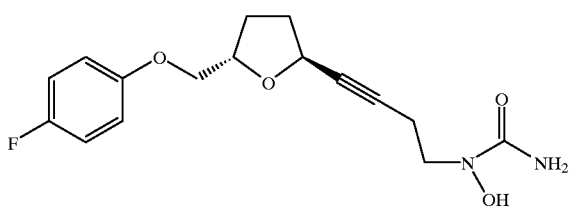

1

It has been found that biological activity, particularly 5-lipoxygenase activity, can vary among optically active isomers of compounds of the invention, and therefore a single optical isomer of a compound may be preferred. Accordingly, the synthetic methods of the invention include preparation of enantiomerically enriched compounds of the invention.

In a first preferred aspect, substituted tethydrofuran compounds are provided by reacting a hydroxy substituted aryl compound with an epoxide having a reactive carbon, e.g. a glycidyl compound substituted at the C3 position with an electron-withdrawing group such as halo (e.g. epichlorohydin, epibrommhydrin), mesyl or tosyl (glycidyl mesylate and glycidyl tosylate), etc., to form an epoxyarylether or epoxyoarylether in the presence of base and preferably at or above about 0° C. (As used herein, the term "aryl" refers to both carbocyclic aryl and heteroaromatic or heteroaryl groups, which terms are further discussed below). That epoxyether is then reacted with an active methylene compound to form a lactone, preferably a γ-lactone. The active methylene compound can be a variety of agents. Diethyl and dimethyl malonate are generally preferred, which provide an ethyl or methyl ester as a lactone ring substituent. That ester group is then removed (e.g. via hydrolysis and decarboxylation), and the lactone suitably reduced to a hydroxy-substituted tetrahydrofuran, particularly a hydroxytetrahydrofuran-aryl ether.

The hydroxy tetrahydrofuran can be further functionalized as desired, particularly by activating the hydroxyl substituent of the hydroxytetrahydrofuran-aryl ether followed by substitution of the corresponding position of the tetrahydrofuran ring such as by a 1-alkyne reagent. Also, rather than directly activating the hydroxyl moiety, that group can be replaced with a halide, and the halide-substituted tetrahydrofuran reacted with a benzylsulfonic acid reagent.

It also has been found that methods of the invention enable such substitution of the tetrahydrofuran to proceed with extremely high stereoselectivity, e.g. at least greater than about 60 mole percent of one stereoisomer than the other, more typcially greater than about 70 or 75 mole percent of one stereoisomer than the other isomer. Recrystallization of such an enantiomerically enriched mixture has provided very high optical purities, e.g. about 95 mole %, 97 mole % or even 99 mole % or more of the single stereoisomer.

In another aspect, methods are provided that involve cleavage of a bis-compound to provide high yields of tetrahydrofuran compounds, including compounds of Formula II above. These methods preferably involve condensation of mannitol with am alkanoyl compound such as formaldehyde to form a trialkylene mannitol such as a tri(C1–10alkylene) mannitol such as trimethylene mannitol where formaldehyde is employed, which is then cleaved to form 2,5,-O-methylene-mannitol, which has two primary hydroxyl groups and two secondary hydroxyl groups. The primary hydroxyl groups are protected (e.g. as esters) and the secondary hydroxyl groups then are suitably cyclized, e.g. with a trialkylorthoformate reagent, to provide a cyclic ether. The protected primary alcohols are then converted to aryl ethers, followed by cleavage of the cyclic ether to provide again the secondary hydroxyl groups. The mannitol compound then undergoes oxidative cleavage to provide the corresponding alicyclic dialdehyde, which aldehyde groups are functionalized to bis-α,β-unsaturated esters. The carbon—carbon double bonds of that compound are suitably saturated, and the bis-compound cleaved and the cleavage products cyclized to provide an aryltetrahydrofuran ether which can be further functionalized as described above.

In yet another aspect of the invention, preparative methods are provided that include multiple reactions that surprisingly proceed as a single step without isolation of intermediates to provide oxygen ring compounds that have varying ring size as desired. These methods are suitable for preparation of oxygen ring compounds having from 5 to 12 or more ring members, and are particularly useful for synthesis of oxygen ring compounds having from 5 to 8 or 9 ring members.

Moreover, it has been surprisingly found that the one step procedure is enantioselective. Hence, if the starting reagent (a 2,3-epoxide) is optically active, the resulting substituted oxygen ring compound also will be optically active. Moreover, the reaction proceeds with stereoselectivity, i.e. full rentention of configuration.

More particularly, in this aspect of the invention the methods include formation, in a single step, of an alkynyl-substituted oxygen ring compound. For preparation of an alkynyl-tetrahydrofuran, a compound is reacted that has at least a six-carbon alkyl or alklyene chain that is activated at the 1- and 6-carbon positions such as by substitution by suitable leaving groups, and 2- and 3-carbon positions of the chain form an epoxide ring. The leaving groups of the 1- and 6-positions may be e.g. halo, such as chloro or bromo, or an ester, such as an alkyl or aryl sulfonic ester. Preferably, the 1-position is halo-substituted, particularly bromo-, iodo- or chloro-substituted, and the 6-position is substituted by an ester such as by a benzylsulfonyl group. That compound is reacted with molar excess of a strong base such as an alkyllithium reagent that affords an alkynyl-substituted tetrahydrofuran in a single step.

Larger ring alkynyl-substituted compounds are readily provided through corresponding chain homologation of the epoxy reagent, i.e. by interposing additional "spacing" or alkylene chain members between the reagent's activated positions.

Thus, for example, to prepare an alkynyl-substituted tetrahydopyran, a reagent is employed that has at least a seven-carbon alkyl or alkylene chain that is activated at the 1- and 7-carbon positions e.g. by substitution by suitable leaving groups (such as those mentioned above), and the 2- and 3-positions of the chain form an epoxide ring. That compound is reacted with base to provide an alkynyl-substituted tetrahydropyran.

Similarly, to prepare an alkynyl-substituted oxepane, a reagent is employed that has at least a seven-carbon alkyl or alkylene chain activated (particularly by leaving groups) at the 1- and 8-carbon positions, and the 2- and 3-position of the chain form an epoxide ring. To prepare an alkynyl-substituted oxocane compound, a reagent is employed that has at least eight-carbon alkyl of alkylene chain activated at the 1- and 9-carbon positions, with the 2- and 3-positions of the chain forming an epoxide ring. Treatment of those respective reagents with appropriate base provides alkynyl-substituted oxepane and oxocane compounds.

In another aspect of the invention, a chiral synthon is preferably employed such as glyceraldehyde, mannitol, ascorbic acid, and the like, that can provide stereoselective routes to desired compounds of the invention. This approach includes formation of a substituted dioxolane, typically a 1,3-dioxolane particularly (2,2-dimethyl)-1,3-dioxolane), which preferably is optically active. A side chain of the dioxolane, preferably at the 4-position, is suitably extended e.g. by one or more Wittig reactions, typically one, two or more Wittig reactions that provide α,β-unsaturated moieties such as an α,β-unsaturated $C_{1-6}$alkyl ester. Such an α,β-unsaturated provided then can be epoxidized, preferably by asymmetric oxidation of the conjugated alkene to provide an optically active epoxide, which then participates in an elimination reaction to yield a propargyl alcohol as the dioxolane ring substituent. The dioxolane ring then can be opened, typically in the presence of acid and the acyclic intermediate cyclized to provide an optically active oxygen alicyclic compound. See Scheme XV below and the discussion related thereto below. The substituted alicyclic compound can be further functionalized as desired. For instance, the primary hydroxy of the alkylhydroxy substituent of the cyclic compound can be esterified (e.g., sulfonate such as a tosylate) and the activated methyl reacted to provide an aryl substituent, e.g. optionally substituted phenyl substituent. The alkynyl substituent can be extended to provided the hydroxy urea as discussed herein.

In yet a further aspect of the invention, an alkyne-substituted tetrahydrofuran is prepared directly (e.g., without a dioxolane intermediate) from an acyclic keto alkyne compound. More specifically, a keto alkenyl reagent with terminal alkenyl group is suitably employed, e.g. —$CH_2$=$CH(CH_2)_nC$(=O)C≡CR where n is an integer of 2 to 6, preferably 2 to 5, and R is suitably $C_{1-6}$ alkyl and the like. The terminal alkene is then epoxidized, e.g. by ozonolysis or other suitable oxidant. The epoxidized keto alkyne then can be cyclized, e.g. in the presence of boron methyl sulfide and the resulting oxygen alicyclic compound functionalized as desired.

Further provided are new routes to substituted hydroxy ureas. In preferred aspects, these routes include reaction of a protected hydroxyurea (e.g., a compound of the formula $NH_2C(O)NHOR$, where R is a hydroxy protecting group such as para-methoxybenzyl-) with a substituted alcohol in the presence of suitable dehydrating agent(s) to provide an amino ester, which is treated with ammonia and a Lewis acid to provide a hydroxy urea.

As mentioned above, compounds produced by the methods of the invention are useful as pharmaceutical agents, particularly to treat disorders or diseases mediated by 5-lipoxygenase such as immune, allegeric and cardiovascular disorders and diseases, e.g. general inflammation, hypertension, skeletal-muscular disorders, osteoarthritis, gout, asthma, lung edema, adult respiratory distress syndrome, pain, aggregation of platelets, shock, shock, rheumatoid arthritis, psoriatic arthritis, psoriasis, autoimmune uveitis, allergic encephalomyelitis, systemic lupus erythematosis, acute necrotizing hemmorrhagic encephalopathy, idiopathic thrombocytopenia, polychondritis, chronic active hepatitis, idiopathic sprue, Crohn's disease, Graves ophthalmopathy, primary biliary cirrhosis, uveitis posterior, interstitial lung fibrosis, allergic asthma and inappropriate allergic responses to environmental stimuli.

In other aspects, the invention provides new compounds as well as pharmaceutical compositions that comprise one or more of such compounds preferably with a pharmaceutically acceptable carrier. More particularly, the invention in a composition aspect includes compounds of Formula I above, where n is 2 or greater (i.e. compounds with alicyclic oxygen rings that have 6 or more ring members), which includes compounds of Formulae III, IIIa, IV, IVa, V, Va, as those formulae are defined below. The invention further provides methods for treatment and/or prophylaxis of various disorders and diseases including those disclosed above such as immune, allegeric and cardiovascular disorders and diseases, the methods in general comprising administering an effective amount of one or more compounds of Formula I above, where n is 2 or greater, to a subject, such as a mammal particularly a primate such as a human, that is suffering from or susceptible to such a disorder or disease.

Compounds produced by the methods of the invention are useful as synthetic intermediates to prepare other compounds that will be useful for therapeutic applications. Other aspects of the invention are disclosed infra.

DETAILED DESCRIPTION OF THE INVENTION

As discussed above, the invention provides methods that are particularly suitable for synthesis of compounds of the following Formula I:

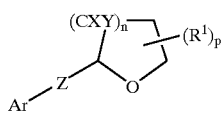

I wherein Ar, Z, X, Y, $R^1$, n and p are as defined above.

As discussed above, in addition to the above-discussed substituted tetrahydrofurans, methods of the invention also provide oxygen ring compounds having 6 or more ring members.

More particularly, preferred compounds produced by the methods of the invention include substituted tetrahydropyrans, including substituted tetrahydropyrans of the following Formula III:

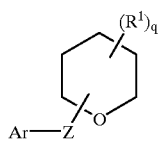

III wherein Ar, Z and $R^1$ are each the same as defined above for Formula I, and q is an integer of from 0 to 9, and preferably q is 1, 2, 3 or 4; and pharmaceutically acceptable salts thereof.

Generally preferred are 2,6-disubstituted tetrahydropyrans, such as compounds of the following Formula IIIa:

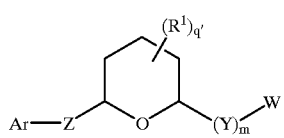

IIIa wherein Ar, Z, Y, W, $R^1$ and m are each the same as defined for Formula II above, and q' is an integer of from 0 to 6, and preferably q' is 0, 1, 2, 3 or 4; and pharmaceutically acceptable salts thereof.

The methods are also particularly useful for preparations of substituted oxepanes including compounds of the following Formula IV:

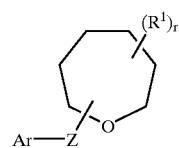

IV wherein Ar, Z and $R^1$ are each the same as defined above for Formula I, and r is an integer of from 0 to 11, and preferably r is 1, 2, 3 or 4; and pharmaceutically acceptable salts thereof.

Generally preferred are 2,7-disubstituted oxepanes, such as compounds of the following Formula IVa;

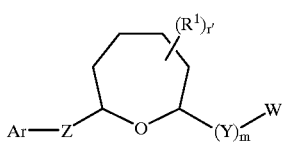

IVa wherein Ar, Z, Y, W, $R^1$ and m are each the same as defined for Formula II above, and r' is an integer of from 0 to 10, and preferably r' is 0, 1, 2, 3 or 4; and pharmaceutically acceptable salts thereof.

Still further, methods of the invention can be especially useful for synthesis of substituted oxocanes, such as compounds of the following Formula V:

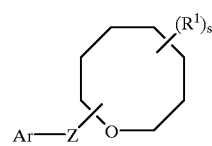

V wherein Ar, Z and $R^1$ are each the same as defined above for Formula I, and s is an integer of from 0 to 13, and preferably s is 1, 2, 3 or 4; and pharmaceutically acceptable salts thereof.

Generally preferred are 2,8-disubstituted oxocanes, such as compounds of the following Formula Va;

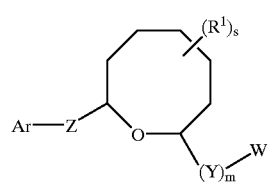

Va wherein Ar, Z, Y, W, $R^1$ and m are each the same as defined for Formula II above, and s' is an integer of from 0 to 10, and preferably s' is 0, 1, 2, 3 or 4; and pharmaceutically acceptable salts thereof.

Preferred compounds of the invention include those having one or more hydroxy and/or alkoxy substituents on the alicyclic ring, typically one, two or three hydroxy and/or alkoxy ring substituents. Hence, in the above formulae I, III, IIIa IV, IVa, V, IVa, each $R^1$ is independently hydroxy or alkoxy and p is one or greater. Typical alkoxy alicyclic ring substituents include $C_{1-8}$alkoxy, more typically $C_{1-6}$alkoxy, still more typically $C_{1-3}$alkoxy compounds. Particularly preferred compounds include those where at least two hydroxy and/or alkoxy groups are substituents on adjacent carbons of the alicyclic ring, e.g. vicinal di-hydroxy compounds and vicinal di-alkoxy compounds.

The term alkyl, as used herein, unless otherwise specified, refers to a saturated straight, branched, or cyclic hydrocarbon and unless otherwise specified is $C_1$ to $C_{10}$, and specifically includes methyl, ethyl, propyl, isopropyl, butyl, isobutyl, t-butyl, pentyl, cyclopentyl, isopentyl, neopentyl, hexyl, isohexyl, cyclohexyl, 3-methylpentyl, 2,2-dimethylbutyl, and 2,3-dimethylbutyl. The alkyl group can be optionally substituted with any appropriate group, including but not limited to $R^3$ or one or more moieties selected from the group consisting of halo, hydroxyl, amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as disclosed in Greene et al., "Protective Groups in Organic Synthesis", John Wiley and Sons, Second Edition, 1991.

The term halo, as used herein, refers to chloro, fluoro, iodo, or bromo.

The term lower alkyl, as used herein, and unless otherwise specified, refers to a $C_1$ to $C_6$ saturated straight, branched, or cyclic (in the case of $C_{5-6}$) hydrocarbon, and specifically includes methyl, ethyl, propyl, isopropyl, butyl, isobutyl, t-butyl, pentyl, cyclopentyl, isopentyl, neopentyl, hexyl, isohexyl, cyclohexyl, 3-methylpentyl, 2,2-dimethylbutyl, and 2,3-dimethylbutyl, optionally substituted as described above for the alkyl groups.

The term alkenyl, as referred to herein, and unless otherwise specified, refers to a straight, branched, or cyclic (in the case of $C_{5-6}$) hydrocarbon of $C_2$ to $C_{10}$ with at least one double bond, optionally substituted as described above.

The term lower alkenyl, as referred to herein, and unless otherwise specified, refers to an alkenyl group of $C_2$ to $C_6$, and specifically includes vinyl and allyl.

The term lower alkylamino refers to an amino group that has one or two lower alkyl substituents.

The term alkynyl, as referred to herein, and unless otherwise specified, refers to a $C_2$ to $C_{10}$ straight or branched hydrocarbon with at least one triple bond, optionally substituted as described above. The term lower alkynyl, as referred to herein, and unless otherwise specified, refers to a $C_2$ to $C_6$ alkynyl group, specifically including acetylenyl, propynyl, and —C≡C—CH(alkyl), including —C≡C—CH(CH$_3$)—.

The term carbocyclic aryl, as used herein, and unless otherwise specified, refers to non-hetero aromatic groups that have 1 to 3 separate or fused rings and 6 to about 18 carbon rings members and may include e.g. phenyl, naphthyl, biphenyl, phenanthracyl, and the like. The carbocyclic aryl group can be optionally substituted with any suitable group, including but not limited to one or moieties selected from the group consisting of halo, hydroxyl, amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene et al., "Protective Groups in Organic Synthesis", John Wiley ad Sons, Second Edition, 1991, and preferably with halo (including but not limited to fluoro), lower alkoxy (including methoxy), lower aryloxy (including phenoxy), W, cyano, or $R^3$.

The term haloalkyl, haloalkenyl, or haloalkynyl refers to alkyl, alkenyl, or alkynyl group in which at least one of the hydrogens in the group has been replaced with a halogen atom.

The term heteroaryl, heterocycle or heteroaromatic, as used herein, refers to an aromatic moiety that includes at least one sulfur, oxygen, or nitrogen in the aromatic ring, which can optionally be substituted as described above for the aryl groups. Non-limiting examples are pyrryl, furyl, pyridyl, 1,2,4-thiadiazolyl, pyrimidyl, thienyl, isothiazolyl, imidazolyl, tetrazolyl, pyrazinyl, pyrimidyl, quinolyl, benzofuran, isoquinolyl, benzothienyl, isobenzofuryl, pyrazolyl, indolyl, purinyl, carbazolyl, benzimidazolyl, and isoxazolyl. Suitable heteroaromatic or heteroaryl groups will have 1 to 3 rings, 3 to 8 ring members in each ring and from 1 to 3 heteroatoms (N, O or S).

The term arylalkyl refers to a carbocyclic aryl group with an alkyl substituent.

The term alkylaryl refers to an alkyl group that has a carbocyclic aryl substituent.

The term organic or inorganic anion refers to an organic or inorganic moiety that carries a negative charge and can be used as the negative portion of a salt.

The term "pharmaceutically acceptable cation" refers to an organic or inorganic moiety that carries a positive charge and that can be administered in association with a pharmaceutical agent, for example, as a counter cation in a salt. Pharmaceutically acceptable cations are known to those of skill in the art, and include but are not limited to sodium, potassium, and quaternary amine.

The term "metabolically cleavable leaving group" refers to a moiety that can cleaved in vivo from the molecule to which it is attached, and includes but it not limited to an organic or inorganic anion, a pharmaceutically acceptable cation, acryl (for example (alkyl)C(O), including acetyl, propionyl, and butyryl), alkyl, phosphate, sulfate and sulfonate.

Alkylene and heteroalkylene groups typically will have about 1 to about 8 atoms in the chain, more typically 1 to about 6 atoms in the linkage. Alkenylene, heteroalkenylene, alkenylene and heteroalkenylene groups typically will have about 2 to about 8 atoms in the chain, more typically 2 to about 6 atoms in the linkage, and one ore more unsaturated carbon—carbon bonds, typically one or two unsaturated carbon—carbon bonds. A heteroalkylene, heteroalkenylene or heteroalkenylene group will have at least one hetero atom (N, O or S) as a divalent chain member.

The term alkanoyl refers to groups that in general formulae generally will have from 1 to about 16 carbon atoms and at least one carbonyl (C=O) moiety, more typically from 1 to about 8 carbon atoms, still more typically 1 to about 4–6 carbon atoms. The term alkylthio generally refers to moieties having one or more thioether linkages and preferably from 1 to about 12 carbon atoms, more preferably from 1 to about 6 carbon atoms. The term alkylsulfinyl generally refers to moieties having one of more sulfinyl (S(O)) linkages and preferably from 1 to about 12 carbon atoms, more preferably from 1 to about 6 carbon atoms. The term alkylsulfonyl generally refers to moieties having one or more sulfonyl (S(O)$_2$) linkages and preferably from 1 to about 12 carbon atoms, more preferably from 1 to about 6 carbon atoms. The term aminoalkyl generally refers to groups having one or more N atoms and from 1 to about 12 carbon atoms, preferably from 1 to about 6 carbon atoms.

As discussed above, various substituent groups of the above formulae may be optionally substituted. Suitable groups that may be present on such a "substituted" group include e.g. halogen such as fluoro, chloro, bromo and iodo; cyano; hydroxyl; nitro; azido; sulfhydryl; alkanoyl e.g. $C_{1-6}$ alkanoyl group such as acetyl and the like; carboxamido; alkyl groups including those, groups having 1 to about 12 carbon atoms, preferably from 1 to about 6 carbon atoms; alkenyl and alkynyl groups including groups having one or more unsaturated linkages and from 2 to about 12 carbon atoms, preferably from 2 to about 6 carbon atoms; alkoxy groups having one or more oxygen linkages and from 1 to about 12 carbon atoms, preferably 1 to about 6 carbon atoms; aryloxy such as phenoxy; alkylthio groups including those moieties having one or more thioether linkages and from 1 to about 12 carbon atoms, preferably from 1 to about 6 carbon atoms; alkylsulfinyl groups including those moieties having one or more sulfinyl linkages and from 1 to about 12 carbon atoms, preferably from 1 to about 6 carbon atoms; alkylsulfonyl groups including those moieties having one or more sulfonyl linkages and from 1 to about 12 carbon atoms, preferably from 1 to about 6 carbon atoms; aminoalkyl groups such as groups having one or more N atoms and from 1 to about 12 carbon atoms, preferably from 1 to about 6 carbon atoms; carbocyclic aryl having 6 or more carbons, particularly phenyl; aryloxy such as phenoxy; aralkyl having 1 to 3 separate or fused rings and from 6 to about 18 carbon ring atoms, with benzyl being a preferred group; aralkoxy having 1 to 3 separate or fused rings and from 6 to about 18 carbon ring atoms, with O-benzyl being a preferred group; or a heteroaromatic or heteroalicyclic group having 1 to 3 separate or fused rings with 3 to about 8 members per ring and one or more N, O or 9 atoms, e.g. coumarinyl, quiolinyl; pyridyl, pyrazinyl, pyrimidyl, furyl, pyrrolyl, thienyl, thiazolyl, oxazolyl, imidazolyl, indolyl, benzofuranyl, benzothiazolyl, tetrahydrofuranyl, tetrahydropyranyl, piperidinyl, morpholino and pyrrolidinyl. A "substituted" group of a compound of the invention prepared by a method of the invention may be substituted at one or more available positions, typically 1 to about 3 positions, by one or more suitable groups such as those listed immediately above.

Particularly preferred preparative methods of the invention are exemplified in the following Schemes I through XVI. For purposes of exemplification only, particularly preferred compounds and substituents are depicted in the Schemes, and it will be understood that a variety of other compounds can be employed in similar manner as described below with respect to the exemplified compounds, For instance, the carbocyclic aryl group of 4-fluorophenol is depicted throughout the Schemes, although a wide variety of other aryl group could be employed in the same or similar manner as fluorophenyl. It should also he understood that references to "aryl" with respect to the Schemes and as otherwise specified herein includes those groups specified for the substituent Ar in Formula I above and thus encompasses carbocyclic aryl such as phenyl and the like as well as heteroaryl groups. Additionally, while compounds in the below Schemes generally depict substitution only at the ring carbons α to the ring oxygen, other ring positions can be readily substituted, e.g. by using appropriately substituted starting reagents.

SCHEME I

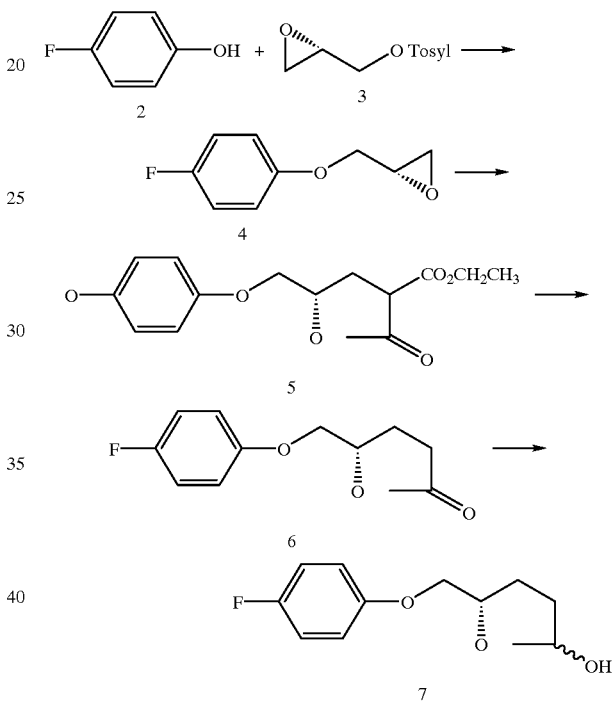

Scheme I exemplifies a preferred preparative method of the invention wherein arylhydroxide 2 is reacted with epoxide 3 having a reactive C3 carbon. Preferred epoxides are those that are enantiomerically enriched, such as the glycidyl tosylate 3 shown above that is condensed with phenol 2 for a time and temperature sufficient for reaction completion to provide epoxyaryl ether 4. See Example 1, Part 1 below for exemplary reaction conditions. The reagents 2 and 3 are typically reacted in a suitable solvent, e.g. dimethyl formamide, N-methyl pyrrolidinone and the like. Enantiomerically enriched epoxides suitable for condensation with an arylhydroxide are commercially available or can be readily prepared by known procedures. See, for instance, U.S. Pat. Nos. 4,946,974 and 5,332,843 to Sharpless et al. for preparation of optically active derivatives of glycidol.

The epoxyaryl ether 4 then is reacted with an active methylene group, such a diethyl or dimethyl malonate to provide butyrolactone 5. The exocyclic ester of 5 is then suitably cleaved, e.g. with reaction with magnesium chloride hexahydrate, to provide the aryllactone ether 6. See Example 1, Part 3 which follows for an exemplary reaction conditions. That lactone 6 is then reduced to the hydroxytetrahydrofuran 7. Suitable reducing agents include e.g. DIBAL-H and the like. See Example 1, Part 4, which follows.
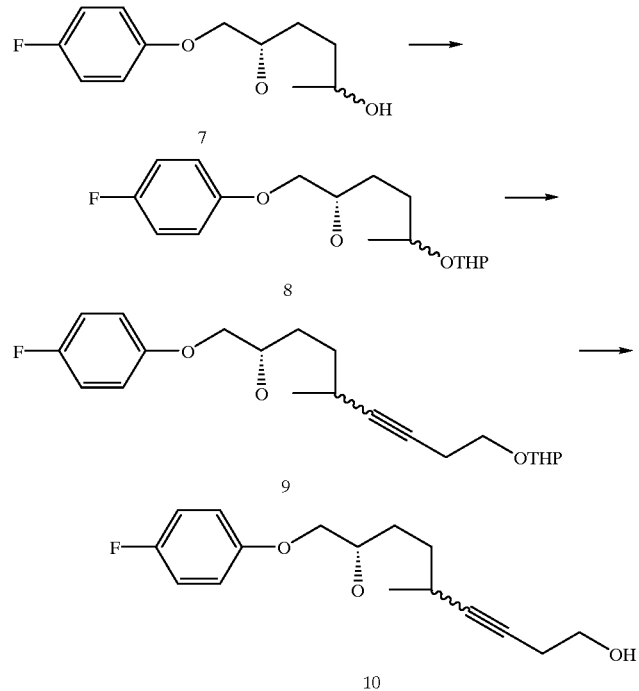
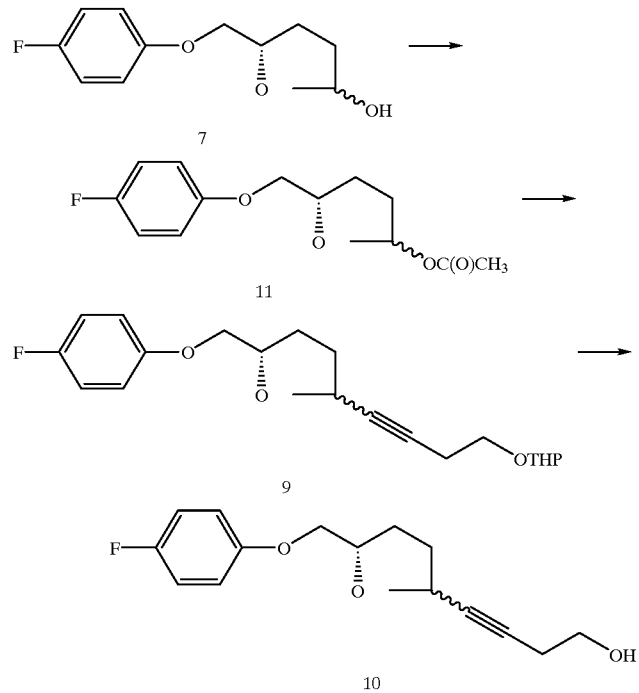

Schemes II and III exemplify further preferred methods of the invention for synthesis of alkynyl-substituted tetrahydrofuranaryl ethers. More specifically, the hydroxy substituent of tetrahydrofuran 7 is preferably protected, e.g. as an ether or ester. Thus, as depicted in Schemes II and III, the hydroxy moiety of 7 can be reacted with a suitable silyl reagent, e.g. to form the t-butyldimethylsilyl ether 8, or with reagent for esterification, e.g. an anhydride such as acetic anhydride to acetyl ester 11. See Example 1, Part 5 and Example 2, Part 1 for suitable reaction conditions for exemplary conditions.

The protected aryltetrahydrofuran ether 8 or 11 then can reacted to provide the alkynyl-substituted tetrahydrofuran 9 by treatment with a 1-alkyne in the presence of a strong base such an alkyllithium. Preferably the alkyne reagent contains a protected hydroxy moiety such as a silyl other, e.g. a tetrahydropyranyl ether as depicted in the above Schemes. The hydroxy group can be readily deprotected after coupling of the alkynyl reagent to the tetrahydrofuran ring, e.g. by treatment with dilute acid. Typically, the alkyne reagent will contain a primary or secondary hydroxy moiety.

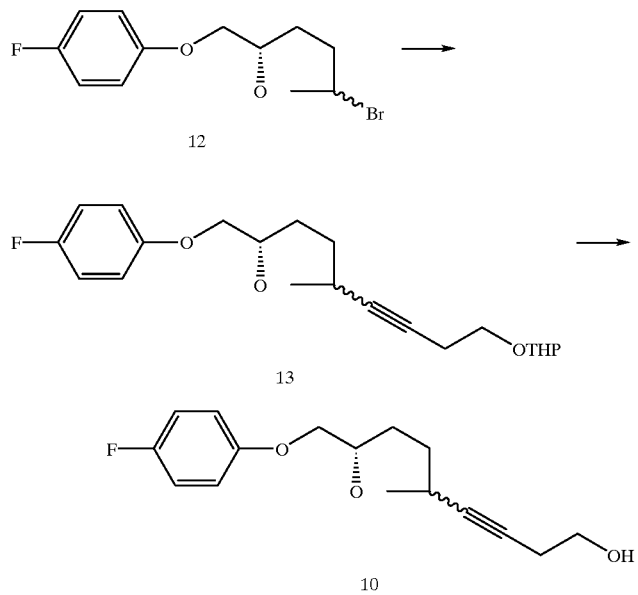

SCHEME IV

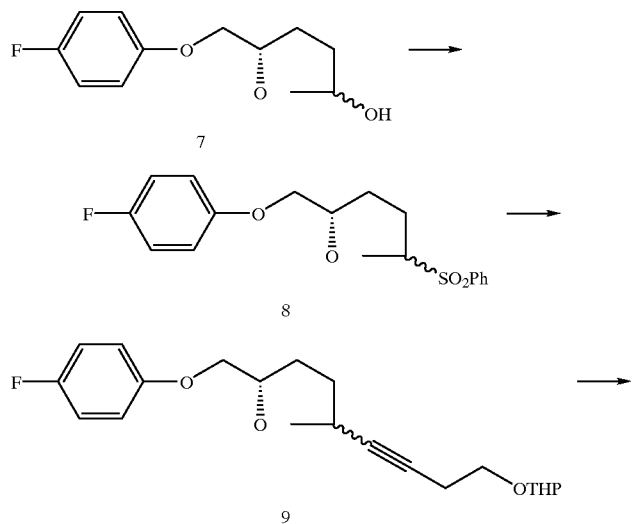

SCHEME V

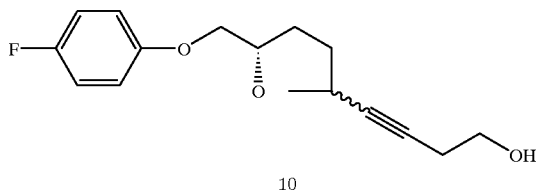

10

Schemes IV and V above exemplify further convenient routes that can provide alkynyl-substituted tetrahydrofurans of Formula I. Thus, in Scheme IV, halo-substituted compound 12 can be reacted with an alkyne reagent as generally described above with respect to Schemes II and III to provide 9, which can be readily deprotected to provide the primary alcohol of compound 10. See generally Example 3 which follows for exemplary reaction conditions.

In Scheme V, hydroxytetrahydrofuran 7 (depicted as the lactol) is condensed with a sulfonic acid reagent to provide the sulfonic ester 8 which can be reacted with an alkyne reagent as generally described above to provide 9. Compound 10 is readily provided by treatment of the protected alcohol 9 with treatment with dilute acid. See Example 4 below.

Scheme VI below exemplifies a further preferred method of the invention that provides compounds of Formula I and involves cleavage of a bis-compound to provide high yields of compounds of Formula I.

SCHEME VI

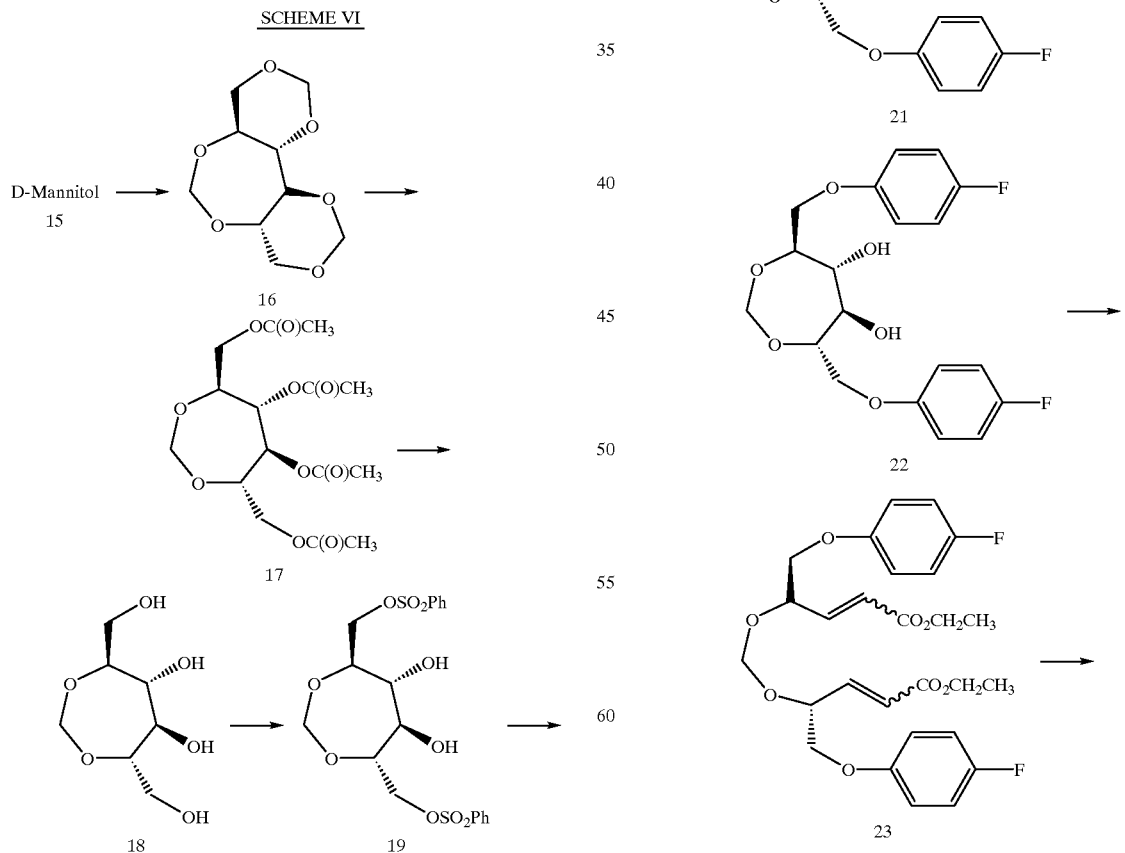

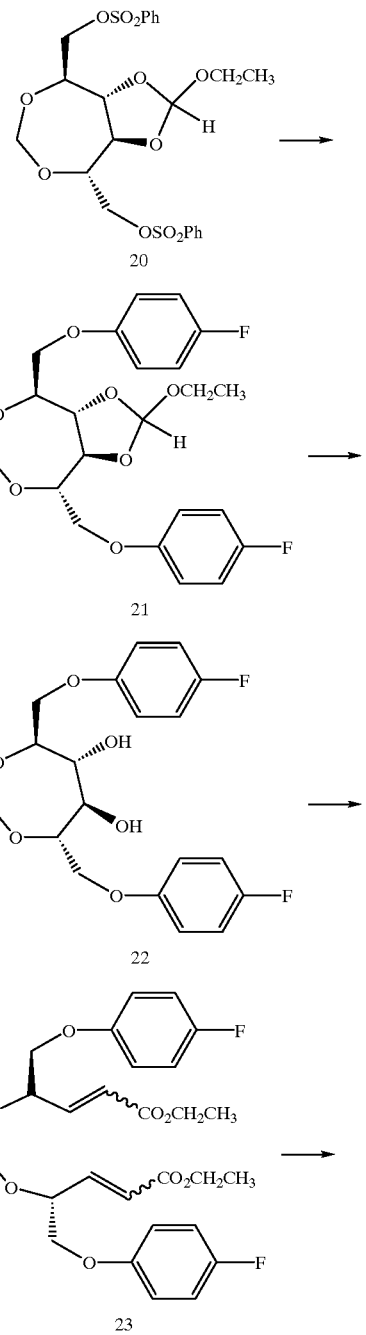

19
-continued

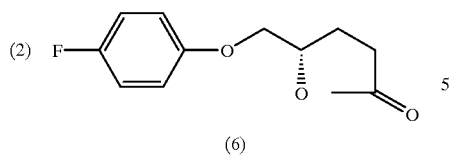

(2)

(6)

More specifically, as depicted above, trimethylene mannitol 16 is suitably prepared by condensation of mannitol 15 with formaldehyde in the presence of acid. The labile rings are cleaved and the resulting esters of 17 reduced to the primary and secondary alcohols of 18. The primary alcohols are protected, e.g. as an allyl or aryl sulfonic ester, to provide intermediate 19. The secondary hydroxyl groups of 19 then are functionalized by reaction with a trialkylorthoformate, e.g. a tri($C_{1-10}$alkyl)orthoformate such as triethylorthoformate, to provide 20. The protected primary alcohols of 20 are then converted to aryl ethers, preferably under basic conditions by reaction with an arylhydroxide compound such as a phenol to provide di-aryl ether 21. That aryl ether is then reacted in the presence of acid to cleave the methylene ethers to provide secondary hydroxyl groups of compound 22.

Compound 22 then undergoes oxidative cleavage by treatment with a suitable reagent such as $Pb(OAc)_4$, and the resulting dialdehyde is functionalized to the acyclic α,β-unsaturated ester 23 such as by reaction with carboethoxymethylenetriphenyl phosphorane. Other α,β-unsaturated groups will for suitable for the alicyclic compound, e.g. α,β-unsaturated esters have 1 to about 12 carbon atoms, α,β-unsaturated acids, and other Michael-type acceptors. The carbon—carbon double bonds of 23 then are saturated, preferably by hydrogenation, and the resulting compound is cleaved and cyclized in the presence of acid to form the aryl ether 6. In one system, the saturated compound is refluxed in a suitable solvent such as an alcohol, ethanol, for a time sufficient to provide 6. See Example 5 which follows for exemplary reagents and reaction conditions. Compound 6 then can be further functionalized, e.g. as discussed above with respect to Schemes II and III.

SCHEME VII

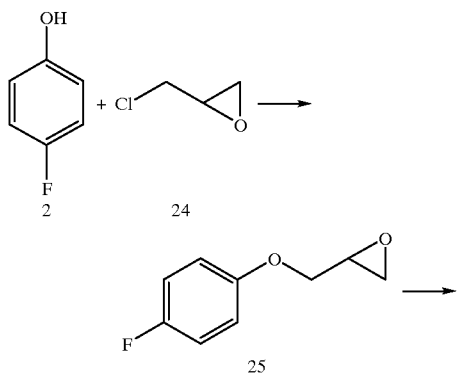

20
-continued

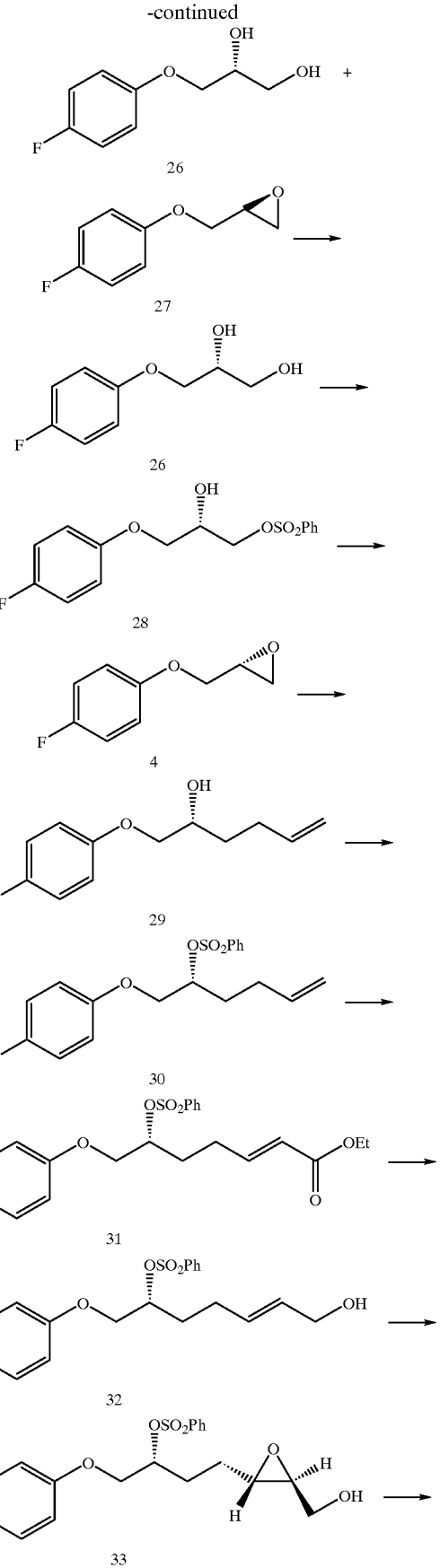

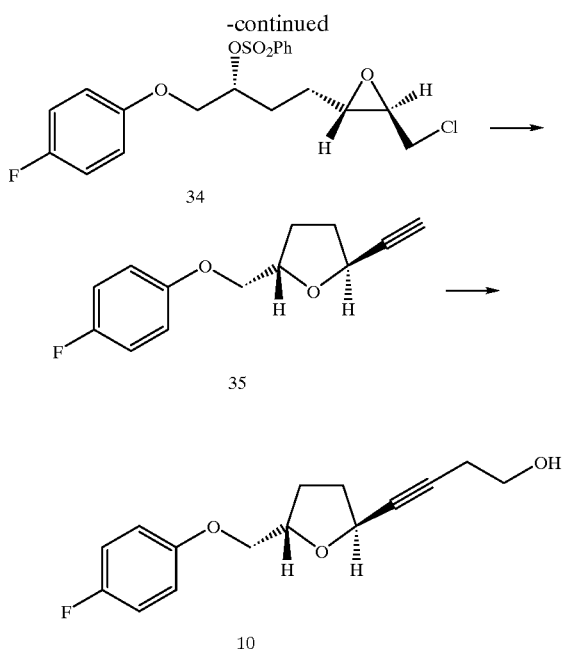

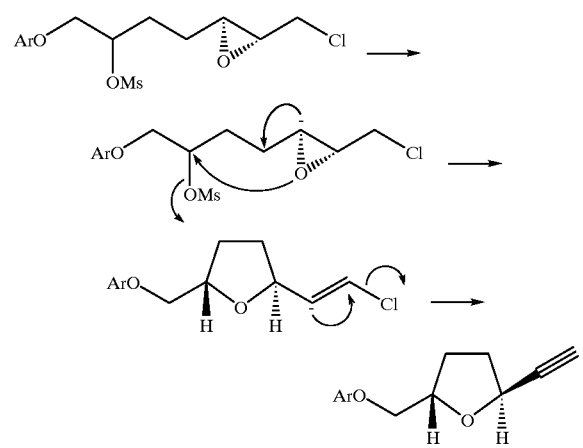

Scheme VII above exemplifies a further preferred method of the invention that provides compounds of Formula I and features multiple reactions that proceed as a single step without isolation of intermediates.

More specifically, as shown above aryl compound 2 is reacted with epoxide 24 that has a reactive C3 carbon to provide the arylepoxy ether 25. If the epoxide 24 is not enantiomerically enriched such as 3, the arylepoxy ether 25 may be resolved if desired such as by procedures generally depicted in Scheme VI above to provide optically active epoxide ethers 27 and 4. See Example 6, Parts 2–4 below for exemplary reagents and reaction conditions. That procedure generally entails formation of optically active aryldiol ether and arylepoxide ether 26 and 27 from the racemic arylepoxide 25 with an optically active reagent, preferably an optically active catalyst such as Jacobsen's catalyst. See E. Jacobsen, Science, 277:936–938 (1997). The optically active diol 26 can be readily cyclized to the epoxide 4, for example by esterification (e.g. a sulfonic ester as shown exemplified by 28 above) of the primary hydroxyl group of the diol followed by epoxide formation under basic conditions (e.g. NaH).

An allyl halide is suitably reacted with the arylepoxide ether, suitably in the presence of Mg, catalytic amount of iodine and cuprous cyanide to provide aryl/alkene ether 29. The secondary hydroxy is suitably protected, e.g. as an ester, preferably as a sulfonic ester, to provide 30. An ester group is then suitably grafted to terminal carbon—carbon double bond to the α,β-unsaturated ester 31, and the ester reduced to the alcohol, typically by treatment with strong base such as DIBAL-H.

The alkene is then suitably oxidized to provide epoxy group of 33. The oxidation may be conducted to provide optically active epoxy carbons as generally shown in Scheme VI (compound 33) and conducted using suitable optically active reagent(s) such as an optically catalyst or other reagent. See Example 6, Part 9 for an exemplary procedure. The racemic epoxides also may be resolved, e.g. by chromatography using an optically active packing material. The glycidyl compound 33 is then converted to the epihalohydrin 34.

The epihalohydrin 34, in a single step, is converted to the alkynyltetrahydrofuran ether 35 upon treatment with a molar excess, preferably at least about a three molar excess of a strong base such as an alkyllithium reagent or sodium amide. BuLi is generally preferred, particularly n-BuLi.

While not being bound by theory, it is believed the single step reaction proceeds through the mechanism shown immediately below, where Ar is the same as defined for Formula I and Ms is mesyl (—S(O)$_2$CH$_3$):

The alkynyl group of compound 35 can be further functionalized as desired, e.g. by reaction with ethylene oxide in the presence of base to afford the single enantiomer 10.

Compound 10 also can be further functionalized as desired. For example, to produce compound 1 as shown above, compound 10 can be reacted with N,O-bisphenoxycarbonyl hydroxylamine and triphenylphosphine and diisopropylazodicarboxylate, followed by treatment of resulting intermediate with NH$_3$.

However, in a preferred aspect and as discussed above, the invention provides new routes to substituted hydroxy ureas. More particularly, a protected hydroxyurea (e.g., a compound of the formula NH$_2$C(O)NHOR, where R is a hydroxy protecting group such as an alkyl, aryl or preferably aryalkyl ether such as an ether of an optionally substituted (phenyl)OCH$_2$—) is reacted with a substituted alcohol compound such as 10 of Scheme II, preferably in the presence of suitable dehydrating agent(s) such as triphenyl phosphine and diethylazodicarboxylate (DEAD) to provide an amino ester, i.e. a moiety of the formula —NRC(O)OR$^1$R where R is as defined immediately above and R$^1$ is a non-hydrogen group such as aryl, particularly phenyl, alkyl, e.g. C$_{1-10}$ alkyl, etc. That amino ester is then treated with ammonia and a Lewis acid such as boron trifluoride etherate and the like to provide a hydroxy urea.

Schemes VIII, IX and X exemplify preferred methods for synthesis of substituted oxepanes in accordance with the invention.

Scheme VIII

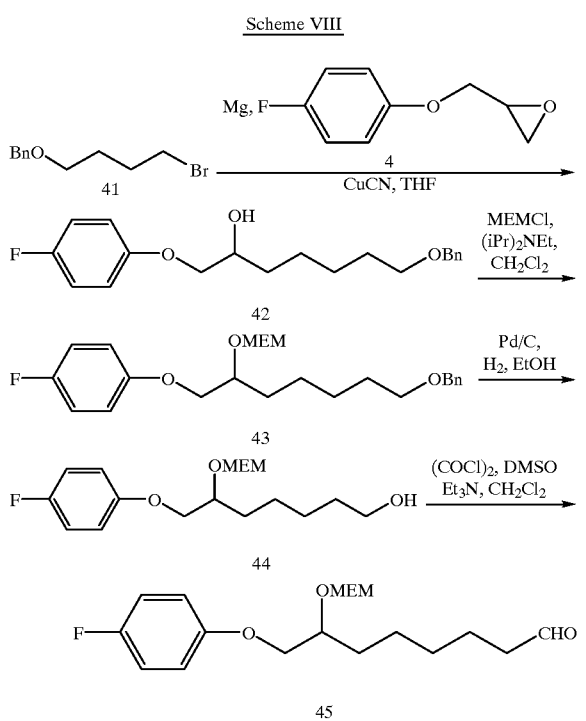

Thus, as generally shown in Scheme VIII above, the halo benzyloxyalkane 41 is condensed with an arylether oxirane in the presence of an appropriate metal for a time and temperature sufficient for reaction completion to provide the arylbenzylether hydroalkane 42. The hydroxyl functionality of the arylether 42 is suitably protected especially as an ether such as methoxyethoxymethyl ether, methoxymethyl ether or tetrahydropyranyl ether and the like to provide the intermediate 43. The benzyl protection group of arylether 43 is removed under appropriate conditions such as hydrogenation using palladium on activated carbon. The resulting primary alcohol 44 is then oxidized to the corresponding aldehyde 45 using an appropriate oxidizing agent such as oxalyl chlorine with dimethyl sulfoxide in an appropriate solvent such as methylene chloride or chloroform, or a buffered solution of pyridinium dichromate in dry methylene chloride.

Scheme IX

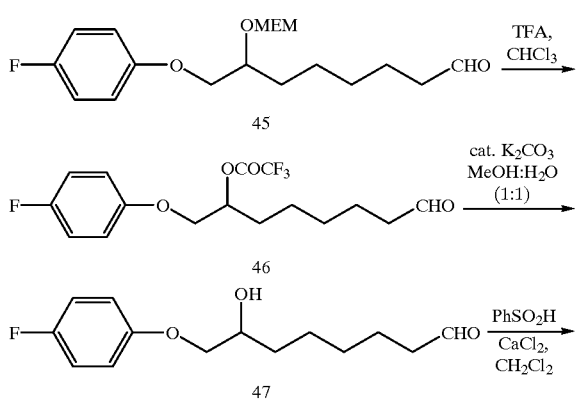

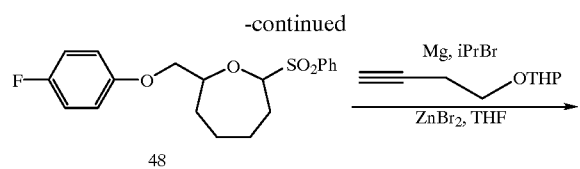

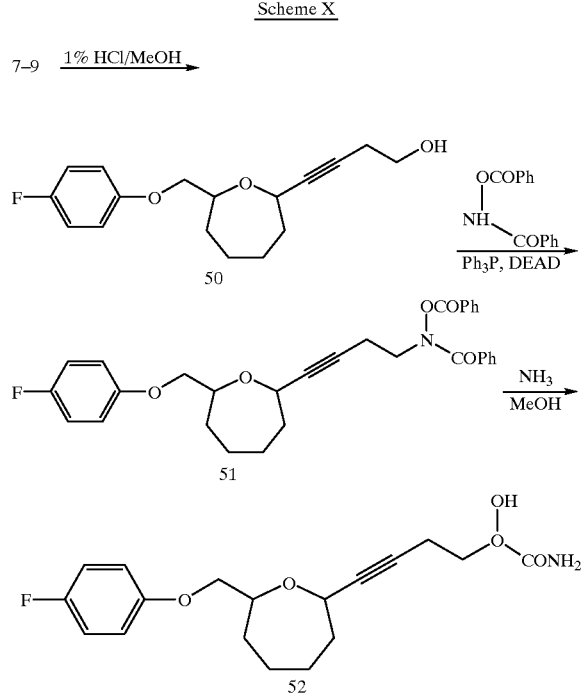

The hydroxy group of 49 can be readily deprotected after coupling of the alkynyl reagent to the oxepane ring, e.g. by treatment with dilute acid such as a 1% HCl methanol solution to provide the alkynylhydroxy substituted oxepane 50 as shown in Scheme X. The arylether alkynylhydroxy oxepane 50 can be further functionalized as desired e.g. by amidation using a N,O-substituted hydroxylamine, preferably in the presence of dehydrating reagents such as triphenylphosphine and diisopropylazodicarboylate, followed by treatment of the resulting intermediate 51 with ammonia to yield the hydroxylamine oxepane 52. See the above discussion and Example 7, Parts 9 and 10 which follow for exemplary reaction conditions.

Synthetic methods of the invention also include preparation of compounds useful as intermediates to prepare 2,7-disubstituted tetrahydropyran compounds of the above Formula I.

Scheme XI

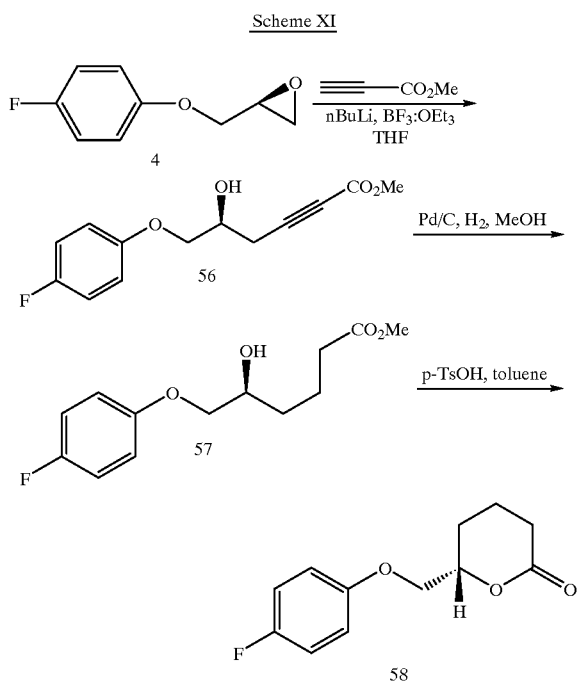

Schemes XI, XII and XIII exemplify some preferred preparative methods of the invention for synthesis of alkynyl-substituted tetrahydropyrans.

Generally as shown is Scheme XI, the epoxy aryl ether 4 is reacted with a 1-alkyne reagent in the presence of a strong base such as butyl lithium and boron trifluoroetherate in THF to yield the alkyne 56. Preferably the alkyne reactant contains an ester moiety such as a methyl ester. The alkynyl functionality of arylether 56 is reduced under appropriate conditions such as hydrogenation using palladium on activated carbon as catalyst in an appropriate solvent such as methanol or ethanol to yield the alkane 57. Rearrangement with cyclization of the arylether methyl ester 57 is done by treatment with toluenesulfonic acid preferably in an appropriate solvent such as toluene to yield the tetrahydropyrrolinone 58.

Scheme XII

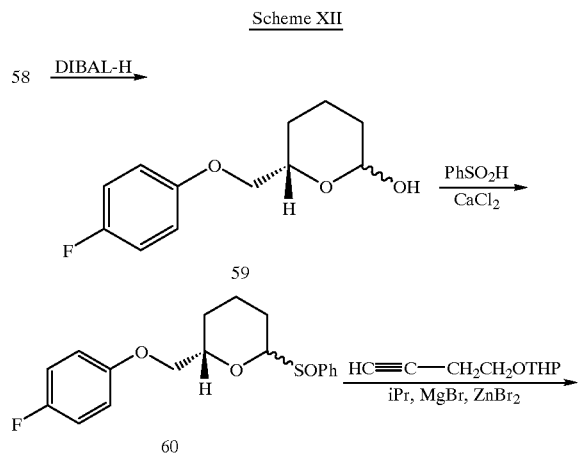

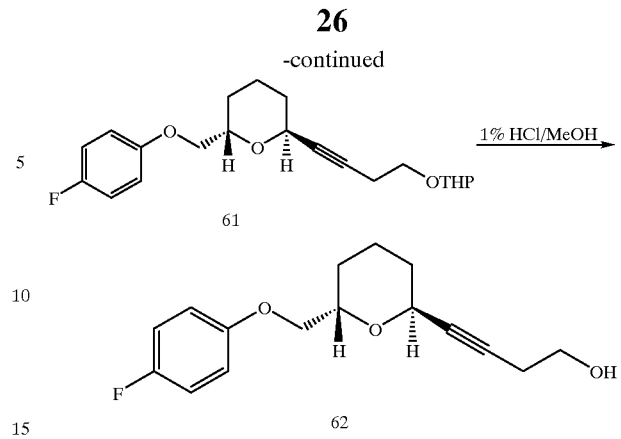

The aldehyde 58 is reduced, e.g. by reaction with diisobutylaluminum hydride to yield the corresponding alcohol 58 as shown in Scheme XII. The arylether alcohol 59 and benzylsulfonic acid react in an appropriate solvent such as methylene chloride or chloroform in the presence of a drying agent such as calcium chloride to afford the cyclized arylether benzylsulfonic tetrahydropyran 60. The benzylsulfonic tetrahydropyran 60 can then react with a I-alkyne in the presence of magnesium and isopropyl bromide to provide the alkynyl-substituted tetrahydropyran 61. Preferably the alkyne reactant contains a protected hydroxyl moiety such as tetrahydropyranyl ether or t-butyldimethylsilyl ether. It has been surprisingly found that reaction of the alkyne reagent with a mixture of a stereoisomers of 60 (i.e. racemic at phenylsulfinic-substituted ring carbon) proceeds stereoselectively to produce the trans compound 61. In fact, it has been found that the trans 61 compound can be the exclusive reaction product. The hydroxy group of 61 can be readily deprotected after coupling of the alkynyl reagent to the oxepane ring, e.g. by treatment with dilute acid such as a 1% HCl methanol solution to provide the alkynylhydroxy substituted tetrahydropyran 62.

Scheme XIII

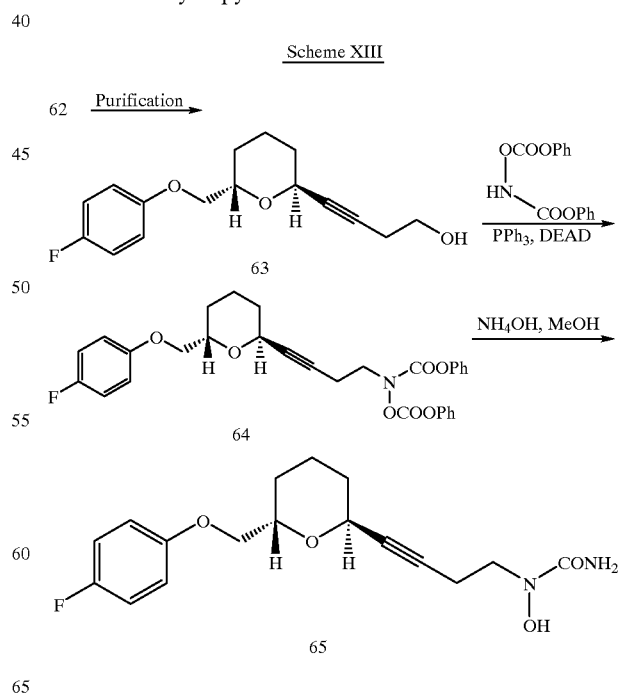

The arylether alkynylhydroxy tetrahydropyran 62 can be purified to yield the enantiomerically enriched disubstituted tetrahydropyran 63. The arylether alkynylhydroxy tetrahydropyran 63 further functionalized as desired by amidation using a N,O-substituted hydroxylamine, preferably in the presence of dehydrating reagents such as, triphenylphosphine and diisopropylazodicarboylate, followed by treatment of the resulting intermediate 64 with ammonia to yield the hydroxylamine tetrahydropyran 65.

Synthetic methods of the invention also include preparation of compounds useful as intermediates to prepare 2,7-disubstituted oxepane compounds of the above Formula II.

Scheme XIV below another preferred preparative method of the invention that employs a polyol (polyhydroxy) reagent. As depicted in the below Scheme, the entire reaction is stereoselective (i.e. no separate resolution step or procedure required), beginning with the optically active glyceraldehyde 1, which is commercially available. Other glyceraldehyde stereoisomers can be employed in the same manner as depicted in Scheme VIII to provide the corresponding distinct stereoisomer as the reaction scheme product.

In the following Schemes XIV through XVI, the compound numerals in the discussions of those Schemes are made in reference to the compound depicted in the particular Scheme, with the exception of compound 1, i.e. 2-(4-fluorophenoxymethyl)-5-(4-N-hydroxyureidyl-1-butynyl)-tetrahydrofuran.

As generally exemplified in Scheme XIV below, the chiral synthon (glyceraldehyde) is cyclized in the presence of base to the bis-dioxolane compound 2 which is then oxidized to the keto (aldehyde) dioxolane 3 and reacted with an appropriate Wittig reagent to provide the α,β-unsaturated ester 4. As referred to herein, unless specified otherwise, the term "Wittig reaction" or "Wittig-type reaction" designates any of the broad classes of alkene-formation reactions, typically involving ylide intermediates such as may be provided by phosphonate and phosphorane reagents. Additionally, as referred to herein, unless otherwise specified, to "keto", "carbonyl", or "carboxy" or like term designate any functional group that includes a carbon—oxygen double bond (C=O).

The carbon—carbon double bond produced by the Wittig reaction then can be saturated, e.g. hydrogenated in the presence of a suitable catalyst such as PtO$_2$, and the ester reduced and then oxidized to provide aldehyde 7. Wittig reaction of the aldehyde moiety provides the α,β-maturated compound 9 which can be reduced to alcohol 9, and converted to the propargyl compound, e.g. via an epoxidized intermediate. More specifically, unsaturated alcohol 9 can be epoxidized to compound 10, suitably with an optically active oxidant and then elimination of the epihalohydrin derivative 11 in the presence of a suitable base e.g. LDA or other suitable agent to provide the propargyl compound 12. Additional, successive Wittig-type reactions with intervening carbon—carbon double bond saturation and aldehyde formation can be employed to prepare larger oxygen ring compounds. Thus, to prepare six-member oxygen alicyclic compounds of the invention, the sequence of steps shown in Scheme XIV below in the transformation of compound 3 to 7 would be repeated to compound 9a (which is compound 9 oxidized to the corresponding aldehyde). Similarly, to prepare seven member oxygen alicyclic compounds of the invention, the sequence of steps shown in Scheme XIV below in the transformation of compound 3 to 7 would be repeated two more times; to prepare eight member oxygen alicyclic compounds of the invention, the sequence of steps shown in Scheme XIV below in the transformation of compound 3 to 7 would be repeated three more times beyond that shown in the Scheme. Alternatively, or in combination with successive Wittig reactions, other Wittig reagents can be employed that provide for greater chain extension in a single step, e.g. Ph$_3$P=CHCH$_2$CO$_2$Et, Ph$_3$P=CHCH$_2$CH$_2$CO2Et, and the like, or corresponding Wadsworth-Emmons reagents.

Acidic opening of the dioxolane ring provides diol 14 and esterification (e.g. sulfonate ester such as a tosylate) provides the substituted tetrahydrofuran 16. The resulting hydroxy tetrahydrofuran can be functionalized as desired, e.g. esterification of the hydroxy followed by aryl substitution and functionalization of the alkynyl group provides compound 1, particularly 2S,5S-trans-(4-fluorophenoxymethyl)-5-(4-N-hydroxyureidyl-1-butynyl)-tetrahydrofuran. See, generally, Example 11 which follows for exemplary preferred reaction procedures.

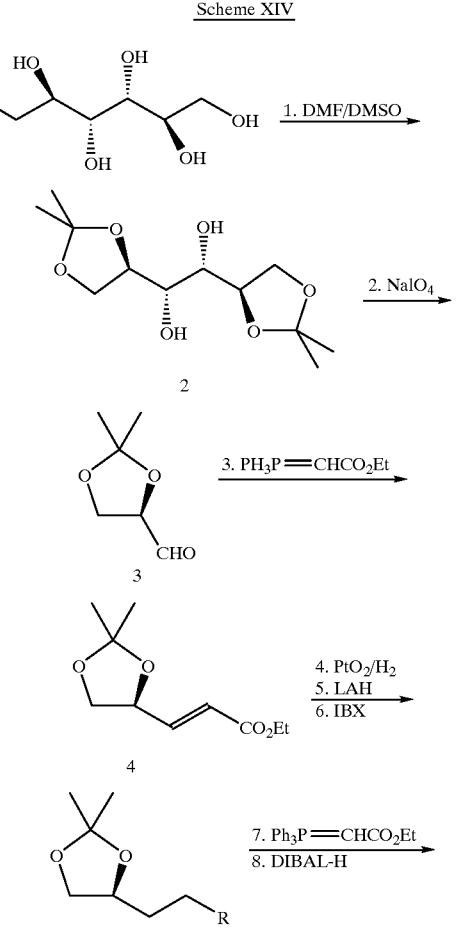

Scheme XIV

-continued

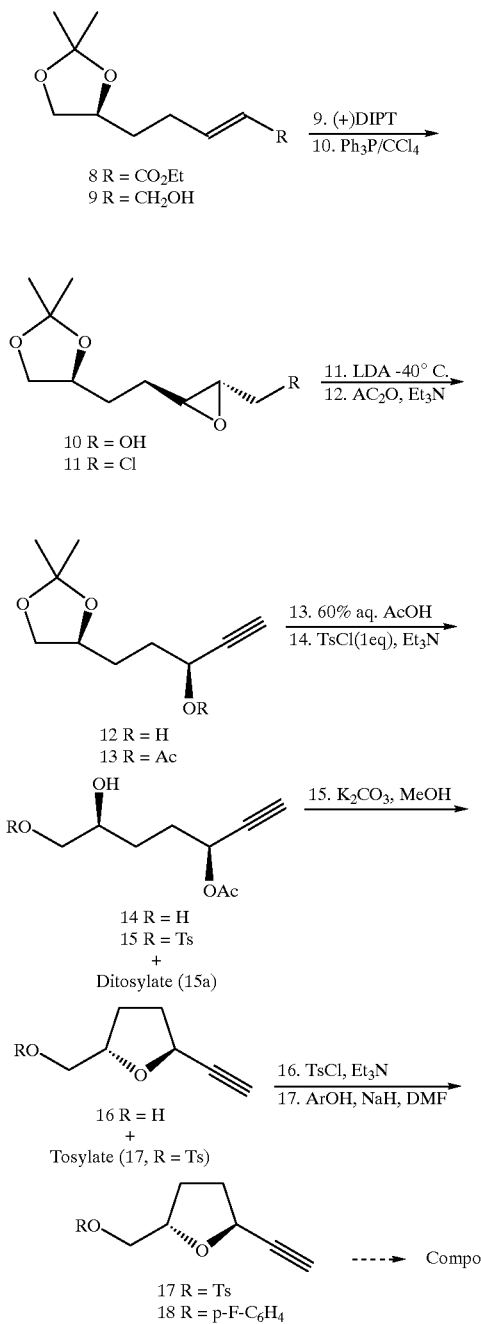

Scheme XV

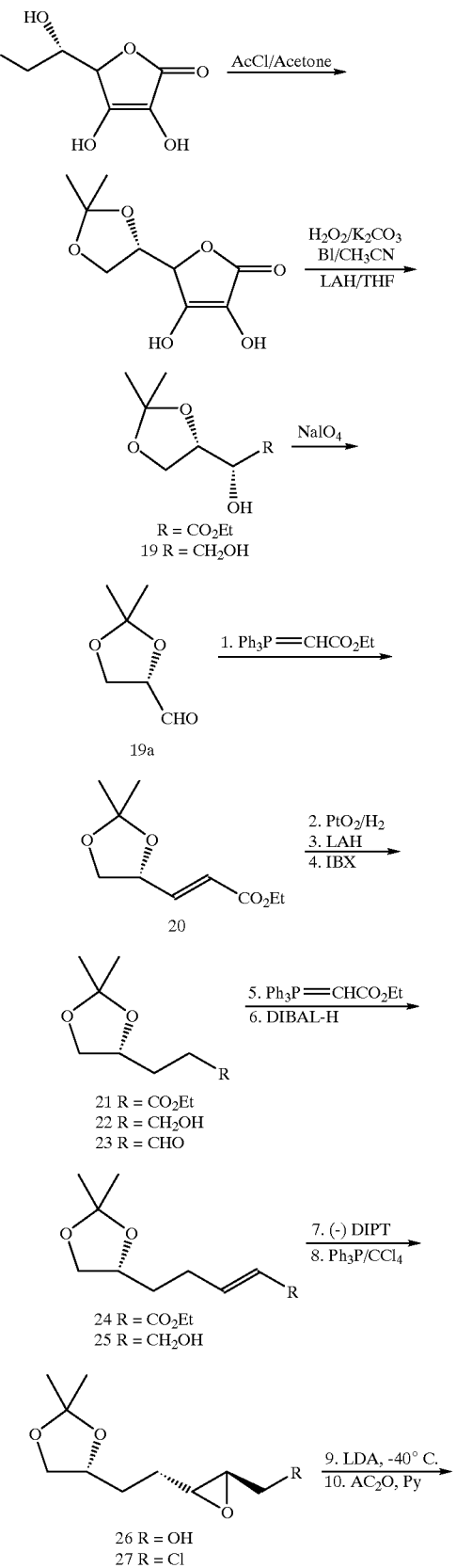

Scheme XV depicts a related approach to provide another stereoisomer of a substituted oxygen alicyclic compound. As shown in Scheme XV, L-ascorbic acid can be employed as a starting reagent to provide hydroxy dioxolane compound 19, which is oxidized; subjected to multiple Witting reactions; epoxidized; and an epihalohydrin intermediate reacted in the presence of base to form a propargyl alcohol intermediate, which is converted to the optically active aryl-substituted alkyne tetrahydrofuran compounds 33 and 34. To produce larger ring compounds, additional, successive Wittig reactions can be carried out, as discussed above with respect to Scheme XIV.

-continued

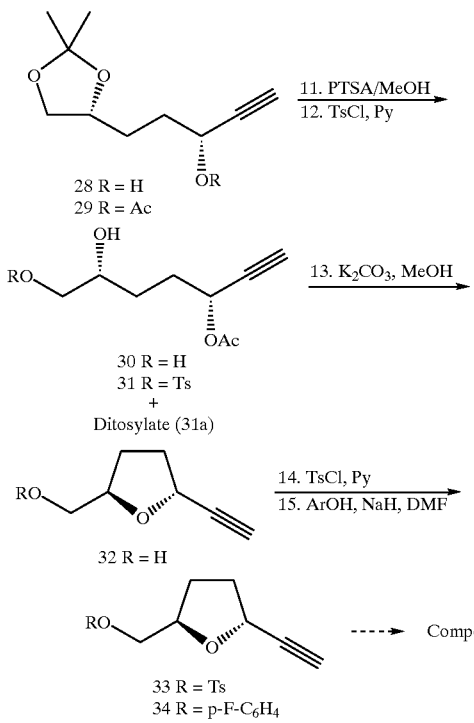

It should be appreciated that the unsubstituted alkyne produced through the routes of Schemes XIV and XV above is a versatile intermediate that can be further reacted to provide a wide range of moieties, including groups that can be detected, either upon in vitro or in vivo applications. For instance, the unsubstituted alkyne can be reacted with a group to provide radiolabeled and stable isotopic moieties, e.g. $^{125}I$, $^{3}H$, $^{32}P$, $^{99}Tc$, $^{14}C$, $^{13}C$, $^{15}N$ or the like, which may be useful inter alia for mechanistic studies.

Scheme XVI below depicts highly efficient routes to oxygen alicyclic compounds of the invention. As shown in the Scheme, butynyl reagent 52 is treated with base, preferably a strong base such as an alkyl lithium e.g. butyl lithium, and then reacted with an unsaturated anhydride 53 to provide the keto alkynyl compound 54 with terminal alkene group. The alkene group is oxidized, e.g. via ozonolysis, and the keto-epoxide compound 55 reduced and cyclized in the presence of a suitable reducing agent, e.g. borane dimethyl sulfide. The resulting hydroxy tetrahydrofuran can be functionalized as desired, e.g. esterification of the hydroxy moiety followed by aryl substitution and functionalization of the alkynyl group provides 2-(4-fluorophenoxymethyl)-5-(4-N-hydroxyureidyl-1-butynyl)-tetrahydrofuran. See Example 12 which follows for exemplary preferred reaction conditions.

Larger ring compounds also can be prepared by this general route, e.g. by reaction of corresponding ring-extended compounds corresponding to compound 53 below. That is, to prepare oxygen alicyclic compounds having six ring members, the compound $CH_2=CH(CH_2)_3C(=O)OCOOEt$ can be employed in place of compound 53 in the below Scheme; to prepare oxygen alicyclic compounds having seven ring members, the compound $CH_2=CH(CH_2)_4 C(=O)OCOOEt$ can be employed in place of compound 53 in the below Scheme; and to prepare oxygen alicyclic compounds having eight ring members, the compound $CH_2=CH(CH_2)_4C(=O)OCOOEt$ can be employed in place of compound 53 in the below Scheme.

Scheme XVI

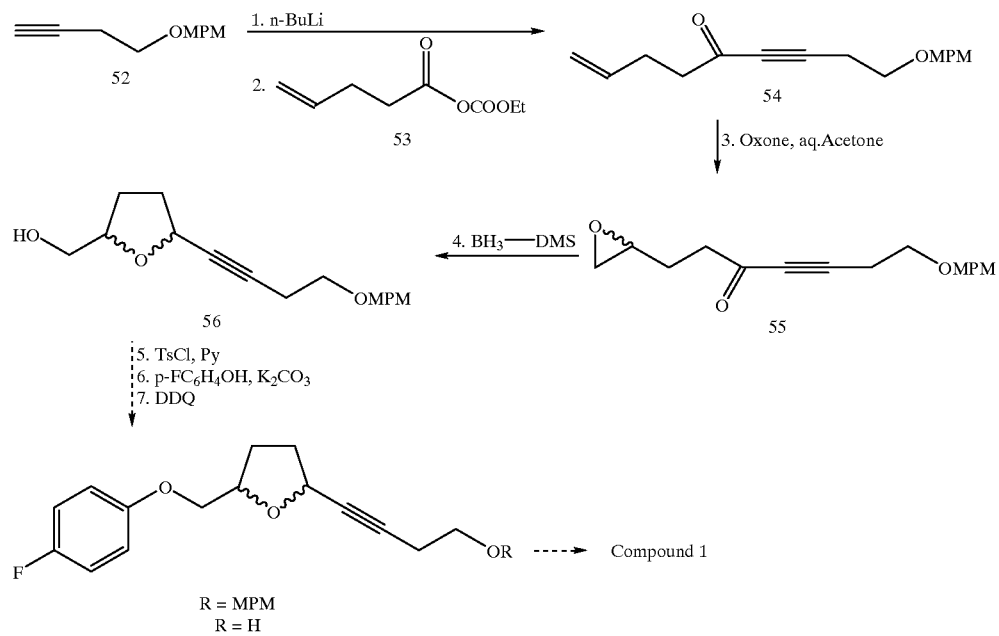

Schemes XVII and XVIII below depict routes to alicyclic compounds of the invention having one or preferably more hydroxy or alkoxy (e.g. $C_{1-12}$ alkoxy, more preferably $C_{1-8}$ or $C_{1-6}$ alkoxy) substituents, preferably two hydroxy or alkoxy substituents on adjacent (vicinal) ring positions of the alicyclic compound. Thus, as shown in Scheme XVII below, mannose diacetonide 70 is converted to sulfide 72 followed by hydrolysis to provide 73. The alkylhydroxy ring substituent of 73 can be functionalized as desired, e.g. activation of a carbon such as by esterification (e.g. sulfonate, such as tosylate, mesylate, etc.) and nucleophilic substitution of the activated carbon, e.g. by an aryl nucleophile, particularly a carbocyclic aryl nucleophile such as a optionally substituted phenol. Other ring positions can be functionalized as desired, e.g. as shown in Scheme XVII, the sulfide group can be oxidized to the sulfone 74 to activate the ring carbon and that position substituted by a suitable reagent, erg. a terminal alkyne, to provide compound 75. The vicinal alkoxy groups of compounds 75 and 76 can be readily converted to the corresponding vicinal di-hydroxy groups by acidic hydrolysis. Scheme XVIII shows alternate functionalization of the alicyclic compound. The di-alkoxy compounds 85 and 86 can be converted to the corresponding vicinal di-hydroxy compounds by acidic hydrolysis.

Scheme XVII

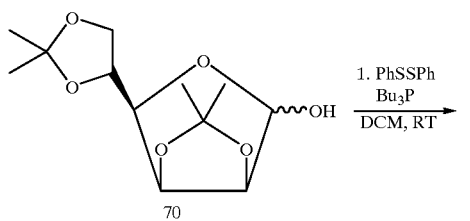

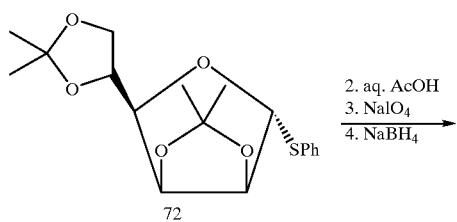

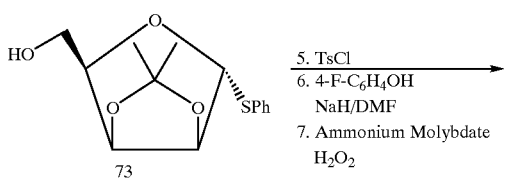

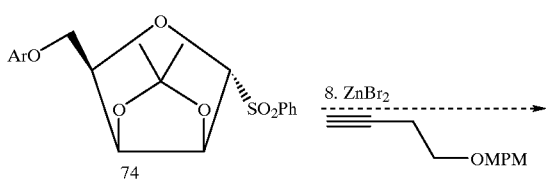

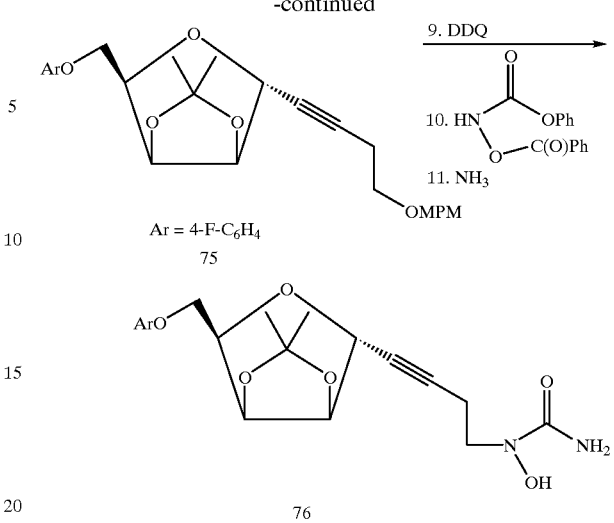

Scheme XVIII

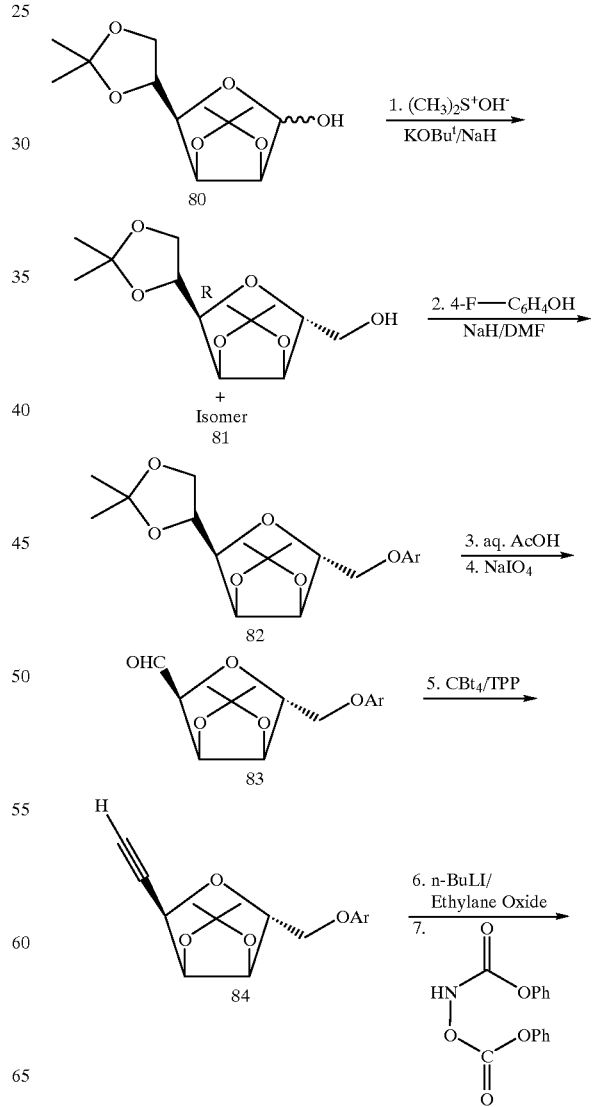

-continued

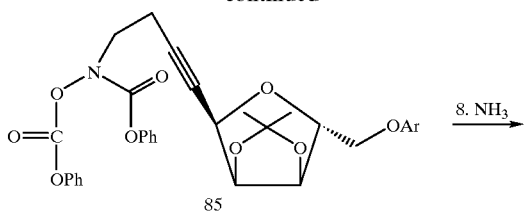

85

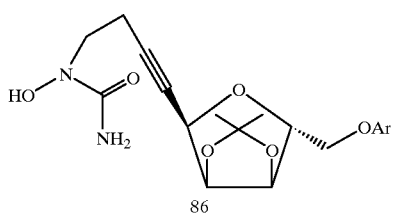

86

Often, it will be preferable to use an optically active or enantiomerically enriched mixture of a chiral compound of the invention for a given therapeutic application. As used herein, the term "enantiomerically enriched" refers to a compound mixture that is at least approximately 85% or 90%, and preferably a mixture of approximately at least about 95%, 97%, 98%, 99%, or 100% of a single enantiomer of the compound.

As discussed above, compounds of the invention are useful for numerous therapeutic applications. The compounds can be administered to a subject, particularly a mammal such as a human, in need of treatment, by a variety of routes. For example, the compound can be administered orally, parenterally, intravenously, intradermally, subcutaneously, or topically. For example, for parenteral application, particularly suitable are solutions, preferably oily or aqueous solutions as well as suspensions, emulsions, or implants, including suppositories. Ampules are convenient unit dosages. For enteral application, particularly suitable are tablets, dragees or capsules e.g. having talc and/or carbohydrate carrier binder or the like, the carrier suitably being lactose and/or corn starch and/or potato starch.

The active compound may be administered to a subject as a pharmaceutically active salt, e.g. salts formed by addition of an inorganic acid such as hydrochloric acid, hydrobromic acid, phosphoric acid, etc., or an organic acid such as acetic acid, oxalic acid, tartaric acid, succinic acid, etc. Base addition salts also can be formulated if an appropriate acidic group is present on the compound. For example, suitable base addition salts include those formed by addition of metal cations such as zinc, calcium, etc., or salts formed by addition of ammonium, tetraethylammonium, etc. Suitable dosages for a given therapy can be readily determined by the medical practitioner based on standard dosing protocols. See also U.S. Pat. No. 5,703,093.

All documents mentioned herein are incorporated herein by reference. The following non-limiting examples are illustrative of the invention.

EXAMPLE 1

Preparation of (2S)(5R)-2-(4-fluorophenoxymethyl)-5-(4-hydroxybutyn-1-yl)-tetrahydrofuran (Scheme II; 10)

Part 1: (S)-Glycidyl-4-fluorophenyl ether (Scheme I; 4)

In a 100 ml two-necked round bottom flask equipped with magnetic stir bar, nitrogen inlet and a septum, was taken sodium hydride (60% dispersion in oil, 0.742 g, 0.0185 mol) and 10 mL of dry dimethyl formamide (DMF). The reaction mixture was cooled to 0° C. and 4-fluorophenol 2 (1.9 g, 0.017 mol) in dry DMF (20 mL) was introduced. The reaction mixture was stirred at room temperature for 1 hour and cooled to 0° C. (S)-Glycidyl tosylate 3 (3.52 g, 0.015 mol) in DMF (10 mL) was added, and the reaction mixture was stirred at room temperature and monitored by TLC (EtOAc-light petroleum ether 1:4, Rf=0.5). After 4 hours, the reaction mixture was quenched by addition of ice-water (1 mL) and extracted with (2×25 mL) ethyl ether. The ever layer was washed with water, brine, dried over $Na_2SO_4$ and concentrated under reduced pressure to afford (S)-glycidyl-4-fluorophenyl ether 4, crude yield 3.6 g. The crude compound was purified by distillation at 160°–170° C./9 mm, to yield 1.98 g (76%) of purified product 4, $[\alpha]_D$+4.96° (c 2.335, $CHCl_3$). $^1H$ NMR (200 MHz, $CDCl_3$): δ 2.68 (dd, J=4.5, 2.2 Hz, 1 H), 2.85 (t, J=4.5 Hz, 1 H), 3.27 (m, 1 H), 3.89 (dd, J=15.7, 6.7 Hz, 1 H), 4.11 (dd, J=15.7, 4.5 Hz, 1 H), 6.74–7.02 (m, 4 H).

Part 2: (4S)-2-carboethoxy-(4-fluoro-phenoxy-methyl)-γ-butyrolactone (Scheme I; 5)

In a 50 ml two-necked round bottom flask equipped with magnetic stir bar, nitrogen inlet septum, sodium salt of diethyl malonate (prepared from 1.8 mL/0.0118 mol of diethyl malonate and 0.245 g/0.0106 mol of sodium) in dry THF (10 mL) was taken. The reaction mixture was cooled to 0° C. and (S)-glycidyl-4-fluorophenyl ether 4(1.788 g, 0.0106 mol) in tetrahydrofuran (THF) (10 mL) was added. The reaction mixture was stirred at room temperature and monitored by TLC, (EtOAc-light petroleum 1:3, Rf=0.30). After 12 hours, TBIF was removed on rotavapor. The residue was dissolved in ethyl acetate (25 mL) and washed with water, brine, dried over $Na_2SO_4$ and concentrated on rotavapor to afford (4S)-2-carboethoxy-(4-fluoro-phenoxy-methyl)-γ-butyrolactone 5, with a crude yield of 2.816 g. That crude product was purified on silica gel column chromatography using EtOAc-light petroleum ether (1:8) to provide 2.10 g (70%) of purified product 5, m.p.69–71° C., $[\alpha]_D$+16.950 (c 1.51, $CHCl_3$). $^1H$ NMR (200 MHz, $CDCl_3$): δ 1.3 (m, 3 H), 2.37–2.9 (m, 2 H), 3.52–3.8 (m, 1 H), 3.95 4.32 (m, 4 H), 4.68–4.82 (m, ⅓ H), 4.82–4.98 (m, ⅔ H), 6.72–7.01 (m, 4 H). It is also noted that the crude product can be suitably employed directly in the decarboxylative elimination of Part 3 below.

Part 3: (4S)-4-fluorophenoxy-methyl)-γ-butyrolactone (Scheme I; 6)

(4S)-2-carboethoxy-(4-fluoro-phenoxy-methyl)-γ-butyrolactone 5 (2.1 g, 0.0074 mol) and N,N-dimethylacetamide (10 mL) were taken in a 25 mL round bottom flask equipped with a stir bar and reflux condenser. $MgCl_2.6H_2O$ (1.51 g, 0.0074 mol) was added, and the reaction mixture was heated under reflux for 4 hours and monitored by TLC (EtOAc-light petroleum 1:2, Rf=0.2).

The reaction mixture then was partitioned between ethyl ether and water (50 mL each). The ether layer was separated, washed twice with water, brine, dried over $Na_2SO_4$ and concentrated on rotavapor to afford (4S)-4-fluorophenoxy-methyl)-γ-butyrolactone 6, yield 1.40 g (90%), m.p. 58–59° C., $[\alpha]_D$+23° (c 1.99, $CHCl_3$), e.e. 92%. $^1H$ NMR (200 MHz, $CDCl_3$): δ2.13–2.80 (m, 4 (dd, 1 H, J=4.5, 9.0 Hz), 4.11 (dd, 1 H, J=4.5, 9.0 Hz), 4.80 (m, 1 H), 6.75=7.02 (m, 4 H).

Part 4: (2S)-(4-Fluorophenoxymethyl)-5-hydroxytetrahydrofuran (Scheme I; 7)

A flame dried 100 mL two neck round bottom flask equipped with a magnetic stir bar and nitrogen inlet was charged with a solution of 3.5 g (0.0167 mol) of (4S)-4-fluorophenoxy-methyl)-γ-butyrolactone 6 in 30 mL of $CH_2Cl_2$. That solution was cooled to −78° C. and 7.34 mL (0.018 mol) diisobutylaluminum hydride (DIBAL-H; 2.5M solution in hexane) was added dropwise. The reaction mixture was stirred at −78° C. for 3 hours. The reaction mixture was quenched with methanol (5 mL) and saturated aqueous solution of potassium sodium tartrate. The organic layer was separated, dried over $Na_2SO_4$ and concentrated on rotavapor to provide (2S)-(4-fluorophenoxymethyl)-5-hydroxytetrahydrofuran 7 as a solid (3.47 g). This crude lactol was used in the next reaction (Part 5) without further purification.

Part 5: (2S) (4fluoophenoxymethyl)-5-(tert-butyldimethylsiloxy)-tetrahydrofuran) (Scheme II; 8)

A solution of 3.47 g of (2S)-(4-fluorophenoxymethyl)-5-hydroxytetrahydrofuran 7 in 30 mL of $CH_2Cl_2$ was taken in an 100 mL round bottom flask equipped with a magnetic stir bar and nitrogen inlet. That solution was cooled in an ice-water bath and 2.18 g (0.032 mol) of imidazole was added, followed by a solution of 3.6 g (0.024 mol) of tert-butyldimethylsilylchloride (TBDMSCl) in 30 mL of $CH_2Cl_2$. The reaction mixture then was stirred at room temperature for 3 hours, and the reaction then quenched with ice water, the organic layer separated, dried over $Na_2SO_4$ ana concentrated under reduced pressure. The residue was purified by column chromatography using light petroleum ether:ethyl acetate (9:1) to yield (2S) (4-fluoophenoxymethyl)-5-(tert-butyldimethylsiloxy)-tetrahydrofuran) 8 as an oil (5.1 g, 95%). $^1H$ NMR (200 MHz, $CDCl_3$): δ 0.09 (s, 6 H), 0.88 (s, 9 H), 1.72–2.34 (m, 4 H), 3.76=4.08 (m, 2 H), 4.28–4.54 (m, 1 H), 5.47 (s, ⅓ H), 5.54 (d, J=4.5 Hz, ⅔ H), 6.75–7.0 (m, 4H).

Part 6: (2S) (5SR) (4-fluoophenoxymethyl)-5-(1-butynyl-4-tert-butyldimethylsiloxy)-tetrahydrofuran (Scheme II; 9)

To a flame dried 100 mL two neck round bottom flack equipped with a magnetic stir bar and nitrogen inlet and septum was added a solution of 5 g (0.0154 mol) of (2S) (4-fluoophenoxymethyl)-5-(tert-butyldimethylsiloxy)-tetrahydrofuran) 8 in 25 mL of $CH_2Cl_2$. That solution was cooled to −78° C. and 2.82 mL (0.0184 mol) of trimethyl-silylbromide (TMSBr) was added dropwise. The reaction mixture was then stirred at −78° C. for 3 hours.

In a separate flame dried 50 mL two neck round bottom flask equipped with a magnetic stir bar, nitrogen inlet and septum was added a solution of 3.4 g (0.0184 mol) of 4-tert-butyl-dimethylsiloxy-1-butyne in 30 mL of THF. That solution was cooled to −78° C. and 15.4 mL (1.5M solution in hexane; 0.023 mol) of n-BuLi was added dropwise. That reaction mixture was stirred at −78° C. for 1 hour, and then transferred via syringe to the TMSBr solution. The combined solutions were stirred at −78° C. for 2 hours, and then the reaction quenched with saturated ammonium chloride solution (20 mL) and the organic layer separated. The aqueous layer was extracted with $CH_2Cl_2$ and the combined organic layers were dried over $Na_2SO_4$ and then concentrated under reduced pressure to afford (2S) (5SR) (4-fluoophenoxymethyl)-5-(1-butynyl-4-tert-butyldimethylsiloxy)-tetrahydrofuran 9 as a thick syrup (6.0 g; 97%).

Part 7: (2S) (5RS)-2-(4-Fluorophenoxymethyl)-5-(4-hydroxybutyn-1-yl)-tetrahydrofuran (Scheme II; 10)

Without further purification, (2S) (5SR) (4-fluoophenoxymethyl)-5-(1-butynyl-4-tert-butyldimethylsiloxy)-tetrahydrofuran 9 as prepared in Part 6 above was dissolved in 25 mL of methanol in a 50 mL single neck round bottom flask. That methanol solution was cooled in an ice-water bath and 3 mL of 1% HCl solution in methanol was added. The reaction mixture was then stirred at room temperature for 3 hours, followed by neutralization with saturated aqueous sodium bicarbonate solution. After removal of methanol under reduced pressure, the resulting residue was dissolved in 100 mL of ethyl acetate. The organic layer was washed with water and brine, dried over $Na_2SO_4$ and concentrated under reduced pressure. The residue was purified by column chromatography using light petroleum ether:ethyl acetate (1:1) to provide (2S) (5RS)-2-(4-fluorophenoxymethyl)-5-(4-hydroxybutyn-1-yl)-tetrahydrofuran 10 as a thick syrup (4.0 g, 96%). $^1H$ NMR (200 MHz, $CDCl_3$): δ 1.76–2.32 (m, 4 H), 2.46 (dt, 2 H, J−6.7 Hz), 3.69 (t, 2 H, J=6.7 Hz), 3.89 (d, 2 H, J=4.5 Hz), 4.41 (m, 1 H), 4.70 (m, 1 H), 6.73–6.98 (m, 4 H).

EXAMPLE 2

Alternate preparation of (2S) (5RS)-2-(4-fluorophenoxymethyl)-5-(4-hydroxybutyn-1-yl)-tetrahydrofuran (Scheme III; 10)

Part 1: (2S) (5RS)-5-O-acetyl-2-(4-fluoro-phenoxymethyl) tetrahydrofuran (Scheme III; 11)

To a 25 ml round bottom flask with magnetic stir bar, (2S) (5RS)-2-(4-fluorophenoxymethyl)-5-hydroxy tetrahydrofuran 7 (1.0 g, 0.0047 mol) in $CH_2Cl_2$ (5 mL) was added. The solution was cooled in an ice-bath, pyridine (0.8 mL), acetic anhydride (0.9 mL) and DMAP (catalytic amount) were added in succession. The reaction was monitored by TLC (EtOAc-light petroleum ether 1:3, Rf=0.5). The reaction mixture was diluted with $CH_2Cl_2$ (10 mL) washed with 5% HCl, brine and dried over $Na_2SO_4$. The solvent was removed on rotavapor to give (2S) (5RS)-5-O-acetyl-2-(4-fluoro-phenoxymethyl) tetrahydrofuran 11 (1.05 g, 88%). $^1H$ NMR (200 MHz, $CDCl_3$): δ 1.98, 2.05 (2s, 3 H), 1.89–2.3 (m, 4 H), 3.85–4.09 (m, 2 H), 4.36–4.61 (m, 1 H), 6.26 (s, ½ H), 6.33 (d, J=4.5 Hz, ½ H), 6.75–7.01 (m, 4 H).

Part 2: (2S) (5SR) (4-fluorophenoxymethyl)-5-(1-butynyl-4-tert-butyldimethylsiloxy)-tetrahydrofuran (Scheme III; 9)

To a flame dried 25 ml two-necked round bottom flask equipped with magnetic stir bar, nitrogen inlet and a septum, was added a solution of (2S) (5RS)-2-(4-fluorophenoxy-methyl)-5-O-acetyl tetrahydrofuran 11 (1.05 g, 0.004 mol) in $CH_2Cl_2$ (12 mL). The solution was cooled to 78° C. and TMS-Br (0.65 ml, 0.0049 mol) was added dropwise. The reaction mixture was stirred at −78° C. for 3 hours (monitored by TLC, EtOAc-light petroleum 1:4, Rf=0.4). In a separate flame dried 50 mL two-necked round bottom flask equipped with magnetic stir bar, nitrogen inlet and a septum, a solution of 4-tert-butyldimethylsiloxy-1-butyne (0.913 g, 0.0049 mol) in THF (15 mL) was taken. The solution was cooled to −78° C. and n-BuLi in hexane (1.5M, 4.13 mL, 0.0062 mol) was added dropwise. The reaction mixture was stirred at −78° C. for 1 hour. This solution was transferred via cannula to the reaction mixture of step 3 at −78° C. The reaction was monitored by TLC (EtOAc-light petroleum 1:4, Rf=0.7) and completed in 2 hours. The reaction mixture was quenched with saturated ammonium chloride solution (10 mL). THF was removed under reduced pressure and extracted with $CH_2Cl_2$ (2×10 mL) dried over $Na_2SO_4$ and concentrated, to provide a crude yield of 1.7 g of (2S) (5SR) (4-fluoophenoxymethyl)-5-(1-butynyl-4-tert-butyldimethylsiloxy)-tetrahydrofuran 9.

Part 3: (2S) (5RS)-2-(4-Fluorophenoxymethyl)-5-(4-hydroxybutyn-1-yl)-tetrahydrofuran (Scheme III; 10)

The crude product 9 (1.7 g) as prepared in Part 2 above was dissolved in methanol (10 mL), and 1% HCl solution in methanol (5 mL) was added. After 3 h the reaction mixture was neutralized with saturated aqueous sodium bicarbonate. After removal of methanol on rotavapor, the residue was dissolved in ethyl acetate (15 mL). The EtOAc fraction was washed with water, brine, dried over $Na_2SO_4$ and concentrated on rotavapor. The residue afforded (2S) (5Rs)-2-(4-fluorophenoxymethyl)-5-(4-hydroxybutyn-1-yl)-tetrahydrofuran 10 as a thick syrup (0.957 g, 88%).

EXAMPLE 3

Further alternate preparation of (2S) (5RS)-2-(4-fluorophenoxymethyl)-5-(4-hydroxybutyn-1-yl)-tetrahydrofuran (Scheme IV; 10)

Part 1: (2S) (5RS)-5-bromo-2-(4-fluorophenoxymethyl) tetrahydrofuran (Scheme IV; 12)

(2S) (5RS)-5-bromo-2-(4-fluorophenoxymethyl) tetrahydrofuran was prepared from (2S) (5RS)-5-O-acetyl-2-(4-fluorophenoxymethyl)tetrahydrofuran 11 (1.06 g, 0.00417 mol) and TMS-Br (0.65 mL, 0.0049 mol).

Part 2: (2S) (5RS)-2-(4-fluorophenoxymethyl)-5-(4-tetrahydropyranoyloxybutyn-1-yl)-tetrahydrofuran (Scheme IV; 13)

In a flame dried 50 mL two-necked RB flask equipped with a magnetic stir bar, nitrogen inlet and a septum 4-tetrahydropyranoyl-1-butyne (0.774 g, 0.005 mol) in THF (10 mL) was taken and cooled to −78° C. A solution of n-BuLi in hexane (1.5 M, 4.2 mL, 0.0063 mol) was added dropwise, and the reaction mixture was stirred at −78° C. for 1 hour. This solution was transferred via cannula to the reaction mixture of art 1 of this example at −78° C. That reaction mixture was stirred at −78° C. for 2 h and monitored by TLC (EtOAc-light petroleum 1:4, Rf=0.7). The reaction mixture was quenched with saturated ammonium chloride solution and THF was removed on rotavapor. The residue was partitioned between $CH_2Cl_2$ (20 mL) and water, and the organic layer was separated, washed with water, brine dried over $Na_2SO_4$ and concentrated on rotavapor to provide a crude yield of 1.73 g.

Part 3: (2S) (5RS)-2-(4-fluorophenoxymethyl)-5-(4-hydroxybutyn-1-yl)-tetrahydrofuran (Scheme IV; 10)

That crude product 13 (1.73 g) was dissolved in MeOH (10 mL) and 1% HCl in methanol (5 mL) was added. After 2.5 h, the reaction mixture was quenched by saturated aqueous $NaHCO_3$, and concentrated under reduced pressure. The residue was dissolved in EtOAc (20 mL), washed with water, brine, dried over $Na_2SO_4$ and concentrated to give (2S) (5RS)-2-(4-fluorophenoxymethyl)-5-(4-hydroxybutyn-1-yl)-tetrahydrofuran 10 (1.03 g, 93%). HPLC analysis: Column ODS; flowrate: 1.0 mL/min.; UV: 225 nm. Mobile phase 60% methanol in water. Trans:cis ratio (65:35).

EXAMPLE 4

Further alternate preparation of (2S)(5RS)-2-(4-fluorophenoxymethyl)-5-(4-hydroxybutyn-1-yl)-tetrahydrofuran (Scheme V: 10)

Part 1: (2S) (5RS)-5-benzenesulfonyl-2-(4-fluorophenoxymethyl)tetrahydrofuran (Scheme V; 14)

To benzenesulfonic acid sodium salt (10.0 g, 0.061 mol), 25% HCl was added dropwise with stirring until the solid dissolved. The reaction mixture was extracted (100 mL each, 3 times) with EtOAc, dried over $Na_2SO_4$ and concentrated to give benzenesulfonic acid (7.8 g, 90%). To a 100 mL round bottom with a magnetic stir bar, benzenesulfonic acid (4.61 g, 0.0324 mol), $CaCl_2$(3.6 g, 0.0324 mol) and dry dichloromethane (30 mL) were added. The reaction mixture was cooled to 0° C. and (2S) (5RS)-2-(4-fluorophenoxymethyl)-5-hydroxy-tetrahydrofuran (4.6 g, 0.0216 mol) in dry $CH_2Cl_2$ (20 mL) was added. The reaction mixture was stirred for 3 h and monitored by TLC (EtOAc-light petroleum ether 1:4, Rf=0.25). The reaction mixture was filtered through celite and washed with $CH_2Cl_2$ (3 times). The combined organic layer was washed with saturated aqueous $Na_2CO_3$, water brine and dried over $Na_2SO_4$. Solvent was removed under reduced pressure to afford the crude (2S) (5RS)-5-benzenesulfonyl-2-(4-fluorophenoxymethyl)tetrahydrofuran 14 which was crystallized from chloroform-hexane to give pure white solid, yield 6.8 g (93%), m.p. 102° C.–104° C. $^1$H NMR (200 MHz, $CDCl_3$): δ 1.90–3.0 (m, 4 H), 3.85–5.0 (m, 4 H), 6.70–7.05 (m, 4 H), 7.45–7.72 (m, 3 H), 7.77–8.0 (m, 2 H).

Part 2: (2S) (5RS)-2-(4-fluorophenoxymethyl)-5-(4-tetrahydropyranoyl-1-butyne)-tetrahydrofuran (Scheme V; 9)

To a 250 ml two-necked RB flask equipped with magnetic stir bar, nitrogen inlet and a septum, Grignard grade magnesium (2.0 g, 0.0833 mol) was taken and the flask flame dried along with magnesium. The flask was cooled to room temperature and dry THF (5 mL) was added followed by 1,2-dibromoethane (catalytic amount) to activate the magnesium. Isopropylbromide (8.78 g, 0.0714 mol) in THF (140 mL) as added dropwise over 15 min. The reaction mixture was stirred for 1 hour. The isopropyl magnesium bromide was cannulated in a 1000 mL flame dried two-necked round bottom flask with spin-bar, nitrogen inlet and septum. 4-Tetrahydropyranoyl-1-butyne (11.0 g, 0.0714 mol) in THF (140 mL) was added. The reaction mixture was stirred for 30 min. and cooled at 0° C. Freshly prepared $ZnBr_2$ solution (1M, 43 mL, 0.0428 mol) in THF was introduced. After 45 min. at room temperature (2S) (5RS)-5-benzenesulfonyl-2-(4-fluorophenoxymethyl)tetrahydrofuran (12.0 g, 0.0357 mol) in THF (70 mL) was added at room temperature and stirred for 3 h. (TLC, EtOAc-light petroleum 1:4, Rf=0.7).

Saturated aqueous NH$_4$Cl solution was added at 0° C. to quench the reaction. THF was removed on rotavapor and the reaction mixture was partitioned between water and EtOAc. The EtOAc layer was washed with water, brine, dried over Na$_2$SO$_4$ and concentrated to provide (2S) (5RS)-2-(4-fluorophenoxymethyl)-5-(4-tetrahydropyranoyl-1-butyne)-tetrahydrofuran 9, crude yield 18.9 g.

Part 3: (2S)(5RS)-2-(4fluorophenoxy-methyl)-5-(4-hydroxybutyn-1-yl)tetrahydrofuran (Scheme V; 10)

That crude product 9 (18.9 g) was dissolved in methanol (60 mL) in 100 mL round bottom flask fitted with magnetic stirring arrangement. 1% HCl in methanol (25 mL) was introduced, and the reaction mixture was stirred at room temperature for 2 hours (TLC, EtOAc-light petroleum ether 1:1, Rf=0.4). The reaction mixture was neutralized by saturated aqueous Na$_2$CO$_3$ solution and then concentrated under reduced pressure. The residue was extracted with ethyl acetate, washed with water, brine, dried over Na$_2$SO$_4$ and concentrated on rotavapor. The residue was dried under vacuum on hot water bath to give (2S) (5RS)-2-(4-fluorophenoxy-methyl)-5-(4-hydroxybutyn-1-yl)tetrahydrofuran 10 yield 10.9 g. HPLC analysis: Column ODS; flowrate: 1.0 mL/min.; UV: 225 nm. Mobile phase 60% methanol in water. Trans:cis ratio (69:31). That crude product of 10 was crystallized (2 times) from ether-light petroleum ether by seeding to yield the pure product (3.3 g, 35%), m.p. 76° C. [α]$_D$–34.26° (c 1.36, CHCl$_3$). HPLC purity above 95%.

EXAMPLE 5

Further preparation of (4S)-4-fluorophenoxy-methyl)-γ-butyrolactone (Scheme VI; 6)

Part 1: Trimethylene D-mannitol (Scheme VI; 16)

D-mannitol (2.0 kg, 10.98 mol) (Scheme VII; 15) formaldehyde solution (35% by weight, 4.4 lit, 51.2 mmol) and conc. HCl (4.0 lit.) were taken in a 10 lit. flask with mechanical stirring arrangement. The reaction mixture was kept at room temperature for 72 hours. The solid was filtered, washed with water and dried to provide 2.2 kg (91.9%) of trimethylene D-mannitol 16, m.p. 228°–230°, [α]$_D$–108° (c 2.0, CHCl$_3$), TLC (silica gel), 1:2, ethyl acetate: hexane, Rf=0.4. $^1$H NMR (CDCl$_3$): δ 3.4–3.75 (m, 6H), 4.18 (dd, J=4.0, 8.0 Hz), 4.59 (d, 2H, J–4.0 Hz), 4.76 (s, 2H), 5.05 (d, 2H, J=4.0 Hz).

Part 2: 1,3,4,6-Tetra-O-acetyl-2,5-O-methylene-D-mannitol (Scheme VI; 17)

Ice cold acetylating mixture (10.1 lit.) prepared from 7.0 liters of acetic anhydride, 3.0 liters of acetic acid and 0.1 liters of concentrated H$_2$SO$_4$ was taken in 20 lit. round bottom flask with mechanical stirring arrangement. Trimethylene D-mannitol 16 (2.2 kg, 10.1 mol) was slowly added in portions (45 min.–1 hour). After 3 h the reaction mixture was poured over ice-water with vigorous stirring (50–60 lit.). The solid was filtered, washed with water and dried to provide 2.8 kg (78%) of 17, m.p. 126°–128°, [α]$_D$+57.8° (c 3.6, CHCl$_3$); TLC (silica gel), 2:1, ethyl acetate: hexane, Rf=0.5.

Part 3: 2,5-O-methylene-D-mannitol (Scheme VI; 18)

1,3,4,6-Tetra-Q-acetyl-2,5-O-methylene-D-mannitol 17 (2.8 kg, 7.73 mol) was added to chloroform (14 lit.) in 25 lit. round bottom flask with mechanical stirring. The reaction mixture was cooled to 0° C., and 0.5% NaOMe solution (6.5 lit.) was added slowly. The reaction mixture was stirred for 3 hours. The solid was filtered and dried to provide 1.0 kg (67%) of 2,5-O-methylene-D-mannitol 18, m.p. 172°–173° C., [α]$_D$–52° (c 1.18, CHCl$_3$), TLC (silica gel), 1:4, methanol: chloroform, Rf=0.8. $^1$H NMR (D$_2$O): δ 3.42 (m, 2H), 3.72 (m, 4 H), 3.97 (m, 2 H), 4.91 (s, 2 H).

Part 4: 1,6-Di-O-tosyl-2,5-O-methylene-D-mannitol (Scheme VI; 19)

2,5-O-methylene-D-mannitol 18 (200 g, 1.03 mol) was dissolved in pyridine (1.2 lit.) in 3 liter two neck R B flask fitted with an addition funnel and mechanical stirring arrangement. The reaction mixture was cooled to 0° C., tosyl chloride (430.9 g, 2.26 mol) dissolved in pyridine (0.8 lit.) was added slowly, and the reaction mixture was stirred at room temperature for 12 h. Pyridine then was removed on rotavapour under vacuo. The thick slurry was poured over ice-water (10 lit) with mechanical stirring. After 2 hours the solid was filtered, washed with water, dried (yield, 400 g crude) and crystallized from methanol to provide 260 g of product 19, m.p. 142° C., [α]$_D$–23.39° (c 1.7, MeCOMe), TLC (silica gel), 4:1, ethyl acetate: hexane, Rf=0.4. $^1$H NMR (CD$_3$COCD$_3$): δ 2.45 (s, 6H), 2.85 (s, 2 H), 3.27 (m, 2 H), 3.65 (m, 2 H), 4.12 (dd, 2 H, J–6.2, 10.0 Hz), 4.45 (m, 2 H), 4.46 (s, 2 H), 7.38, 7.63 (Abq, 8 H, J=8.0 Hz).

Part 5: 3,4-O-Ethoxymetyhlene-2,5-O-methylene-1-6-di-O-tosyl-D-mannitol (Scheme VI, 20)

2,5-O-methylene-1,6-di-O-tosyl-D-mannitol 19, (185 g, 0.368 mol) triethylorthoformate (613 mL) and PTSA (100 mg) were stirred in a 1 lit. round bottom flask fitted with mechanical stirring arrangement at room temperature. After 3 hours of stirring potassium carbonate was added to neutralize PTSA. Solid was filtered and filtrate concentrated under reduced pressure and dried under vacuo to provide 206 g (100%) of product 20, m.p. 87–88° C., [α]$_D$+46.02° (c 0.93, CHCl$_3$), TLC (silica gel) 7.3 hexane:EtOAc, Rf=0.4. $^1$H NMR (CDCl$_3$): δ 1.21 (t, 3 H, J=7.6 Hz), 2.45 (s, 6 H), 3.55 (q, 2 H, J=7.6 Hz), 3.7–3.85 (m, 2 H), 3.97 (t, 1 H, J=8.5 Hz), 4.08–4.31 (m, 5 H), 4.74 (s, 2 H), 5.76 (s, 1 H), 7.34, 7.77 (ABq, 8 H, J=8.5 Hz).

Part 6: 3,4-O-ethoxymethylene-1,6-di-O-p-fluorophenyl-2,5-O-methylene-D-mannitol (Scheme VI: 21)

4-Fluorophenol 2 (124 g, 1.107 mol) was dissolved in CH$_3$CN (250 mL) and then KOH solution (62 g, in 45 mL, H$_2$O, 1.107 mol) was added. The reaction mixture was stirred for 15 minutes. 3,4-O-Ethoxymetyhylene-2,5-O-methylene-1-6-di-O-tosyl-D-mannitol 20 (206 g, 0.369 mol) (used as prepared in Part 5 above without further purification) in CH$_3$CN (400 mL) was separately taken in 1 liter two neck round bottom flask fitted with reflux condenser, guard tube and mechanical stirring arrangement. To this solution the potassium salt of 4-fluorophenol was added at room temperature. The reaction mixture was heated under reflux for 6 hours and monitored by TLC (silica gel, 3:7, ethyl acetate:hexane, Rf=0.7). The reaction mixture was cooled in ice-water and solid was filtered washed with ethyl acetate (100 mL), and the combined filtrate was concentrated under reduced pressure. The resulting residue was dissolved in ethyl acetate (800 mL) and the organic layer was washed with 2M NaOH (4×100 mL), water and brine dried over Na$_2$SO$_4$. Concentration under reduced pressure afforded 3,4-O-ethoxymethylene-1,6-di-O-p-fluorophenyl-2,5-O-methylene-D-mannitol 21 (147 g, 90.9%). $^1$H NMR (CDCl$_3$): δ 1.3 (t, 3 H, J=6.25 Hz), 3.70 (q, 2 H, J=6.25 Hz), 4.0–4.45 (m, 7 H), 4.56 (t, 1 H, J=9.6 Hz), 5.19 (s, 2 H), 5.97 (s, 1 H), 6.89–7.10 (m, 8 H).

Part 7: 1,6-Di-O-p-fluorophenyl-2,5-O-methylene-D-mannitol (Scheme VI: 22)

3,4-O-Ethoxymethylene-1,6-di-O-p-fluorophenyl-2,5-O-methylene-D-mannitol 21 (145 g 0.331 mol), tetrahydrofuran (350 mL) and 0.1% aqueous HCl (40 mL) were mixed in a 1 lit two neck round bottom flask fitted with mechanical stirring arrangement at 0° C. The reaction mixture was allowed to attain room temperature and further stirred for 6 hours and monitored by TLC (silica gel, 1:1, ethyl acetate:hexane, Rf=0.3). The reaction mixture was basified to pH 8 by saturated NaHCO$_3$ solution, and the solid was filtered and the filtrate concentrated to dryness to provide 125 kg (99%) of product 22, m.p. 126–127° C., [α]$_D$ –34.49° (c 1.148, MeCOMe). $^1$H NMR (CDCl$_3$): δ 2.7 (s, 2 H), 3.72 (m, 2 H), 3.90 (m, 2 H), 4.12 (m, 4 H), 4.87 (s, 2 H), 6.77–7.0 (m, 8 H).

Part 8: 4,4'-methylenedioxy-bis[(R)ethyl, (E)-2-ene-5-p-fluorophenoxy-pentanoate] (Scheme VI: 23)

In a 250 ml two neck round bottom flask equipped with magnetic stirring arrangement and fitted with a guard tube was taken a solution of 1,6-di-O-p-fluorophenyl-2,5-O-methylene-D-mannitol 22 (10.0 g, 0.026 mol) in CH$_2$Cl$_2$ (100 ml). The solution was cooled to 0° C. and Pb(OAc)$_4$ (12.8 g, 0.0288 mol) was added in portions. After 3 hours, ethylene glycol (1 ml) was added to quench excess Pb(OAc)$_4$. The reaction mixture was filtered over celite, and the filtrate was washed successively with water and brine. The organic layer was dried over Na$_2$SO$_4$ and concentrated under reduced pressure to afford the di-aldehyde as a thick syrup. That crude dialdehyde was taken in CH$_2$Cl$_2$ (100 ml) in 250 ml two necked round bottom flask with magnetic stirring arrangement and fitted with a nitrogen inlet. Carboethoxymethylenetriphenyl phosphorane (27.3 g, 0.0785 mol) was added in portions. The reaction mixture then was stirred for 3 hours, concentrated and purified on silica gel chromatography with 85:15 hexane:ethyl acetate as the eluent. The isolated fractions on concentration under reduced pressure yielded 4,4'-methylenedioxy-bis[ethyl, (E)-2-ene-5-p-fluorophenoxypentanoate] 23 (10.0 g, 74%) as an oil. $^1$H NMR (CDCl$_3$): δ 1.24–1.40 (m, 6 H), 3.86–4.30 (m, 8 H), 4.70 (m, 1 H), 4.84 (s, 2 H), 5.70 (brs, 1 H), 5.9–6.32 (m, 4 H), 6.76–7.02 (m, 8 H).

Part 9: 4S-(4-Fluorophenoxymethyl)-γ-butyrolactone (Scheme VI: 6)

A solution of 4,4'-methylenedioxy-bis[(R)ethyl, (E)-2-ene-5-p-fluorophenoxypentanoate] 23 (10.0 g, 0.0192 mol) in methanol (10 ml) was taken in a 200 ml parr hydrogenation flask. Pd/C (500 mg) was added to that solution and the mixture shaken in a parr apparatus at 40–50 psi for 6 hour and monitored by TLC. The reaction mixture was filtered over celite and the filtrate concentrated to afford 4,4'-methylenedioxy-bis[(R) ethyl, 5-p-fluorophenoxypentanoate] as an oil (10.0 g, 100%).

A 250 ml round bottom flask equipped with magnetic stirring arrangement and fitted with a reflux condenser was then charged with 4,4'-methylenedioxy-bis [®methyl, 5-p-fluorophenoxypentanoate] (10.0 g, 0.019 mol) in ethanol (60 ml). To that solution 10% aqueous solution H$_2$SO$_4$ (15 ml) was added. The mixture was heated under reflux for 10–12 hours and monitored by TLC, silica gel, 1:1, ethyl acetate:hexane, Rf=0.25. The reaction was cooled to 0° C. and neutralized with saturated sodium bicarbonate solution. The reaction mixture was concentrated on a rotavapour to dryness and redissolved in ethyl acetate (100 ml). The organic layer was washed with water and brine dried over Na$_2$SO$_4$ and concentrated. The residue was purified by column chromatography to afford off white crystalline solid of 4S-(4-fluorophenoxymethyl)-γ-butyrolactone 6 (7.0 g, 87%),. m.p 60–61° C., [α]$_D$+25° (c 2.18, CHCl$_3$). $^1$H NMR (CDCl$_3$): δ 2.13–2.80 (m, 4 H), 4.02 (dd, 1 H, J=4.5, 9.0 Hz), 4.11 (dd, 1 H, J=4.5, 9.0 Hz), 4.80 (m, 1 H), 6.75–7.02 (m, 4 H).

EXAMPLE 6

Further alternate preparation of (2S) (5RS)-2-(4-Fluorophenoxymethyl)-5-(4-hydroxybutyn-1-yl)-tetrahydrofuran (Scheme VII; 10)

Part 1: (±)-1,2-Epoxy-(4-fluoro)phenoxy propane (Scheme VII; 25)

p-Fluorophenol 2 (5 g, 44.6 mmol) and epichlorohydrin 24 (16.5 g, 178.4 mmol 13) were admixed in anhydrous acetone (100 ml). Anhydrous K$_2$CO$_3$ (24.0 g, 178.4 mmol) was added in 10 minutes and the reaction mixture was heated at reflux for 18 hours until the complete consumption of p-fluorophenol as monitored by TLC (4:1 hexane:ether). The reaction mixture then was filtered off, the filtrate was concentrated under vacuo to afford a light yellow oil, excess epichlorohydrin was distilled off, the residue was subjected to column chromatography on silica gel (2:8, ethyl acetate-hexane) to afford (±)-1,2-epoxy-(4-fluoro)phenoxy propane 25 in quantitative yield (8.5 g).

Part 2: (2R)-3-(4-fluoro)phenoxy-propane-1,2-diol (Scheme VII; 26)

(2R)-3-(4-fluoro)phenoxy-propane1,2-diol 26 was prepared using Jacobsen's catalyst as generally described in E. Jacobsen, Science, 277:936–938 (1997). More specifically (±)-1,2-epoxy-3-(4-fluorophenoxy propane 25 (10 g, 59.5 mmol) and (R,R)-Jacobsen's catalyst (215 mg, 0.29 mmol) were taken in a 50 ml round bottom flask and cooled to 0° C. Water (0.6 ml, 32.7 mmol) was then added dropwise for 1 hour and stirred for 5 hours at room temperature, monitored by TLC (1:1 ethyl acetate:hexane). Ethyl acetate (50 ml) was added, followed by anhydrous Na$_2$SO$_4$ (200 mg), stirred for 10 minutes filtered, concentrated to afford dark colored residue of a mixture of 26 and 27, which on column chromatography gave isolated epoxide 27 (4.36 g, 43%, 1:9 ethyl acetate-hexane) and (2R)-3-(4-fluorophenoxy-propane-1,2-diol 26 (5.06 g, 46%, 1:1 ethyl acetate-hexane).

Part 3: (2S)-3-(4-fluoro)phenoxy-1-tosyloxy-propan-2-ol (Scheme VII; 28)

A mixture of (2R)-3-(4-fluoro)phenoxy-propan-1,2-diol 26 (5.0 g, 26.8 mmol) and pyridine (4.5 ml) in CH$_2$Cl$_2$ (60 ml) were cooled to 0° C., and then p-toluenesulphonyl chloride (5.0 g, 26.8 mmol) was added portionwise to the cooled mixture. The mixture was stirred at room temperature overnight (TLC 2:3, ethyl acetate-hexane). The solvent was then removed by codistillation with toluene, and the resulting residue purified by silica gel column chromatography (2:3, ethyl acetate-hexane) to afford the product 28 (7.7 g, 85%).

Part 4: (2R)-1,2-epoxy-3-(4-fluoro)phenoxypropane (Scheme VII; 4)

(2R)-(4-Fluoro)phenoxy-1-tosyloxy-propan-2-ol 28 (5.0 g, 14.7 mmol) in a solvent mixture of THF and DMF (100 ml, 4:1) was cooled to 0° C. and NaH (0.75 g, 19.2 mmol) was added portionwise, followed by stirring of the reaction mixture for 1 hour at room temperature with monitoring of the reaction by TLC (20% ethyl acetate in hexane). The THF was removed and the residue was taken in ethyl ether (50 ml). That ether solution was washed successively with water (3×50 ml), brine (1×50 ml) dried ($Na_2SO_4$) and concentrated to afford (2R)-1,2-epoxy-3-(4-fluoro)phenoxypropane 4 as a colorless oil (2.53 g, 95%).

Part 5: (2R)-1-(4fluoro)phenoxyhex-5-en-2-ol (Scheme VII; 29)

Magnesium (0.89 g, 36.6 mmol) and iodine (catalytic amount) were taken in a 50 ml 2-neck round bottom flask provided with a reflux condenser and a septum, under $N_2$ atmosphere. A solution of allyl bromide (3.0 g, 24.4 mmol) in 10 ml of ethyl ether was slowly added and stirred for 30 minutes at room temperature. Cuprous cyanide (22 mg) then was added, and the color of the reaction mixture became dark brown. The reaction mixture was cooled to −22° C. ($CCl_4$/dry ice bath), and (2R)-1,2-epoxy-3-(4-fluoro) phenoxypropane 4 (2.05 g, 12.2 mmol) in 25 ml of ethyl ether was added. The reaction was completed within 30 minutes, as determined by TLC (benzene). Saturated aqueous ammonium chloride (4 ml) then was added and the mixture stirred for 30 minutes. Inorganic material was filtered and washed with ethyl ether (25 ml). The ether layer was dried (sodium sulphate) concentrated to give a colorless oil of (2R)-1-(4-fluoro)phenoxyhex-5-en-2-ol 29 (2.3 g, 90%).

Part 6: (2R)-2-benzenesulfonyloxy-1-(4-fluoro)-phenoxy-5-hexane (Scheme VII; 30)

(2R)-(4-Fluoro)phenoxyhex-5-en-2-ol, 29 (7.4 g, 35.2 mmol), triethylamine (10 ml) and 4-N,N'-dimethylaminopyridine (DMAP, 0.43 g, catalytic) were dissolved in 50 ml of dry $CH_2Cl_2$ and cooled in ice bath while stirring. Benzenesulfonyl chloride (5 ml, 38.7 mmol) in $CH_2Cl_2$ (10 ml) was then added dropwise to the mixture. The reaction mixture was stirred at room temperature for 6 hours and monitored by TLC (benzene)]. Solvent then was removed and the residue was poured onto a short silica gel column and eluted with 1:4 ethyl acetate-hexane to afford (2R)-2-benzenesulfonyloxy-1-(4-fluoro)-phenoxy-5-hexane 30 as a colorless oil (11.3 g, 92%).

Part 7: (6R,2E)ethyl-6-benzenesulfonyloxy-7-(4-fluoro)-phenoxy-hept-2-en-1-oate (Scheme VII; 31)

(2R)-2-Benzenesulfonyloxy-1-(4-fluoro)-phenoxy-5-hexane 30 (11.3 g, 32.5 mmol 19) in 30 ml of dry $CH_2Cl_2$ was cooled to −78° C. $O_3$ then was bubbled through the mixture until the blue color persisted (30 minutes). A stream of $N_2$ then was purged for 5 minutes through the mixture to remove excess of ozone. Dimethylsulfide (13.9 ml, 325 mmol) was added and stirred for 2 hours. The reaction mixture was washed with water (2×25 ml), brine (1×30 ml) and concentrated to afford the crude product (10.8 g, 95%). (2R)-Benzenesulfonyloxy-1-(4-fluoro)-phenoxy-5-pentanal (10.5 g, 30 mmol) was added and heated at reflux for 5 hours. Ethoxycarbonylmethylene triphenylphosphorane (11.5 g, 33 mmol) was added and heated at reflux for 5 hours. Completion of the reaction was checked by TLC (1:10, EtOAc-benzene) and the solvent was removed, the residue was purified by column chromatography on silica gel (1:3, ethyl acetate-hexane) to afford (6R,2E)-ethyl-6-benzenesulfonyloxy-7-(4-fluoro)-phenoxy-hept-2-en-1-oate 31 (8.8 g, 70%) as a colorless oil.

Part 8: (6R,2E)ethyl-6-benzenesulfonyloxy-7-(4-fluoro)-phenoxy-hept-2-en-1-ol (Scheme VII; 32)

(6R,2E)-Ethyl-6-benzenesulfonyloxy-7-(4-fluoro)-phenoxy-hept-2-en-1-oate (3 g, 7.1 mmol) 31 was dissolved in 30 ml of $CH_2Cl_2$ under $N_2$ atmosphere and cooled to −78° C. DIBAL-H (14.2 ml, 14.2 mmol, 1M solution in toluene) was added dropwise over 5 minutes and the solution was stirred at −78° C. for 45 minutes. At reaction completion as monitored by TLC (2:5, ethyl acetate-hexane), saturated aqueous ammonium chloride solution (3 ml) was added and the mixture stirred for another 30 minutes. The reaction mixture then was filtered through a celite pad the filtrate was dried over anhydrous $Na_2SO_4$ and concentrated, the residue was filtered through a short silica gel pad and concentrated to obtain (6R,2E)-ethyl-6-benzenesulfonyloxy-7-(4-fluoro)-phenoxy-hept-2-en-1-ol 32 as a solid (2.2 g, 82% yield).

Part 9: (2S,3S,6R)-6-benzenesulfonyloxy-2,3-epoxy-7-(4-fluoro)-phenoxy-7-heptan-1-ol (Scheme VII; 33)

Powdered molecular sieves 4 Å (3 g) were activated under $N_2$ atmosphere in a 25 ml 2 necked round bottom flask. $CH_2Cl_2$ (15 ml) was added followed by titanium tetraisopropoxide (1.62 ml, 5.47 mmol), (+)-diisopropyltartrate (1.07 ml, 6.56 mmol) and the mixture was cooled to −20° C. with stirring. After 5 minutes cumene-hydroperoxide (2.1 ml, 10.94 mmol, 80% solution in cumene) was added dropwise. The mixture was stirred for 15 minutes at −20° C. (6R,2E)-benzenesulfonyloxy-7-(4-fluoro)-phenoxy-hept-2-en-1-ol 32 (2.0 g, 5.47 mmol) in 10 ml of $CH_2Cl_2$ was then added and the reaction mixture was stirred for 2.5 hours at −20° C. The reaction mixture was checked for the completion by TLC (1:1, ethyl acetate-hexane), 1 ml of 10% aqueous tartaric acid solution was added at −20° C. and the reaction mixture was warmed to room temperature in 30 minutes. The reaction mixture was filtered through a celite pad dried over $Na_2SO_4$, concentrated and the residue was subjected to column chromatography on silica gel (1:1, ethyl acetate-hexane) to afford (2S,3S,6R)-6-benzenesulfonyloxy-2,3-epoxy-7-(4-fluoro)-phenoxy-7-heptan-1-ol 33 (2.4 g, 98% yield) as a solid.

Part 10: (2S,3S,6R)-6-benzenesulfonyloxy-1-chloro-2,3-epoxy-7-(4-fluoro)-phenoxy-heptane (Scheme VII; 34)

(2S,3S,6R)-6-Benzenesulfonyloxy-2,3-epoxy-7-(4-fluoro)-phenoxy-7-heptan-1-ol (2.25 g, 5.7 mmol) 33 and triphenylphosphine (1.5 g, 5.7 mmol) were dissolved in solvent mixture of $CHCl_3$ and $CCl_4$ (40 ml, 1:1) and $NaHCO_3$ (0.3 g) was added. The reaction mixture was refluxed for 3 hours and monitored by TLC (2:5, ethyl acetate-hexane). Solvent was removed, the residue was purified by column chromatography on silica gel (1:4, ethyl acetate-hexane) to afford (2S,3S,6R)-6-benzenesulfonyloxy-1-chloro-2,3-epoxy-7-(4-fluoro)-phenoxy-heptane 34 (1.5 g, 64% yield) as a solid.

Part 11: (2S,5S)-5-ethynyl-2-(4-fluoro)-phenoxymethyl-tetrahydrofuran (Scheme VII; 35)

n-BuLi (7.2 ml, 7.2 mmol) was added to a solution of freshly distilled diisopropylamine (1.12 ml, 8.6 mmol) in 6 ml of dry THF at −40° C. and stirred for 15 minutes. A solution of (2S,3S,6R)-6-benzenesulfonyloxy-1-chloro-2,3-opoxy-7-(4-fluoro)-phenoxy-heptane 34 (1.0 g, 2.42 mmol) was added in 8 ml of dry THF. The reaction mixture was stirred at −40° C. for 1 hour and then at room temperature for 1 hour. When TLC showed complete consumption of starting material the reaction was quenched at 40° C. with aqueous ammonium chloride (1 ml), THF was removed under vacuo, the residue was taken in ethyl acetate, filtered, dried over $Na_2SO_4$ and concentrated. Crude product was subjected to column chromatography on silica gel (1:9, ethyl acetate-hexane) to afford (2S,5S)-5-ethynyl-2-(4-fluoro)-phenoxymethyl-tetrahydrofuran 35 (0.32 g, 60% yield).

Part 12: Preparation of (2S,5S)-5-(2'-hydroxyethyl)-ethynyl-2-(4-fluoro)-phenoxymethyltetrahydrofuran (Scheme VII; 10)

To a solution of (2S,5S)-5-ethynyl-2-(4-fluoro)-phenoxymethyl-tetrahydrofuran 35 (0.8 g, 3.6 mmol) in 15 ml of dry THF at −78° C., n-BuLi (5 ml, 1M solution in hexane), stirred for 15 minutes. Freshly distilled $BF_3Et_2O$ (1.4 ml, 11 mmol) was added followed by ethyleneoxide (excess, THF solution). The reaction mixture was continued to stir at −78° C. until completion (30 minutes). Saturated aqueous ammonium chloride solution (1 ml) was added at −78° C. stirred for 5 minutes, warmed to room temperature, THF was removed, residue was extracted with ether (2×20 ml), combined organic layer was dried over $Na_2SO_4$, concentrated to afford a residue. That residue was purified by column chromatography on silica gel (2:5, ethyl acetate-hexane) to afford (2S,5S)-5-(2'-hydroxyethyl)-ethynyl-2-(4-fluoro)-phenoxymethyltetrahydrofuran 10 (0.87 g, 90% yield) as a white solid. That product 10 was found to be identical (NMR, optical rotation, TLC) with samples prepared by Example 1 above.

EXAMPLE 7

Preparation of (±)-2-(4-fluorophenoxymethyl)-7-(4-N-hydroxy-ureidyl-1-butynyl)-oxepane (Scheme VIII; 42)

Part 1: (±)-7-Benzyloxy-1-(fluorophenoxy)-heptane-2-ol (Scheme VIII; 42)

Magnesium (2.4 g, 98 mmol) was added to a 250 ml flask and flame dried. Dry THF, 25 ml, and 1 ml of dibromoethane were then added. 1-Bromo-4-6enzyloxy-butane 41 (12 g, 49.4 mmol) dissolved in 50 ml of dry THF was added dropwise and the reaction mixture was stirred at room temperature. After 1 hour, the reaction mixture is cooled in an ice-water bath and 90 mg of copper cyanide is added. After 10 minutes in an ice-bath, 4-fluorophenyl-glycidyl ether (5 g, 29.6 mmol) dissolved in 30 ml of dry THF is added slowly. The reaction is monitored by TLC (ethyl acetate:hexane 3:7). After 15 minutes, the reaction is quenched with saturated aqueous ammonium chloride, concentrated and partitioned between water-ethyl acetate. The ethyl acetate layer is then washed with brine, dried over $Na_2SO_4$ and concentrated to give the desired benzyloxy-heptane 42. The structure was confirmed by $^1$H-NMR.

Part 2: (±)-7-(4-Fluorophenoxy)6-(2-methoxyethoxymethoxy)-heptane-1-ol (Scheme VIII; 43)

(±)-7-Benzyloxy-1-(fluorophenoxy)-heptane-2-ol 42 (9.8 g, 29.5 mmol) in 30 ml of chloroform is added to a 100 ml round bottom flask. Diisopropylethylamine (7.6 ml, 44.3 mmol) and methoxyethoxymethyl chloride (3.7 ml, 32.5 mmol) are added and the reaction mixture is stirred for 3 hours. The mixture is then washed with water, brine, dried ($Na_2SO_4$) and concentrated. The residue was purified on silica gel (ethyl acetate:hexane 1:9) to give (±)-7-benzyloxy-1-(4-fluorophenoxy)-2-(2-methoxyethoxy-methoxy)-heptane 7-3 (11 g, 89%).

Part 3: (±)-7-(4-Fluorophenoxy)-6-(2-methoxyethoxymethoxy)heptan-1-ol (Scheme VIII; 44)

(±)-7-benzyloxy-1-(4-fluorophenoxy)-2-(2-methoxyethoxy-methoxy)-heptane 43 (11 g, 26.3 mmol) in 30 ml of ethanol is added to a 50 ml round bottom flask. Palladium on activated carbon (10% Pd/C, 150 mg) is added and the reaction mixture is stirred under an atmosphere of hydrogen. After 3 hours, the reaction mixture was filtered through celite, washed with ethanol and concentrated. The crude product was purified on silica gel (ethyl acetate:hexane 1:1) to give (±)-7-(4-fluorophenoxy)-6-(2-methoxyethoxymethoxy)heptan-1-ol 44 (7.9 g, 91%). The structure was confirmed by $^1$H-NMR.

Part 4: (±)-7-(4-Fluorophenoxy)-6-(2-methoxyethoxymethoxy)-heptan-1-al (Scheme VIII; 45)

Oxalyl chloride (2.9 ml, 33.6 mmol) is added to 25 ml of methylene chloride and cooled to −78° C. Dry dimethyl sulfoxide (4.7 ml, 67.2 mmol) is then added and the reaction is stirred at −78° C. After 45 minutes, (±)-7-(4-fluorophenoxy)-6-(2-methoxyethoxymethoxy)-heptan-1-ol 44 (3.7 g, 11.2 mmol) dissolved in $CH_2Cl_2$ is added and the reaction is stirred at −78° C. After 1 hour, the reaction is quenched with 15.7 ml of triethylamine and diluted with $CH_2Cl_2$. The reaction mixture is then washed with water, brine dried ($Na_2SO_4$) and concentrated. The crude product is purified on silica gel (ethyl acetate:hexane 1:9) to give (±)-7-(4-fluorophenoxy)-6-(2-methoxyethoxymethoxy)-heptan-1-al 45, 3.3 g, 89%.

Part 5: (±)-7-(4-fluorophenoxy)-6-(hydroxy)-heptan-al (Scheme IX; 47)

(±)-7-(4-fluorophenoxy)-6-(2-methoxyethoxymethoxy) heptan-1-al 45 (2 g, 6.1 mmol) and 2 ml of trifluoroacetic acid are added to 10 ml of chloroform. The reaction mixture is stirred for 24 hours and then is neutralized with 1% aqueous NaOH. The organic layer is washed with water, brine, dried ($Na_2SO_4$), concentrated. The crude trifluoroacetyl-aldehyde 46 is then dissolved in $MeOH:H_2O$ (1:1) and solid $K_2CO_3$ is added to maintain pH 8. The reaction is complete is approximately 15 minutes, as monitored by TLC (ethyl acetate:hexane 3:7). Methanol is removed in vacuo and remaining solution is extracted with ethyl acetate to give (±)-7-(4-fluorophenoxy)-6-(hydroxy)-heptan-al 47 (1.2 g, 82%).

Part 6: (±)-7-(Benzylsulfonyl)-(4-fluorophenopxymethyl)-oxepane (Scheme IX; 48)

Benzene sulfinic acid (0.79 g, 5.62 mmol) and $CaCl_2$ (0.62 g, 5.62 mmol) are added to 15 ml of $CH_2Cl_2$ and cooled in an ice-water bath. (±)-7-(4-Fluorophenoxy)-6-(hydroxy)heptan-1-al 4 (0.90 g, 3.75 mmol), dissolved in 5 ml of $CH_2Cl_2$, is added to the reaction mixture and stirred at room temperature. After 3 hours the reaction mixture is filtered through celite and washed with $CH_2Cl_2$. The filtrate is washed with saturated aqueous $Na_2CO_3$, water, brine, dried (Na2SO4) and concentrated. The crude product is then purified on silica gel (ethyl acetate:hexane 1:6) to give (±)-7-(benzylsulfonyl)-(4-fluorophenopxymethyl)-oxepane 48 in 80% yield (1.1 g). The structure was confirmed by $^1$H-NMR.

Part 7: (±)-2-(4-Fluorophenoxymethyl)-7-(tetrahyropyranyloxybutyn-1-yl)-oxepane (Scheme IX; 49)

Magnesium (0.1 g, 4.3 mmol) was added to a 50 ml round bottom flask and flame dried. Dry THF (10 ml) and a few drops of 1,2-dibromoethane were then added followed by isopropyl bromide (0.34 g, 2.7 mmol). The reaction was stirred for 1 hour and the resulting isopropyl magnesium bromide solution was cannulated into a 100 ml flame dried flask. 4-Tetrahydropyranoyl-1-butyne (0.34 g, 2.18 mmol) dissolved in THF was added to the reaction mixture and it was stirred. After 30 minutes, the reaction mixture was cooled in an ice-water bath and ZnBr$_2$ (1.3 ml, 1 M in THF) was added at room temperature. After 45 minutes, (±)-7-(enzensulfonyl)2-(4-fluorophenoxymethyl)-oxepane (0.4 g, 1.1 mmol) dissolved in 2 ml of THF was added. The reaction was stirred at room temperature for 30 minutes, then cooled in an ice-water bath and the reaction was quenched with saturated aqueous NH$_4$Cl. THF was removed in vacuo and the reaction mixture was partitioned between water and ethyl acetate. The ethyl acetate layer was washed with water, brine, dried (Na$_2$SO$_4$) and concentrated to get (±)-2-(4-fluorophenoxymethyl)-7-(4-teterahydropyranyloxybutyn-1-yl)-oxepane 49 which was used with out further purification.

Part 8: (+)-2-(4-Fluorophenoxymethyl)-7-(4-hydroxybutyn-1-yl)-oxepane (Scheme X; 50)

(±)-2-(4Fluorophenoxymethyl)-7-(4-teterahydropyranyloxybutyn-1-yl)-oxepane 49 from the above reaction was dissolved in 5 ml of methanol and 2 ml of 1% HCl in methanol was added. Hydrolysis of the THF group was complete in 2 hours as detected by TLC (ethyl acetate:hexane 4:6). The reaction mixture was neutralized by addition of solid Na$_2$CO$_3$ and solvent was evaporated. The residue was dissolved in ethyl acetate, washed with water, brine, dried (Na$_2$SO$_4$) and concentrated. The crude product was purified on silica gel (ethyl acetate:hexane 3:7) to give (±)-2-(4-fluorophenoxymetyl)-7-(4-hydroxybutyn-1-yl)-oxepane 50 (0.24 g, 75%). The product was confirmed by $^1$H-NMR.

Part 9: (±)-2-(4-Fluorophenoxymethyl)-7-[4-(N,O-biscarbohenoxy)-1-butynyl]-oxepane (Scheme X; 51)

A solution of (±)-2-(4-fluorophenoxymetyl)-7-(4-hydroxybutyn-1-yl)-oxepane 50 (0.12 g, 0.41 mmol) and 5 ml of dry THF was cooled in an ice-water bath. Triphenylphosphine (0.13 g, 0.49 mmol), N,O-biscarbophenoxyhydroxylamine (0.135 g, 0.49 mmol) and diethyl azodicarboxylate (0.85 g, 0.49 mmol) were then added sequentially. The reaction mixture was stirred at room temperature. After 4 hours, solvent was in vacuo and the residue was dissolved in ethyl acetate, washed with water, brine, dried (Na$_2$SO$_4$) and concentrated. The residue was purified on silica gel (ethyl acetate:hexane 6:1) to give (±)-2-(4-fluorophenoxymethyl)-7-[4-N,O-biscarbo-henoxy)-butynyl]-oxepane 51 in 92% yield (0.195 g). The structure was confirmed by $^1$H-NMR.

Part 10: (±)-2-(4-Fluorophenoxymethyl)-7-(4N-hydroxy-ureidyl-1-butynyl)-oxepane (Scheme X; 52)

(±)-2-(4-Fluorophenoxymethyl)-7-[4-N,O-biscarbo-henoxy)-butynyl]-oxepane 51 was dissolved in 10 ml of methanol and 2 ml of a saturated solution of ammonia in methanol was added. The reaction mixture was stirred at room temperature. After 12 hours the solvent was removed and the crude product was purified on silica gel (ethyl acetate:hexane 1:1) to give (±)-2-(4-fluorophenoxymethyl)-7-(4-N-hydroxy-ureidyl-1-butynyl)-oxepane 52 in 82% yield (55 mg). The structure was confirmed by $^1$H-NMR.

EXAMPLE 8

Preparation of (2RS, 6S)-2-Benzenesulfonyl-6-(4-fluorophenoxymethyl)-tetrahydropyran.

References in this Example 8 to compound numerals (generally underlined) designate the compounds depicted structurally in the following Scheme XIX:

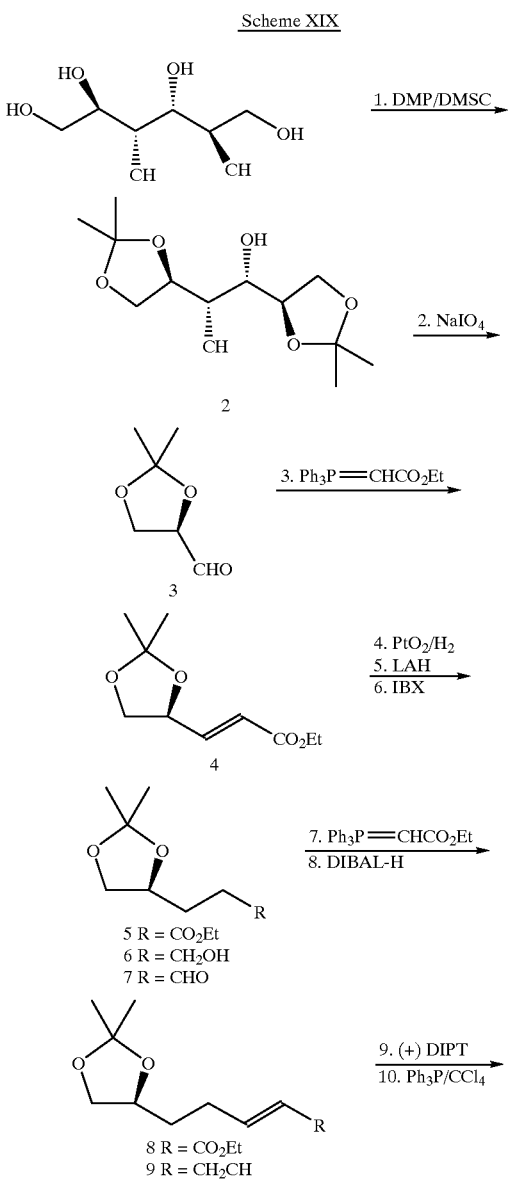

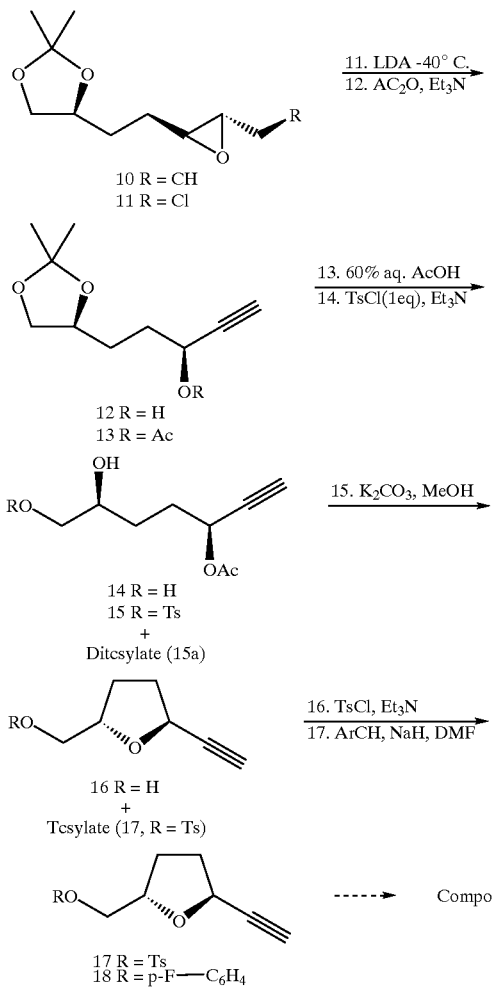

Part 1: (S)-Glycidyl-4-fluorophenyl ether (Scheme XIX,; 3)

To a solution of 4-fluorophenol (40 g, 0.35 mol) in acetone (350 ml) was added dry $K_2CO_3$ (148 g, 1.05 mol) and epichlorohydrin (95 ml, 1.05 mol). The reaction mixture was heated at 60° C. for 12 h, then filtered and the filtrate distilled under reduced pressure (b.p.160–170° C./9 mm) to afford pure (R, S)-glycidylfluorophenyl ether (52 g, 85%) as a colourless liquid. Co-salen acetate (RR-catalyst) (1.03 g, 1.54 mmol) was added to (R, S)-glycidyl-4-fluorophenyl ether (52 g, 0.31 mol), followed by drop wise addition of water (3.06 ml, 0.17 mol) over 1 h at 0° C. The reaction mixture was allowed to come to room temperature and stirred for 18 h. The catalyst was filtered off and the filtrate distilled under reduced pressure to afford (S)-glycidyl-4-fluorophenyl ether (22 g, 85%) as a colourless liquid. TLC: ethyl acetate-light petroleum (1:4), Rf=0.5. Boiling point: 160–170° C./9 mm. Optical rotation $[\alpha]_D$:+5° (c 2.3, $CHCl_3$). $^1H$ NMR ($CDCl_3$, 200 MHz) δ 2.68 (dd, J=4.5, 2.2 Hz, 1H), 2.85 (t, J=4.5 Hz,1H), 3.27 (m, 1H), 3.89 (dd, J=15.7, 6.7 Hz, 1H), 4.11 (dd, J=15.7, 4.5 Hz, 1H), 6.74–7.02 (m, 4H).

Part 2: Methyl (S)-6-(4-fluorophenoxy)-5-hydroxy-hex-2-ynoate (Scheme XLX; 4)

A solution of n-BuLi in hexane (11.4 ml, 26.8 mmol) was added at −78° C. to a solution of methyl propiolate (2.25 g, 26.8 mmol) in THF (15 ml) under $N_2$ atmosphere and the mixture was stirred for 20 min. Borontrifluoride etherate (3.4 ml, 26.8 mmol) was then added to the solution, stirring was continued for a further 20 min at −78° C. A solution of (S)-glycidyl-4-fluorophenyl ether (3 g, 17.8 mmol) in THF (10 ml) was then added and after stirring for 1 h at −78° C., the reaction was quenched by the addition of aqueous $NH_4Cl$. The reaction mixture was extracted with ethylacetate, dried ($Na_2SO_4$), and concentrated. The crude product was purified on a silica gel (EtOAc-light petroleum (1:4) as eluent) to afford methyl (S)-6-(4fluorophenoxy)-5-hydroxy hex-2-ynoate (2.5 g, 60%) as a yellow colour liquid. TLC: ethyl acetate-light petroleum (1:3), Rf=0.4. Optical rotation $[\alpha]_D$: +15.5° (c 1.2, $CHCl_3$). $^1H$ NMR ($CDCl_3$, 200 MHz): δ 2.62 (d, J=5 Hz, 1H), 2.71 (d, J=5.6 Hz, 2H), 3.76 (s, 3H), 3.92–4.02 (m, 2H), 4.2 (m, 1H), 6.8–7.02 (m, 4H).

Part 3: Methyl (S)-6-(4-fluorophenoxy)-5-hydroxy-hexanoate (Scheme XIX; 5)

To a solution of methyl (S)-6-(4fluorophenoxy)-5-hydroxy hex-2-ynoate (2.5 g, 9.9 mmol) in methanol (20 ml), 10% Pd/C (250 mg) was added and the mixture stirred under $H_2$ at room temperature for 3 h. The reaction mixture was filtered through celite, washed with methanol and concentrated in vacuum. The residue was purified on silica gel column using EtOAc-light petroleum (1:4) to give methyl (S)-6-(4-fluorophenoxy)-5-hydroxy-hexanoate (2.15 g, 85%) as a colourless liquid. TLC: ethyl acetate-light petroleum (1:3), Rf=0.4. Optical rotation $[\alpha]_D$: +8° (c 1.1, $CHCl_3$). $^1H$ NMR ($CDCl_3$, 200 MHz): δ 1.55–1.9 (m, 4H), 2.3–2.43 (t, J=6.5 Hz, 2H), 2.5 (s, 1H), 3.68 (s, 3H), 3.76–4.02 (m, 3H), 6.76–7.02 (m, 4H).

Part 4: (6S)-6-(4-Fluorophenoxymethyl)-tetrahydropyran-2-one (Scheme XIX; 6)

To a solution of methyl (S)-6-(4-fluorophenoxy)-5-hydroxy-hexanoate (0.8 g 3.12 mmol) in $CH_2Cl_2$ (20 ml), a catalytic amount of PTSA (10 mg) was added and the reaction mixture was stirred at 40° C. for 12 h. The reaction was then neutralised with sodium bicarbonate and the product extracted with dichloromethane. The organic layer was dried ($Na_2SO_4$) and concentrated. The crude product on purification on a silica gel (EtOAc-light petroleum (1:3) as eluent) gave (6S)-6-(4-fluorophenoxymethyl)-tetrahydropyran-2-one (0.5 g, 70%) as a colourless liquid. TLC:ethyl acetate-light petroleum (1:4), Rf=0.3. Optical rotation $[\alpha]_D$: +19° (c 0.9, $CHCl_3$). $^1H$ NMR ($CDCl_3$, 200 MHz): δ 1.7–2.15 (m, 4H), 2.48–2.7 (m, 2H), 3.95–4.15 (m, 2H), 4.55–4.7 (m, 1H), 6.77–7.0 (m, 4H).

Part 5: (2RS, 6S)-2-Benzenesulfonyl-6-(4-fluorophenoxymethyl)-tetrahydropyran (Scheme XIX; 8)

To solution of (6S)-6-(4-fluorophenoxymethyl)-tetrahydropyran-2-one (0.5 g, 2.23 mmol) in dry $CH_2Cl_2$ was added DIBAL-H (1 ml, 2M solution in toluene, 2.4 mmol) dropwise at −78° C. The reaction mixture was stirred at −78° C. for 3 h. It was then quenched with potassium sodium tartrate, extracted with dichloromethane, dried ($Na_2SO_4$), and concentrated to afford the crude product (0.42 g, 85%).

25% HCl was added dropwise to benzenesulfinic acid sodium salt (0.6 g), until the solid dissolved. This mixture was extracted with ethyl acetate (15 ml) dried ($Na_2SO_4$) and concentrated to give benzenesulfinic acid (0.4 g). To an ice-cooled mixture of benzenesulfinic acid (0.32 g, 2.23 mmol) and calcium chloride (0.25 g, 2.23 mmol) in dry CH$_2$Cl$_2$ a solution of (2RS, 6S)-6-(4-fluorophenoxymethyl)-2-hydroxy-tetrahydropyran (0.42 g, 1.86 mmol) in dry CH$_2$Cl$_2$ (5 ml) was added. The reaction mixture was stirred for 4 h, filtered through celite and washed with CH$_2$Cl$_2$. The combined organic layers were washed with saturated aqueous Na$_2$CO$_3$, water, brine and dried (Na$_2$SO$_4$). The solvent was removed under vacuum and the residue was purified on a silica gel column using light petroleum-ethyl acetate (4:1) as eluent to afford pure (2RS, 6S)-2-benzenesulfonyl-6-(4-fluorophenoxymethyl)-tetrahydropyran (0.5 g, 70%) as a viscous liquid. TLC:ethyl acetate-light petroleum (1:3), Rf=0.4. $^1$H NMR (CDCl$_3$, 200 MHz): δ 1.5 (m, 2H), 1.75–2.0 (m, 2H), 2.2–2.4 (m, 1H), 2.6–2.8 (m, 1H), 3.75–3.9 (m, 2H), 4.65 (d, 1H), 4.85–5.0 (m, 1H), 6.7–7.0 (m, 4H), 7.5–7.7 (m, 3H), 7.95 (d, J=5.4 Hz, 2H).

EXAMPLE 9

Preparation of (2S, 6S)-6-(4-Fluorophenoxymethyl)-2-(4-N-hydroxyureidyl-1-butynyl)-tetrahydropyran (Scheme XX; 17):

References in this Example 9 to compound numerals (generally underlined) designate the compounds depicted structurally in the following Scheme XX:

Scheme XX

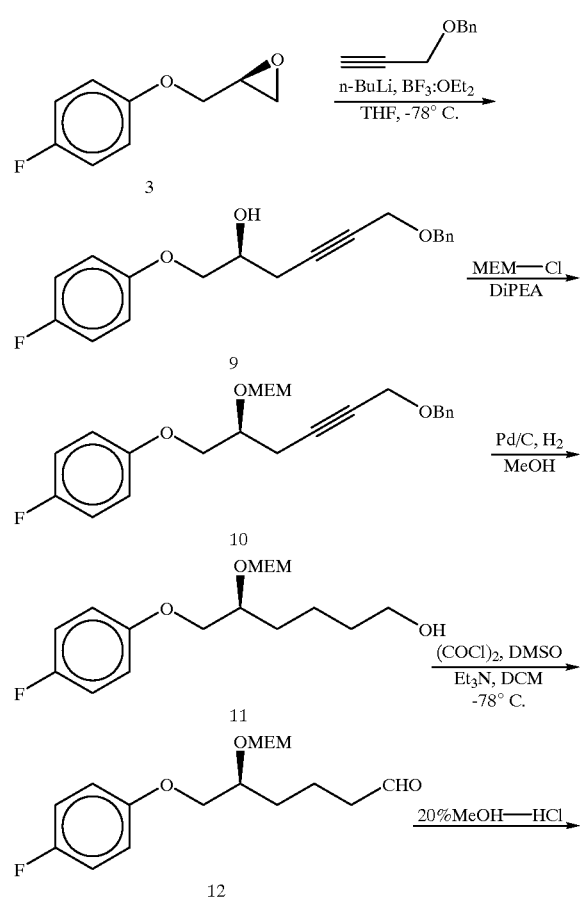

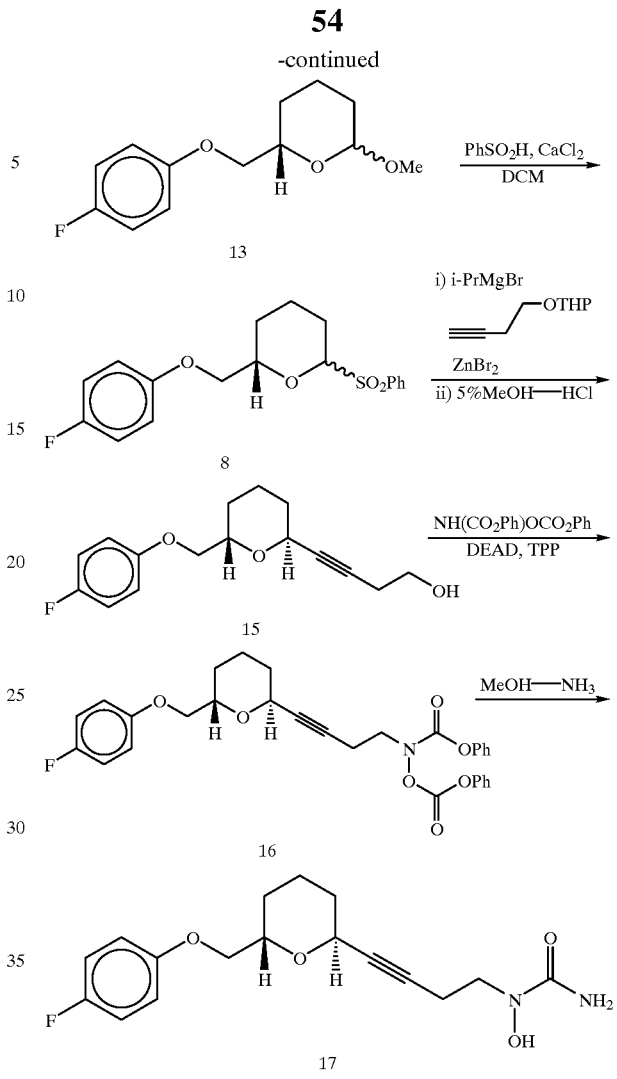

Part 1: (2S)-6-Benzyloxy-1-(4-fluorophenoxy)-hex-4-yn-2-ol (Scheme XX; 9)

To a solution of benzyloxy prop-2-yne (2.3 g, 16 mmol) in dry THF (25 ml) at −78° C. was added n-BuLi in hexane (10.7 ml, 16 mmol) and the mixture stirred for 20 min. Borontrifluoride etherate (2 ml, 16 mmol) was then added to the solution and stirring continued for 20 min. at −78° C. A THF solution of (S)-glycidol-4-fluorophenyl ether (1.8 g, 10.7 mmol) was added and after stirring for 1 h at −78° C., the reaction was quenched by adding aqueous NH$_4$Cl. The organic materials were extracted with ethyl acetate, dried (Na$_2$SO$_4$) and concentrated under vacuum. The crude product was purified on a silica gel column using EtOAc-light petroleum (1:4) as eluent to give (2S)-6-benzyloxy-1-(4-fluorophenoxy)-hex-4-yn-2-ol (2 g, 65%) as a yellow colour liquid. TLC:ethyl acetate-light petroleum (1:3), Rf=0.4. $^1$H NMR (CDCl$_3$, 200 MHz): 82.65 (m, 2H), 3.95–4.10 (m, 2H), 4.13–4.21 (m, 3H), 4.6 (s, 2H), 6.8–7.02 (m, 4H), 7.30–7.38 (m, 5H).

Part 2: (2S)-6-Benzyloxy-1-(4-fluorophenoxy)-2-(methoxyethoxymethyloxy)-hex-4-yne (Scheme XX; 10)

To an ice cooled solution of (2S)-6-benzyloxy-1-(4-fluorophenoxy)-hex-4-yn-2-ol (2 g, 6.4 mmol) in dry CH$_2$Cl$_2$ (8 ml) was added N-ethyldiisopropylamine (1.7 ml, 9.5 mmol) and stirred for 10 minutes MEM-chloride (1.1 ml, 9.5 mmol) was added to the solution at 0° C. and stirred for 3 h at room temperature. The solvent was concentrated and the residue purified on a silica gel column using EtOAc-light petroleum (1:4) as eluent to yield (2S)-6-benzyloxy-1-(4-fluorophenoxy)-2-(methoxyethoxymethyloxy)-hex-4-yne (2.2 g, 85%) as a yellow colour liquid. TLC:ethyl acetate-light petroleum (1:3), Rf=0.5 $^1$H NMR (CDCl$_3$, 200 MHz): δ 2.65–2.75 (m, 2H), 3.39 (s, 3H), 3.55 (t, J=4.8 Hz, 2H), 3.78 (t, J=4.8 Hz, 2H), 4.11 (s, 2H), 4.16 (m, 3H), 4.56 (s, 2H), 4.89 (s, 2H), 6.8–7.02 (m, 4H), 7.3–7.35 (m, 5H).

Part 3: (2S)-1-(4-Fluorophenoxy)-2-(methoxyethoxymethyloxy)-hexan-6-ol (Scheme XX; 11)

To a solution of (2S)-6-benzyloxy-1-(4-fluorophenoxy)-2-(methoxyethoxymethyloxy)-hex-4-yne (2.2 g, 5.4 mmol) in dry methanol (20 ml) was added 10% Pd/C (250 mg) and the mixture stirred under H$_2$ at room temperature for 4 h. The reaction mixture was filtered through celite, washed with excess methanol. Evaporation of the solvent afforded a crude product which was purified by silica gel column using ethyl acetate-light petroleum (2:3) as eluent to give (2S)-1-(4-fluorophenoxy)-2-(methoxyethoxymethyloxy)-hexan-6-ol (1.3 g, 76%) as a colourless liquid. TLC:ethyl acetate-light petroleum (2.3), Rf=0.3. $^1$H NMR (CDCl$_3$, 200 MHz) δ 1.5–1.7 (m, 6H), 3.35 (s, 3H), 3.5 (t, J=4.8 Hz, 2H), 3.65 (t, J=4.8 Hz, 2H), 3.7–3.8 (m, 2H), 3.85–3.95 (s, 3H), 4.75–4.95 (dd, J=12.6, 6.0 Hz, 2H), 6.75–7.0 (m, 4H).

Part 4: (2RS, 6S)-6-(4-Fluorophenoxymethyl)-2-methoxy-tetrahydropyran (Scheme XX; 13)

To a solution of (2S)-1-(4-fluorophenoxy)-2-(methoxyethoxymethyloxy)-hexan-6-ol (1.25 g, 3.9 mmol) and oxalyl chloride (0.7 ml, 7.9 mmol) in dry CH$_2$Cl$_2$ was added dry DMSO (1.12 ml, 15.8 mmol) slowly at −78° C. The stirring was continued for a further 30 min. at −78° C. and quenched with dry Et$_3$N (3.15 ml, 23.7 mmol). The reaction mixture was extracted with CH$_2$Cl$_2$ and dried (Na$_2$SO$_4$) to afford the crude aldehyde (1.1 g, 85%). A 20% methanolic HCl solution was added to the aldehyde and stirred for 5 h. at room temperature. The reaction mixture was neutralised with aqueous NaHCO$_3$, extracted with ethyl acetate, dried (Na$_2$SO$_4$) and concentrated under vacuum. The crude product was purified by silica gel column chromatography to give a cis-trans mixture (2RS, 6S)-6-(4-fluorophenoxymethyl)-2-methoxytetrahydropyran (0.6 g, 80%) as a yellow syrup. TLC:ethyl acetate-light petroleum (1:3), Rf=0.8. $^1$H NMR (CDCl$_3$, 200 MHz): δ 1.6–2.0 (m, 6H), 3.45 (s, 3H), 3.9–3.96 (m, 2H), 4.0–4.15 (m, 1H), 4.8 (s, 1H), 6.8–7.01 (m, 4H).

Part 5: (2RS, 6S)-2-Benzenesulfonyl-6-(4-fluorophenoxymethyl)-tetrahydropyran (Scheme XX; 8)

25% HCl was added dropwise to benzenesulfinic acid sodium salt (2.0 g), till the solid dissolved. This mixture was extracted with ethyl acetate (30 ml), dried (Na$_2$SO$_4$) and concentrated to give benzenesulfinic acid (1.5 g). To an ice-cooled mixture of benzenesulfinic acid (1.48 g, 10.5 mmol) and calcium chloride (1.15 g, 10.5 mmol) in dry CH$_2$Cl$_2$ a solution of (2RS, 6S)-6-(4-fluorophenoxymethyl)-2-methoxytetrahydropyran (0.5 g, 2.1 mmol) in dry CH$_2$Cl$_2$ (5 ml) was added. The reaction mixture was stirred for 4 h, filtered through celite and washed with CH$_2$Cl$_2$. The combined organic layer was washed with saturated aqueous Na$_2$CO$_3$, water, brine and dried (Na$_2$SO$_4$). The solvent was removed under vacuum and the residue was purified on a silica gel column using light petroleum-ethyl acetate (4:1) as eluent to afford pure (2RS, 6S)-6-benzenesulfonyl-2-(4-fluorophenoxymethyl)-tetrahydropyran (0.5 g, 70%) as a viscous liquid. TLC:ethyl acetate-light petroleum (1:3), Rf=0.4. $^1$H NMR (CDCl$_3$, 200 MHz): δ 1.5 (m, 2H), 1.75–2.0 (m, 2H), 2.2–2.4 (m, 1H), 2.6–2.8 (m, 1H), 3.75–3.9 (m, 2H), 4.65 (d, 1H), 4.85–5.0 (m, 1H), 6.7–7.0 (m, 4H), 7.5–7.7 (m, 3H), 7.95 (d, J=5.4 Hz, 2H).

Part 6: (2S, 6S)-6-(4-Fluorophenoxymethyl)-2-(4-hydroxybutyn-1-yl)-tetrahydropyran (Scheme XX; 15)

To a suspension of magnesium (0.14 g, 5.7 mmol) in dry THF (5 ml) catalytic 1,2-dibromoethane was added followed by dropwise addition of a solution of isopropylbromide (0.3 ml, 2.86 mmol) in THF. The reaction mixture was stirred for 1 h and the isopropylmagnesiumbromide was cannulated into a two necked flask. A solution 4-tetrahydropyranoyl-1-butyne (0.44 g, 2.86 mmol) in THF (2 ml) was added and the mixture was stirred for 30 min. and cooled to 0° C. Freshly prepared ZnBr$_2$ solution (2 ml, 1.7 mmol) in THF was introduced dropwise. After 45 min. at room temperature (2RS,6S)-2-benzenesulfonyl-6-(4fluorophenoxymethyl)-tetrahydropyran (0.5 g, 1.43 mmol) in THF (4 ml) was added and the mixture stirred for 3 h. The reaction was quenched with saturated aqueous NH$_4$Cl solution at 0° C. THF was removed under vacuum and the residue was extracted with ethyl acetate, dried (Na$_2$SO$_4$) and concentrated to give (2S, 6S)-6-(4-fluorophenoxymethyl)-2-(4-tetrahydropyranoyl-1-butyne)-tetrahydropyran. The crude product was dissolved in methanol (5 ml) and 5% HCl in methanol (10 ml) was added. The reaction mixture was stirred at room temperature for 2 h and neutralised with saturated aqueous Na$_2$CO$_3$ solution and concentrated. The residue was extracted with ethyl acetate, dried (Na$_2$SO$_4$) and concentrated. The crude product was purified on a silica gel column to give (2S, 6S)-6-(4-fluorophenoxymethyl)-2-(4-hydroxybutyn-1-yl)-tetrahydropyran (0.24 g, 70%) as a colourless liquid and as a single isomer (by HPLC). TLC:ethyl acetate-light petroleum (1:3), Rf=0.3. Optical rotation [α]$_D$: −32° (c 1.1, CHCl$_3$). $^1$H NMR (CDCl$_3$, 200 MHz): δ 1.6–2.0 (m, 6H), 2.55 (m, 2H), 3.73 (t, J=6.35 Hz, 2H), 3.8–4.0 (m, 2H), 4.15–4.3(m, 1H), 4.8 (s, 1H), 6.8–7.0 (m, 4H).

Part 7: N,O-bis-phenoxycarbonylhydroxylamine

To a solution of sodium bicarbonate (21.5 g, 0.256 mol) in water (150 ml) at 0° C. was added hydroxylamine hydrochloride (8.8 g, 0.127 mol). The reaction mixture was stirred for 30 min. and phenylchloroformate (60 g, 0.383 mol) was introduced directly into the vigorously stirred mixture. Sodium bicarbonate (32.3 g, 3.85 mol) in water (300 ml) was added to the mixture. The mixture was stirred for 30 min., the ice-bath removed and stirring continued for an additional 2 h at room temperature. The resultant suspension was filtered and the filter cake washed with water. The wet filter cake was collected, suspended in hexane, filtered and again washed with hexane. The solid was kept at 0° C. overnight to afford N,O-bis-phenoxycarbonylhydroxylamine (23.5 g, 68%) as a solid. Melting point: 80–82° C. $^1$H NMR (CDCl$_3$, 200 Mz): δ 7.26(m, 5H), 7.42 (m, 5H) and 8.54 (s, 1H).

Part 8: (2S, 6S)-6-(4-Fluorophenoxymethyl)-2-(4-N,O-bis-phenoxycarbonylhydroxylamino-1-butynyl)-tetrahydropyran (Scheme XX; 16)

To an ice cooled solution of (2S, 6S)-6-(4fluorophenoxymethyl)-2-(4-hydroxybutyn-1-yl)- tetrahydropyran (0.23 g, 0.83 mmol) in dry THF (10 ml), triphenylphosphine (0.26 g, 0.99 mmol) and N,O-bis-phenoxycarbonyl hydroxylamine (0.26 g, 0.95 mmol) were added. After 15 min., diethylazodicarboxylate (0.173 g, 0.99 mmol) was added dropwise. The mixture was then allowed to warm to room temperature and stirred for 3 h. The solvent was evaporated under reduced pressure and the residue purified on a silica gel column to yield (2S, 6S)-6-(4-fluorophenoxymethyl)-2-(4-N,O-bis-phenoxycarbonylhydroxylamino-1-butynyl)-tetrahydropyran (0.3 g, 70%) as a yellow colour liquid. TLC:ethyl acetate-light petroleum (1:3), Rf=0.6. $^1$H NMR (CDCl$_3$, 200 MHz): δ 1.45–1.8 (m, 6H), 2.75 (t, J=6.8 Hz, 2H), 3.75–3.9 (m, 2H), 4.0–4.1 (t, J=7.32 Hz, 2H), 4.15–4.3 (m, 1H), 4.8 (s, 1H), 6.7–6.95 (m, 4H), 7.1–7.45 (m, 10H). Part 9: (2S, 6S)-6-(4-Fluorophenoxymethyl)-2-(4-N-hydroxyureidyl-1-butynyl)-tetrahydropyran (Scheme XX; 17)

A solution of (2S, 6S)-6-(4-fluorophenoxymethyl)-2-(4-N,O-bis-phenoxycarbonyl hydroxylamino-1-butynyl)-tetrahydropyran (0.3 g, 0.56 mmol) and aqueous NH$_4$OH in methanol (10 ml) were stirred at room temperature for 12 h. Methanol was evaporated and the residue was purified on a silica gel column using light petroleum-ethyl acetate (2:3) as eluent to give (2S, 6S)-6-(4-fluorophenoxymethyl)2-(4-N-hydroxyureidyl-1-butynyl)-tetrahydropyran (0.12 g, 65%) as a yellow viscous liquid. TLC: ethyl acetate-light petroleum (4:1), Rf=0.3. Optical rotation [α]$_D$: −28.6° (c 1.2, CHCl$_3$). $^1$H NMR (CDCl$_3$, 200 MHz): δ 1.5–2.0 (m, 6H), 2.45–2.6 (t, J=6.35 Hz, 2H), 3.65 (t, J=7.32 Hz, 2H), 3.75–3.9 (m, 2H), 4.1–4.3 (m, 1H), 4.75.

EXAMPLE 10

Preparation of (2S, 6S)-6-(4-Fluorophenoxymethyl)-2-(4-N-hydroxyureidyl-1-butynyl)-tetrahydropyran (Scheme XXI; 9):

References in this Example 10 to compound numerals (generally underlined) designate the compounds depicted structurally in the following Scheme XXI.

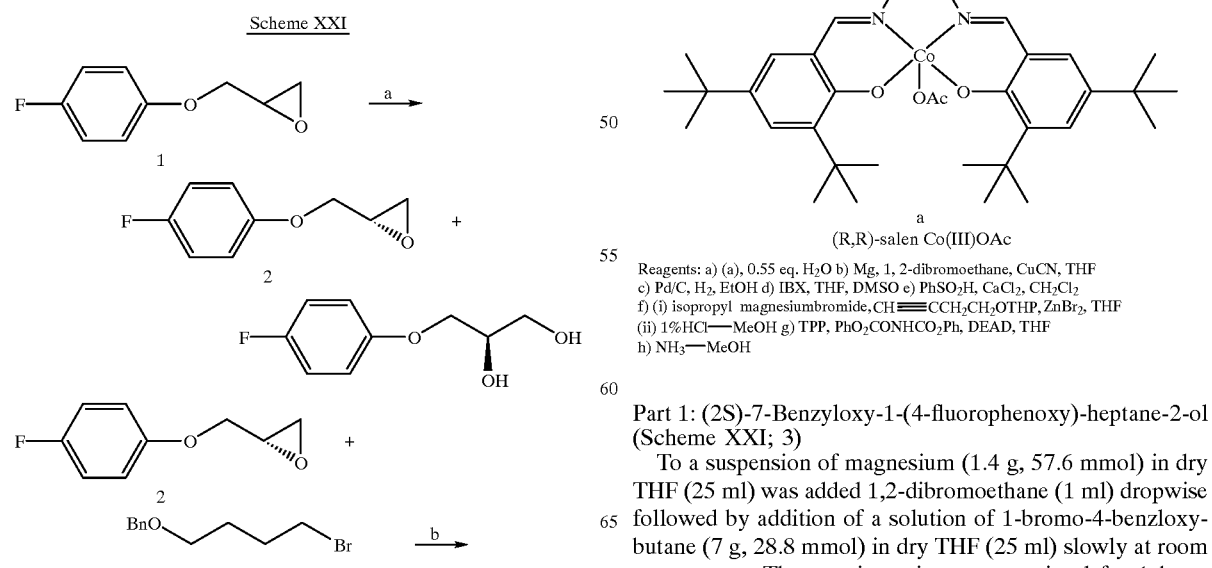

Reagents: a) (a), 0.55 eq. H$_2$O b) Mg, 1, 2-dibromoethane, CuCN, THF
c) Pd/C, H$_2$, EtOH d) IBX, THF, DMSO e) PhSO$_2$H, CaCl$_2$, CH$_2$Cl$_2$
f) (i) isopropyl magnesiumbromide, CH≡CCH$_2$CH$_2$OTHP, ZnBr$_2$, THF
(ii) 1%HCl—MeOH g) TPP, PhO$_2$CONHCO$_2$Ph, DEAD, THF
h) NH$_3$—MeOH Part 1: (2S)-7-Benzyloxy-1-(4-fluorophenoxy)-heptane-2-ol (Scheme XXI; 3)

To a suspension of magnesium (1.4 g, 57.6 mmol) in dry THF (25 ml) was added 1,2-dibromoethane (1 ml) dropwise followed by addition of a solution of 1-bromo-4-benzloxy-butane (7 g, 28.8 mmol) in dry THF (25 ml) slowly at room temperature. The reaction mixture was stirred for 1 hour, cooled in ice-salt bath and then CuCN (50.0 mg, 0.57 mmol) was added followed by a solution of (S)-4-fluorophenylglycidyl ether (2.9 g, 17.3 mmol) in dry THF (30 ml) was introduced slowly. The reaction was stirred for 15 min and quenched with saturated aqueous ammonium chloride solution at 0° C. THF was removed under vacuum and the residue partitioned between EtOAc and water. The organic layer was successively washed with water and brine, dried over $Na_2SO_4$ and concentrated. The crude product was purified on silica gel chromatography using EtOAc-hexane (1:6) as eluent to give (2S)-7-benzyloxy-1-(4-fluorophenoxy)-heptane-2-ol (5.8 g, 73%), $[\alpha]_D$+12 (c 2.2, $CHCl_3$), $^1$H-NMR ($CDCl_3$, 200 Hz): δ 1.35–1.69 (m, 8H), 3.45 (t, J=6.25 Hz, 2H), 3.71–3.95 (m, 2H), 4.48 (s, 2H), 6.77–7.00 (m, 4H), 7.27–7.35 (m, 5H); HRMS (FAB): calcd. for $C_{20}H_{25}O_3F$ (M+) 332.178773 found 332.180309.

Part 2: (6S)-7-(4-fluorophenoxy)-heptane-1,6-diol (Scheme XXI; 4)

To a solution of (2S)-7-Benzyloxy-1-(4-fluorophenoxy)-heptane-2-ol (5.8 g, 17.5 mmol) in ethanol (30 ml), 10% of Pd/C (100 mg) was added and stirred under $H_2$ atmosphere at normal temperature and pressure for 3 hours. The reaction mixture was filtered through celite, washed with ethanol and concentrated. The residue was purified by silicia gel chromatography using EtOAc-hexane (1:1) to give (6S)-7-(4-fluorophenoxy)-heptane-1,6-diol (3.92 g, 93%); $[\alpha]_D$+12 (c 3.1, $CHCl_3$), $^1$H-NMR ($CDCl_3$, 200 Hz): δ 1.29–1.69 (m, 8H), 3.65 (t, J=6.8 Hz, 2H), 3.82–4.02 (m, 2H), 6.75–7.0 (m, 4H); HRMS (EI): calcd. for $C_{13}H_{19}O_3F$ (M+) 242.131823 found 242.131900.

Part 3: (6S)-7-(4-fluorophenoxy)-6-hydroxy-heptanal (Scheme XXI; 5)

To a solution of (6S)-7-(4-fluorophenoxy)-heptane-1,6-diol (3.6 g, 14.8 mmol) in dry THF (60 ml) was added dropwise a solution of 2-iodobenzoic acid (5 g, 17.8 mmol) in dry DMSO (4 ml) over a period of 25 minutes at room temperature. After 15 minutes the reaction mixture was decomposed with crushed ice, filtered through celite and concentrated. The residue was extracted with ethylether, washed with brine, dried over $Na_2SO_4$ and the organic solvent was removed under reduced pressure. The residue was purified by silica gel chromatography using EtOAc-hexane (1:9) to give (6S)-7-(4-fluorophenoxy)-6-hydroxy-heptanal (2.2 g, 61.6%); $[\alpha]_D$+12 (c 3.8, $CHCl_3$), $^1$H-NMR ($CDCl_3$, 200 Hz): δ 1.4–1.8 (m, 6H), 2.49 (dt, 2H), 3.71–4.05 (m, 4H), 6.782–7.02 (m, 4H), 9.8 (s, 1H); HRMS (FAB): calcd. for $C_{13}H_{17}O_3F$ (M+) 240.116173 found 240.116465.

Part 4: (2RS,7S)-2-(Benzenesulfonyl)-7-(4-fluorophenoxymethyl)oxepane (Scheme XXI; 6)

25% HCl was added dropwise to sodium salt of benzenesulfinic acid (5 g, 30.5 mmol) until the solid dissolved. The reaction mixture was extracted with EtOAc, dried over $Na_2SO_4$ and concentrated to give benzenesulfinic acid (3.9 g, 90%). To an ice-cold mixture of benzene sulfinic acid (1.8 g, 12.4 mmol) and $CaCl_2$ (1.4 g, 12.5 mmol) in dry methylene chloride (50 ml) was added dropwise a solution of (6S)-7-(4-fluorophenoxy)-6-hydroxyheptanal (2 g, 8.3 mmol) in methylene chloride (10 ml). The reaction mixture was stirred for 3 hours and filtered through celite, and washed with methylene chloride. The combined organic layer was washed with saturated aqueous $Na_2CO_3$, water, brine and dried over $Na_2SO_4$. Solvent was removed under reduced pressure and the residue was purified by silica gel chromatography using EtOAC-hexane (1:6) as eluent to give (2RS,7S)-2-(benzenesulfonyl)-7-(4-fluorophenoxymethyl) oxepane (2.45 g, 80.8%); $^1$H-NMR ($CDCl_3$, 200 Hz): δ 1.39–2.20 (m, 7H), 2.5 (m, 1H), 3.57–3.90 (m, 2H), 4.45 (m, 1H), 4.72 (dd, J=6.6, 12.0 Hz, 1H), 6.57–7.00 (m, 4H), 7.36–7.96 (m, 5H).

Part 5: (2S,7S)-7-(4-Fluorophenoxymethyl)-2-(4-hydroxybutynyl)oxepane (Scheme XXI; 7)

To a suspension of magnesium (0.58 g, 24.2 mmol) in dry THF (10 ml) was added catalytic 1,2-dibromoethane followed by dropwise addition of a soluton of isopropyl bromide (1.85 g, 15.1 mmol) in THF (5 ml). The reaction mixture was stirred for 1 hour and isoprpylmagnesiumbromide was cannulated into a 50 ml two-necked flask. A solution of 4-tetrahydropyranoyl-1-butyne (1.86 g, 12.0 mmol) in THF (5 ml) was added and the mixture was stirred for 30 minutes followed by addition of freshly prepared $ZnBr_2$ solution (1 M, 7.25 ml, 7.2 mmol) in THF at 0°. After 45 minutes (2RS,7S)-2-(benzenesulfonyl)-7-(4-fluorophenoxymethyl)oxepane (2.2 g, 6.0 mmol) in THF (10 ml) was added and the mixture stirred for 30 hours. The reaction was quenched with saturated aqueous $NH_4Cl$ solution at 0° C. THF was removed under reduced preesure and the residue was portioned between EtOAc and water. The organic layer was washed with a brine, dried over $Na_2SO_4$ and concentrated to give (2S,7S)-7-(4-fluorophenoxymethyl)-2-(4-tetrahydropyranoyl-1-butynyl) oxepane. The crude product was dissolved in MeOH (25 ml) and 1% HCl in MeOH (5ml) was added. The hydrolysis of the THF group was completed in 2 hours and neutralized with saturated $Na_2CO_3$ solution and concentrated. The crude product was purified by silica gel chromatography using EtOAc-hexane (1:8) to give (2S,7S)-7-(4-fluorophenoxymethyl)-2-(4-hydroxybutynyl)oxepane (1.32 g, 75%); $[\alpha]_D$–74 (c 3.63, $CHCl_3$), $^1$H-NMR ($CDCl_3$, 200 Hz): δ 1.4–2.0 (m, 7H), 2.12 (m, 1H), 2.3 (s, 1H), 2.46 (dt, 2H), 3.65 (t, J=3.6 Hz, 2H), 3.74–3.97 (m, 2H), 4.51 (q, 1H), 6.8–7.0 (m, 4H); HRMS (EI): calcd. for $C_{17}H_{21}O_3F$ (M+) 292.147756 found 292.147473. Also, (2S,7S)-7-(4-fluorophenoxymethyl)-2-(4-hydroxybutynyl)oxepane by similar procedure: $[\alpha]_D$+26.9 (c 2.2, $CHCl_3$), $^1$H-NMR ($CDCl_3$, 200 Hz): δ 1.48–2.03 (m, 8H), 2.2 (s, 1H), 2.47 (dt, 2H), 3.69 (t, J=6.9 Hz, 2H), 3.74–4.02 (m, 3H), 4.34 (dt, 2H), 6.78–7.0 (m, 4H).

Part 6: (2S,7S)-7-(4-Fluorophenoxymethyl)-2-[4-(N,O-biscarbophenoxy)-1-butynyl]oxepane (Scheme XXI; 8)

A mixture of (2S,7S)-7-(4-fluorophenoxymethyl)-2-(4-hydroxybutynyl)oxepane (0.9 g, 3.1 mmol), TPP (1.0 g, 3.7 mmol), N,O-biscarbophenoxy-hydroxylamine (1 g, 3.7 mmol) in dry THF (20 ml) was cooled to 0° C. Diethylazacarboxylate (0.64 g, 3.7 mmol) was added dropwise and the reaction mixture stirred at room temperature for 4 hours. Solvent was removed on rotovapor. The residue was partitioned between FtOAc and water, washed with brine, dried over $Na_2SO_4$ and concentrated. The product was purified by silica gel chromatography using EtOAc-hexane (1:9) to give pure (2S,7S)-7-(4-fluorophenoxymethyl)-2-[4-(N,O-biscarbophenoxy)-1-butynyl]oxepane (1.55 g, 92%); $[\alpha]_D$–46.0 (c 2.42, $CHCl_3$), $^1$H-NMR ($CDCl_3$, 200 Hz): δ 1.39–22.0 (m, 8H), 2.73 (t, J=6.9 Hz, 2H), 3.72–4.07 (m, 4H), 4.15 (m, 1H), 4.51 (dt, 1H), 6.76–7.46 (m, 4H). Also, (2R,7S)-7-(4-Fluorophenoxymethyl)-2-[4-(N,O-biscarbophenoxy)-1-butynyl]oxepane by similar procedure: $[\alpha]_D$+11 (c 4.3, CHCl$_3$), $^1$H-NMR (CDCl$_3$, 200 Hz): δ 1.48–2.03 (m, 8H), 3.76 (dt, 2H), 3.68–4.08 (m, 5H), 6.75–7.47 (m, 14H).

Part 7: (2S,7S)-7-(4-fluorophenoxymethyl)-2-(4N-hydroxy-ureidyl-1-butynyl)oxepane (Scheme XXI; 9)

A solution of (2S,7S)-7-(4-Fluorophenoxymethyl)-2-[4-(N,O-biscarbophenoxy)-1-butynyl]oxepane (1.4 g, 2.6 mmol) in MeOH (25 ml) was cooled to 0° C. Saturated methanolic ammonia solution (10 ml) was added and the reaction was stirred for 12 hours at room temperature. Solvent was removed and the residue was purified by silica gel chromatography using EtOAc-hexane (1:1) to give (2S,7S)-7-(4-fluorophenoxymethyl)-2-(4N-hydroxy-ureidyl-1-butynyl)oxepane (820 mg, 92.5%); $[\alpha]_D$–56.0 (c 2.15, CHCl$_3$), $^1$H-NMR (CDCl$_3$, 200 Hz): δ 1.43–2.20 (m, 8H), 2.51 (dt, 2H), 3.7 (t, J=7.1 Hz, 2), 3.8–3.96 (m, 2H), 4.13 (m, 1H), 4.51 (q, 1H), 5.25 (s, 2H), 7.83–8.02 (m, 4H), 7.70 (s, 1H); HRMS (FAB): calcd. for C$_{18}$H$_{24}$O$_4$N$_4$F (M+) 351.172011 found 351.173621. 13C: 17.187, 24.589, 27.452, 32.032, 37.125, 48.887, 67.114, 72.029, 72.312, 81.857, 82.414, 115.506, 115.658, 115.814, 115.965, 154.903, 159.661, 161.788. Also, (2R,7S)-7-(4-fluorophenoxymethyl)-2-(4hydroxybutynyl)oxepane by similar procedure: $[\alpha]_D$+32 (c 0.5, CHCl$_3$), $^1$H-NMR (CDCl$_3$, 200 Hz): δ 1.42–1.94 (m, 8H), 2.44 (s, 1H), 3.57 (t, J=7.1 Hz, 2H), 3.69–3.92 (m, 3H), 5,44 (s, 2H), 6.72–6.97 (m, 4H), 8.1 (s, 1H).

EXAMPLE 11

Synthesis of (2R,5R)-5-Ethynyl-2-(hydroxymethyl)-tetrahydrofuran from L-Glyceraldehyde References in this Example 11 to compound numerals (generally underlined) designate the compounds depicted structurally in Scheme XV above.

Part 1: Ethyl (2E,4R)-4,5-isopropylidenedioxy-2-pentenoate (Scheme XV; 20)

A solution of (2S,3R)-1,2-O-isopropylidene-butane-1,2,3,4-tetrol 19 (11.0 g, 68.1 mmol) in CH$_2$Cl$_2$ (120 mL) containing saturated NaHCO$_3$ solution (4.5 mL) was cooled to 0° C., treated with NaIO$_4$ (29.1 g, 136.3 mmol) and allowed to stir at 0° C. to 20° C. After 2 to 3 h (TLC analysis), solid Na$_2$SO$_4$ (6 g) was added and the reaction mixture was stirred further for 15 min. The reaction mixture was filtered and solvent evaporated (below 25° C. bath temperature) to give (S)-glyceraldehyde 19a (8.7 g) in 98% yield as a colorless liquid. Compound 19 was prepared by procedures described in *J. Am. Chem. Soc.*, 102, 6304 (1980); and *J. Org. Chem.*, 53, 2598 (1988).

A solution of (S)-glyceraldehyde 19a (15 g, 115.4 mmol) in MeOH (200 mL) was cooled to 0°–10° C. (ice-salt bath) and treated with (carbethoxymethylene) triphenyl phosphorane (48.1 g, 138.4 mmol) in portions. After stirring at room temperature for 9 h, the solvent was evaporated, the residue obtained on purification by column chromatography (Si-gel, 10% EtOAc-Hexane) gave ethyl (2E,4R)-4,5-isopropylidenedioxy-2-pentenoate 20 (23 g) in 99% yield as a pale yellow liquid. $[\alpha]_D$–116.3(c 0.71, CHCl$_3$); $^1$HNMR (CDCl$_3$, 200 MHz): δ 1.2 (t, 3H, J 6.8 Hz, CH$_3$), 1.3, 1.35 (2s, 6H, CH$_3$), 3.5 (dd, 1H, J 5.9 Hz, H-5), 4.07 (q, 2H, J 6.8 Hz, —OCH$_2$), 4.27 (dd, 1H, J 5.9 Hz, H-5a), 5.32–5.43 (m, 1H, H-4), 5.72 (dd, 1H, J 2.2, 11.3 Hz, H-2), 6.27 (dd, 1H, J 5.4, 11.3 Hz, H-3); $^{13}$CNMR (CDCl$_3$, 50 MHz): δ 13.0, 25.2, 26.3, 60.1, 69.21, 73.3, 109.4, 120.5, 149.1, 165.3; EIMS m/z (relative intensity): 185 (M$^+$–15, 15), 173 (6), 149 (23), 125 (20), 97 (45), 43 (100); HRMS: Calculated for C$_9$H$_{13}$O$_4$ (M$^+$–15): 145.086469; Observed: 145.087162.

Part 2: Ethyl (4R)-4,5-isopropylidenedioxy-1-pentanoate (Scheme XV; 21)

A solution of ethyl (2E,4R)-4,5-isopropylidenedioxy-2-pentenoate 20 (23 g, 115 mmol) in EtOAc (50 mL) was treated with PtO$_2$ (0.100 g, mmol) and hydrogenated till there was no additional consumption of hydrogen (3–4 h). At the end of reaction, the reaction mixture was filtered and concentrated to afford ethyl (4R)-4,5-isopropylidenedioxy-1-pentanoate 21 (23 g) in 99% yield as a colorless liquid. $[\alpha]_D$–4.0(c 2.0, CHCl$_3$); $^1$HNMR (CDCl$_3$, 200 MHz): δ 1.25 (t, 3H, J6.8 Hz, CH$_3$), 1.29, 1.32 (2s, 6H, CH$_3$), 1.75–1.89 (m, 2H, H-3), 2.3–2.45 (m, 2H, H-2), 3.5 (t, 1H, J 6.5 Hz, H-5), 3.92–4.15 (m, 4H, H-4,5a, —OCH$_2$); $^{13}$CNMR (CDCl$_3$, 50 MHz): δ 14.0, 25.4, 26.8, 28.6, 30.2, 60.1, 68.8, 74.7, 108.7, 172.6. EIMS m/z (relative intensity): 203 (M$^+$+1, 23), 173 (16.4), 143 (13.4), 101 (100), 43 (97); HRMS: Calculated for C8H$_{13}$O$_4$ (M$^+$–29): 173.081384; Observed: 1173.081619.

Part 3: (2R)-1,2-Isopropylidenedioxy-5-pentanol (Scheme XV; 22)

A suspension of LAH (4.93 g, 130.4 mmol) in THF (50 mL) was cooled to 0° C. and treated drop wise with a solution of ethyl (4R)-4,5-isopropylidenedioxy-1-pentanoate 21 (22 g, 108.9 mmol) in THF (75 mL). The reaction mixture was warmed to room temperature, then allowed to stir for 3 h and treated with a saturated solution of Na$_2$SO$_4$ (15 mL). After stirring for additional 30 min., it was filtered through celite and washed with EtOAc (3×75 mL). The combined organic layers were washed with NaCl solution and evaporated to provide the (2R)-1,2-isopropylidenedioxy-5-pentanol 22 (17 g) in 97% yield as a colorless liquid. $[\alpha]_D$–10.3(c 0.75, CHCl$_3$); $^1$HNMR (CDCl$_3$, 200 MHz): δ 1.35, 1.4 (2s, 6H), 1.6–1.75 (m, 4H, H-3,4), 1.92 (br.s, 1H, OH), 3.5 (t, 1H, J 6.1 Hz, H-1), 3.6–3.72 (m, 2H, H-5), 3.98–4.16 (m, 2H, H-1a,2); $^{13}$CNMR (CDCl$_3$, 50 MHz): δ 25.6, 26.8, 29.0, 30.1, 62.4, 69.4, 75.9, 108.8; EIMS m/z (relative intensity): 145 (M$^+$–15, 13.4), 85 (32), 72 (18), 57 (13.4), 43 (100); HRMS: Calculated for C$_7$H$_{13}$O$_3$ (M$^+$–15): 145.086468; Observed: 145.087162.

Part 4: (4R)-4,5-Isopropylidenedioxy-1-pentanal (Scheme XV; 23)

Method A: A stirred solution of (2R)-1,2-isopropylidenedioxy-5-pentanol 22 (17 g, 106.3 mmol) in CH$_2$Cl$_2$ (200 mL) was treated with PDC (59.9 g, 159.3 mmol) in portions and allowed stir at 40° C. for 5 h. The reaction mixture was diluted with ether (4×300 mL) and decanted through a small pad of silica gel. Evaporation of solvent afforded (4R)-4,5-isopropylidenedioxy-1-pentanal 23 (15 g) in 89% yield as a pale yellow liquid.

Method B: A stirred solution of (2R)-1,2-isopropylidenedioxy-5-pentanol 22 (0.800 g, 5.0 mmol) in DMSO (5 mL) was cooled to 0° C., treated with IBX (1.47 g, 5.26 mmol) in portions while maintaining the temperature below 0° C. and stirred at room temperature for 4 h. The reaction mixture was treated with saturated NaHCO$_3$ solution, filtered through celite and washed with EtOAc (3×30 mL). Two layers were separated and organic layer was washed with water, brine and dried (Na$_2$SO$_4$). Evaporation of solvent gave (4R)-4,5-isopropylidenedioxy-1-pentanal 23 (16.2 g) in 78% yield as a yellow liquid. [α]$_D$+0.3(c 2.0, CHCl$_{13}$).

Part 5: Ethyl (2E,6R)-6,7-isopropylidenedioxy hept-2-enoate (Scheme XV; 24)

A solution of(4R)-4,5-isopropylidenedioxy-1-pentanal 23 (15 g, 94.9 mmol) in benzene (200 mL) was treated with (carbethoxymethylene) triphenyl phosphorane (39.6 g, 113.8 mmol) and heated at reflux for 6 h. Solvent was evaporated and the residue purified by column chromatography (Si-gel, 10% EtOAc-hexane) to afford ethyl (2E,6R)-6,7-isopropylidenedioxy hept-2-enoate 24 (14 g) in 65% yield as a pale yellow liquid. [α]$_D$−5.4(c 1.2, CHCl$_3$); $^1$HNMR (CDCl$_3$, 200 MHz): δ 1.3 (t, 3H, J 6.8 Hz,CH$_3$), 1.34, 1.4 (2s, 6H), 1.61–1.7 (m, 2H, H-6), 2.2–2.42 (m, 2H, H-4), 3.5 (t, 3H, J 6.8 Hz, CH$_3$), 7a), 3.99–4.26 (m, 4H, H-6,7,—OCH$_2$), 5.82 (td,1H, J 2.25, 15.75 Hz, H-2), 6.94 (dt, 1H, J 6.8, 15.75 Hz, H-3); $^{13}$CNMR (CDCl$_3$, 50 MHz): δ 14.0, 25.4, 26.7, 28.2, 31.9, 60.0, 69.0, 74.9, 108.7, 121.7, 147.7, 166.3; EIMS m/z(relative intensity): 213 (M$^+$−15, 9), 95 (40.2), 67 (25.3), 55 (53.7), 41 (100); HRMS: Calculated for C$_{11}$H$_{17}$O$_4$ (M$^+$−15): 213.112684; observed: 213.112732.

Part 6: (2E,6R)-6,7-Isopropylidenedioxy hept-2-ene-1-ol (Scheme XV; 25)

A stirred solution of ethyl (2E,6R)-6,7-isopropylidenedioxy hept-2-enoate 24 (13.87 g, 60.8 mmol) in dry CH$_2$Cl$_2$ (60 ml) was cooled to −20° C. (CCl$_4$+dry ice bath) and treated with a solution of DIBAL-H (17.27 g, 121.6 g, mmol; 2.5M solution in hexane) drop wise. After stirring for 2 h, the reaction mixture was warmed to 0° C., treated drop wise with MeOH (10 mL) to obtain a gelatin cake. The mixture was diluted with CH$_2$Cl$_2$ (100 mL) and stirred for 15 min. A solution of Na-K tartarate (90 mL) was added drop wise and stirred for an additional 45 min. Reaction mixture was filtered through celite and washed with CH$_2$Cl$_2$ (2×50 mL). The organic layer was washed with water (2×100 mL), brine (50 mL), dried (Na$_2$SO$_4$) and evaporated to give (2E,6R)-6,7-isopropylidenedioxy hept-2-ene-1-ol 25 (11 g) in 98.2% yield as a colorless liquid. [α]$_D$−13.2 (c 2.5, CHCl$_3$); $^1$HNMR (CDCl$_3$, 200 MHz): δ 1.16,1.2 (2s, 6H, CH$_3$), 1.46–1.74 (m, 2H, H-5), 1.79–198 (m, 1H, —OH), 2.02–2.19 (m, 2H, H-4), 3.36–3.78(m, 3H, H-6,7), 4.02–4.12 (m, 2H, H-1), 5.61–5.71 (m, 2H, H-2,3); $^{13}$CNMR (CDCl$_3$, 50 MHz): δ 25.3, 26.5, 28.0, 32.7, 62.8, 68.9, 75.1, 108.3, 129.8 (2C); EIMS m/z (relative intensity): 171 (M$^+$−15, 35.8), 93 (22.3), 67 (37.3), 55 (26.8), 43 (100); HRMS: Calculated for C9H15O3 (M$^+$−15): 171.102120; observed: 171.102195.

Part 7: (2R,3R,6R)-2,3-Epoxy-6,7-isopropylidenedioxy heptan-1-ol (Scheme XV; 26)

To a stirred and cooled (−20° C.) suspension of molecular sieves (4 A, 1.25 g) in CH$_2$Cl$_2$ (10 mL) under N$_2$ atmosphere, (−)-diisopropyl D-tartarate (7.6 g, 32.4 mmol), titanium(IV) isopropoxide (7.68 g, 27.02 mmol) and cumene hydroperoxide (8.22 g, 54 mmol) were added sequentially. After 20 min., the resulting mixture was treated drop wise addition of a solution of (2E,6R)-6,7-isopropylidenedioxy hept-2-ene-1-ol 25 (5 g, 26.88 mmol) in CH$_2$Cl$_2$ (15 mL) and stirred for additional 3 h. The reaction mixture was quenched with 10% NaOH solution saturated with NaCl (15 mL) and filtered through celite. Evaporation of solvent and purification of residue by column chromatography (Si-gel, 1:1 EtOAc-hexane) gave (2R,3R,6R)-2,3-epoxy-6,7-isopropylidenedioxy heptan-1-ol 26 (4.15 g) in 76.4% yield as a colorless liquid. [α]$_D$+24.3(c 0.3, CHCl$_3$); $^1$HNMR (CDCl$_3$, 200 MHz): δ 1.32, 1.38 (2s, 6H, CH$_3$), 1.58–1.78 (m, 4H, H-4,5), 2.84–3.01 (m, 2H, H-2,3), 3.5 (t, 1H, J 6.1 Hz, H-7), 3.6 (dd, 1H, J 4.7, 11.75 Hz, H-1), 3.85 (dd, 1H, J 3.29, 11.75, H-1a), 3.98–4.2 (m, 2H, H-6,7'); $^{13}$CNMR (CDCl$_3$, 50 MHz): δ 25.5, 26.8, 27.6, 29.6, 55.3, 58.3, 61.6, 69.1, 75.1, 108.8; EIMS M/Z (relative intensity): 188 (M$^+$−15, 14.9), 144 (85), 101(47.7), 83 (95), 43 (100); HRMS: Calculated for C$_9$H$_{15}$O$_4$ (M−15): 187.097034; Observed: 187.096634.

Part 8: (2R,3R,6R)-1-Chloro-2,3-epoxy-6,7-isopropylidenedioxy heptane (Scheme XV; 27)

A stirred mixture of (2R,3R,6R)-2,3-epoxy-6,7-isopropylidenedioxy heptan-1-ol 26 (3.8 g, 18.8 mmol), Ph$_3$P (7.4 g, 28.3 mmol) and NaHCO$_3$ (0.6 g) in CCl$_4$ (50 mL) was heated at reflux for 3 h. The solvent was evaporated and residue obtained purified by column chromatography (Si-gel, 20% EtOAc-hexane) to give (2R,3R,6R)-1-chloro-2,3-epoxy-6,7-isopropylidenedioxy heptane 27 (2.8 g) in 67.8% yield as a colorless liquid. [α]$_D$+8.16(c 0.7, CHCl$_3$); $^1$HNMR (CDCl$_3$, 200 MHz): δ 1.31, 1.36 (2s, 6H, CH$_3$), 1.63–1.72 (m, 4H, H-4,5), 2.8–2.9 (m, 1H, H-2), 2.91–3.02 (m, 1H, H-3), 3.32–3.68 (m, 3H, H-1,7), 3,95–4.19 (m, 2H, H-6,7a); $^{13}$CNMR (CDCl$_3$, 50 MHz): δ 25.6, 26.9, 27.6, 29.6, 44.5, 57.0, 58.3, 69.2, 75.1, 108.9; EIMS m/z (relative intensity): 205 (M$^+$−15, 35.8), 145 (23), 83 (61), 72 (98), 43 (100); HRMS: Calculated for C$_9$H$_{14}$ClO$_3$ (M$^+$−15): 205.063147; Observed: 205.062719.

Part 9: (3R,6R)-3-Hydroxy-6,7-isopropylidenedioxy-hept-1-yne (Scheme XV; 28)

To freshly prepared LDA [prepared from diisopropyl amine (4.6 g, 45.45 mmol) and n-BuLi (2.91 g, 45.54 mmol; 1.4N hexane solution)] in THF (10 mL),a solution of (2R, 3R,6R)-1-chloro-2,3-epoxy-6,7-isopropylidenedioxy heptane 27 (2.5 g, 11.36 mmol) in THF (20 mL) was added at −40° C. (CH$_3$CN+dry ice bath). After 3 h, the reaction was quenched with aq. NH$_4$Cl solution and diluted with CH$_2$Cl$_2$ (50 mL). The organic layer was separated, washed with water (3×20 mL), brine (200 mL) and dried (Na$_2$SO$_4$), evaporated and residue purified by column chromatography (Si-gel, 15% EtOAc-hexane) to furnish (3R,6R)-3-hydroxy-6,7-isopropylidenedioxy-hept-1-yne 28 (2.0 g) in 95.2% yield as a pale yellow liquid. [α]$_D$−3.02(c 2.2, CHCl$_3$); $^1$HNMR (CDCl$_3$, 200 MHz): δ 1.32, 1.39 (2s, 6H, CH$_3$), 1.64–1.94 (m, 4H, H-4,5), 2.19–2.21 (br.s, 1H, OH), 2.39 (d, 1H, J 2.3 Hz, H-1), 3.5 (t, 1H, J 5.7 Hz, H-7), 3.96–4.16 (m, 2H, H-6,7a), 4.34–4.45 (m, 1H, H-3); $^{13}$CN (CDCl$_3$, 50 MHz): δ 25.4, 26.6, 28.8, 33.5, 61.3, 69.0, 72.7, 75.3, 84.7, 108.7; EIMS m/z (relative intensity): 169 (M$^+$−15, 22.3), 109 (20.8), 81 (37.3), 55 (35.8), 43 (100); HRMS: Calculated for C$_9$H$_{13}$O$_3$ (M−15): 169.086469; Observed: 169.086140.

Part 10: (3R,6R)-3-Acetoxy-6,7-isopropylidenedioxy-hept-1-yne (Scheme XV; 29)

A solution of hydroxy-6,7-isopropylidenedioxy-hept-1-yne 28 (1.8 g, 9.8 mmol) and pyridine (3.1 g, 39.2 mmol) in CH₂Cl₂ (15 mL) containing DMAP (catalytic) at 0° C. was treated with Ac₂O (1.2 g, 11.7 mmol) and stirred at room temperature for 30 min. After completion, the reaction was diluted with CH₂Cl₂ (50 mL), sequentially washed with CuSOi solution (3×20 mL), saturated aq. NaHCO₃ solution (20 mL), water (20 mL), brine (20 mL) and dried. Evaporation of solvent and purification of residue by column chromatography (Si-gel, 10% EtOAc-hexane) gave (3R, 6R)-3-acetoxy-6,7-isopropylidenedioxy-hept-1-yne 29 (2.15 g) in 97.2% yield as a yellow liquid. $[\alpha]_D$+37.5(c 2.1, CHCl₃); ¹HNMR (CDCl₃, 200 Mz): δ 1.3, 1.39 (2s, 6H, CH₃), 1.64–2.0 (m, 2H, H-4,5), 2.06 (s, 3H, CH₃), 2.4 (d, 1H, J 2.0 Hz, H-1), 3.5 (t, 1H, J 5.7 Hz, H-7), 3.95–4.13 (m, 2H, H-6,7a), 5.31–5.41 (m, 1H, H-3); ¹³CNMR (CDCl₃, 50 MHz): δ 20.8, 25.5, 26.8, 28.8, 30.7, 63.3, 69.1, 73.7, 75.1, 80.7, 108.9, 169.6; EIMS m/z (relative intensity): 211 (M⁺−15, 29.8), 169 (11.9), 91 (22.3), 72 (23), 43 (100); HRMS: Calculated for $C_{11}H_{15}O_4$ (M⁺−15): 211.097034; Observed; 211.095947.

Part 11: (3R,6R)-3-Acetoxy-6,7-dihydroxy-hept-1-yne (Scheme XV; 30)

A solution of (3R,6R)-3-acetoxy-6,7-isopropylidenedioxy-hept-1-yne 29 (2 g, 8.8 mmol) in MeOH (150 mL) containing catalytic amount of PTSA was stirred at 0° C. for 8 h. The reaction mixture was neutralised with saturated sat. NaHCO₃ solution, evaporated to remove MeOH and extracted with EtOAc (3×50 mL). Organic layer were evaporated and the residue filtered through a small pad of silica gel with 1:1 EtOAc-hexane to afford (3R,6R)-3-acetoxy-6,7-dihydroxy-hept-1-yne 30 (1.2 g) in 72.9% yield as a colorless syrup. $[\alpha]_D$+83.2 (c 1.2, CHCl₃); ¹HNMR (CDCl₃, 200 MHz): δ 1.5–1.7 (m, 2H, H-4), 1.75–2.05 (m, 2H, H-5), 2.14 (s, 3H, -OAc), 2.45 (d, 2H, H-1), 2.57 (br.s, 1H, OH), 3.35–3.5 (m, H, H-7), 3.57–3.8 (m, 2H, H-6,7a), 5.32–5.47 (m, 1H, H-3); CIMS m/z (relative intensity): 187 (M+1, 74.6), 127 (59.7), 109 (35.8), 81 (56.7), 43 (100); HRMS Calculated for $C_9H_{15}O_4$(M+1): 187.097034; Observed: 187.096547.

Part 12: (3R,6R)-3-Acetoxy-6-hydroxy-7-p-toluene sulfonyloxy-hept-1-yne (Scheme XV; 31)

A solution of (3R,6R)-3-acetoxy-6,7-dihydroxy-hept-1-yne 30 (1.1 g, 5.9 mmol) in CH₂Cl₂ (20 mL) containing pyridine (0.934 g, 11.82 mmol) was cooled to 0° C., treated with p-TsCl (1.12 g, 5.91 mmol) and stirred at room temperature for 8 h. The reaction mixture was diluted with CH₂Cl₂ and washed sequentially with water (20 mL), CuSO₄ solution (3×20 mL) and water (20 mL). Organic layer was dried (Na₂SO₄), evaporated and residue obtained was purified by column chromatography (Si-gel, 10% EtOAc-Hexane); first eluted was (3R,6R)-3-acetoxy-6,7-di-p-toluene sulfonyloxy-hept-1-yne 31a (0.23 g) in 8% yield as a yellow syrup. ¹HNMR (CDCl₃, 200 MHz): δ 1.5–1.85 (m, 4H, H-3,4), 2.05 (s, 3H, OAc), 2.41–2.52 (m, 7H, H-7, Ar—CH₃), 4.0 (d, 2H, J4.8 Hz, H-1), 4.58–4.62 (m, 1H, H-2), 5.12–5.26 (m,1H, H-5), 7.28–7.44, 7.64–7.81 (m, 4H each, Ar—H).

Second eluted was (³R,⁶R)-3-acetoxy-6-hydroxy-7-p-toluene sulfonyloxy-hept-1-yne 31 (1.1 g) in 55% yield as a yellow syrup. $[\alpha]_D$+28.1 (c 1.0, CHCl₃); ¹HNMR (CDCl₃, 200 MHz): δ 1.35–1.68 (m, 3H, H-4,—OH), 1.68–2.0 (m, 2H, H-5), 2.08 (s, 3H, CH₃), 2.4 (d, 1H, J 2.4 Hz, H-1), 2.46 (s, 3H, Ar—CH₃), 3.79–4.06 (m, 3H, H-6,7), 5.35 (td,1H, J4.8, 7.2 Hz, H-3), 7.36 (d, 2H, J 7.2 Hz, Ar—H), 7.8 (d, 2H, J 7.2 Hz, Ar—H). FABMS m/z (relative intensity): 341(M+1, 13.8), 281(50), 155(54.1), 133(52.7), 109(100). HRMS: Calculated for $C_{16}H_{21}O_6S$ (M+1):341.105885; Observed:341.104916.

Part 13: (2R,5R)-5-Ethynyl-2-(hydroxymethyl)-tetrahydrofuran (Scheme XV; 32)

To a solution of (3R,6R)-3-acetoxy-6-hydroxy-7-p-toluene sulfonyloxy-hept-1-yne 31 (0.6 g, 1.76 mmol) in MeOH (10 mL) at room temperature, K₂CO₃ (0.536 g, 3.88 mmol) was added and the mixture was stirred for 2 h. It was treated with NH₄Cl solution, evaporated MeOH and the residue extracted with EtOAc (3×20 mL). Organic layer was washed with water (10 mL), brine (10 mL), dried (Na₂SO₄) evaporated. The residue obtained was purified by column chromatography (Si-gel, 20% EtOAc-hexane) to furnish (2R,5R)-5-ethynyl-2-(hydroxymethyl)-tetrahydrofuran 32 (0.22 g) in 99% yield as a colorless liquid. $[\alpha]_D$+20.0 (c 1.0, CHCl₃); ¹HNMR (CDCl₃, 200 MHz): δ 1.89–2.38 (m, 4H, H-3,4), 2.4 (br.s, 1H, OH), 2.46 (d, 1H, J 2.2 Hz, H-7), 3.55 (dd, 1H, J 4.5, 11.25 Hz, H-1), 3.72 (dd, 1H, J 4.0, 11.25 Hz, H-1a), 4.0–4.15 (m, 1H, H-2), 4.52–4.66 (m,1H, H-5); ¹³CNMR (CDCl₃, 50 MHz): δ 26.6, 29.6, 33.6, 64.6, 68.3, 73.0, 80.7; EIMS m/z (relative intensity): 125 (M⁺−1, 8), 95 (74.6), 67 (100), 53 (40), 41 (80); HRMS: Calculated for $C_7H_9O_2$ (M−1): 125.060255; Observed: 125.060322.

Part 14: (2R,5R)-5-Ethynyl-2-(p-toluene sulfonyloxymethyl)-tetrahydrofuran (Scheme XV; 33)

A solution of alcohol (2R,5R)-5-ethynyl-2-(hydroxymethyl)-tetrahydrofuran 32 (0.22 g, 1.75 mmol) in pyridine (0.6 mL) was treated with p-TsCl (0.354 g, 1.86 mmol) and the mixture stirred at room temperature for 3 h. The reaction mixture was diluted with CH₂Cl₂ (20 mL) and washed sequentially with water (10 mL), CuSO₄ solution (2×10 mL), brine (10 mL) and dried (Na₂SO₄). Evaporation of solvent and purification of residue by column chromatography (Si-gel, 15% EtOAc-hexane) gave (2R,5R)-5-ethynyl-2-(p-toluene sulfonyloxymethyl)-tetrahydrofuran 33 (0.33 g) in 63.9% yield as a yellow syrup. $[\alpha]_D$+10.0 (c 0.54, CHCl₃); ¹HNMR (CDCl₃, 200 MHz): δ 1.84–2.11 (m, 4H, H-3,4) 2.32 (d, 1H, J 2.1 Hz, H-7), 2.45 (s, 3H, CH₃), 3.92–4.2 (m, 3H, H-2,1,1a), 4.48–4.58 (m, 1H, H-5), 7.34 (d, 2H, J 7.6 Hz, Ar—H), 7.8 (d, 2H, J 7.6 Hz, Ar—H); CIMS m/z (relative intensity): 281(M+1, 100), 109(49.2), 117(31.3), 81(7.0), 43(100); HRMS: Calculated for $C_{14}H_{17}O_4S$ (M+1):281.084756; Observed: 281.083610.

Part 15: (2R,5R)-5-Ethynyl-2-(4-fluoro phenoxymethyl)-tetrahydrofuran (Scheme XV; 34)

To a stirred suspension of NaH (0.032 g, 1.33 mmol) in DMF (3 mL), a solution of (2R,5R)-5-ethynyl-2-(p-toluene sulfonyloxy methyl)-tetrahydrofuran 33 (0.33 g, 1.1 mmol) in DMF (3 mL) was added and heated at 80° C. for 5 h. The reaction mixture was cooled to room temperature and treated with NH₄Cl solution. It was extracted with ether (2×10 mL) and the organic layer was washed with water (2×10 mL), brine (10 mL) and dried (Na₂SO₄). Evaporation of solvent and purification of residue by column chromatography (Si-gel, 7% EtOAc-hexane) afforded (2R,5R)-5-ethynyl-2-(4-fluoro phenoxy methyl)-tetrahydrofuran 34 (0.21 g) in 85.7% yield as a colorless liquid, whose spectral data is accordance with the reported reference values. $[\alpha]_D$+16.0 (c 1.0, CHCl₃); ¹HNMR (CDCl₃, 200 MHz): δ 1.88–2.32 (m, 4H, H-3,4), 2.41 (d, 1H, J 2.3 Hz, H-7), 3.9 (dd, 1H, J4.6, 9.1 Hz, H-1), 4.06 (dd, 1H, J 5.9, 9.1 Hz, H-1a), 4.22–4.36 (m, 1H, H-2), 4.58–4.69 (m, 1H, H-5), 6.75–7.02 (m, 4H, Ar—H); $^{13}$CNMR (CDCl$_3$, 50 MHz): δ 33.1, 68.5, 71.2, 72.9, 76.3, 83.7, 115.4, 115.6, 115.8, 115.9, 154.9, 159.6; EIMS m/z (relative intensity): 220 (M$^+$, 10.4), 125 (14.9), 95 (94), 67 (100), 41 (59.7); HRMS: Calculated for $C_{13}H_{13}O_2F$ (M$^+$): 220.089958; Observed: 220.089497.

EXAMPLE 12

Keto-epoxide Cyclisation

References in this Example 12 to compound numerals (generally underlined) designate the compounds depicted structurally in Scheme XVI above.

Part 1: Non-8-ene-1-p-methoxy phenyl methyl-5-oxo-3-yn-1-ol (Scheme XVI; 54)

A. Mixed anhydride (Scheme XVI; 53): A stirred and cooled (−10° C. to 0° C.) solution of pent-4-enoic acid (0.5 g, 5 mmol) and freshly distilled Et$_3$N (0.505 g, 5 mmol) in dry ether (5 mL), was treated with ethyl chloro formate (0.542 g, 5 mmol). The reaction mixture was allowed to reach room temperature and stirred for 3 h. The reaction mixture was filtered and washed with ether. Organic layer was washed with saturated NaHCO$_3$ solution (25 mL), water (25 mL), brine (20 mL) and dried (Na$_2$SO$_4$). Evaporation of solvent under vacuum at room temperature afforded mixed anhydride 53 (0.79 g) in 91.8% yield as a colorless syrup.

B. Non-8-ene-1-p-methoxy phenyl methyl-5-oxo-3-yn-1-ol (Scheme XVI; 54): A stirred solution of 1-p-methoxy phenyl methyl-but-3-yn-1-ol (52: 1.12 g, 5.91 mmol) in dry THF (5 mL) was cooled to −78° C. and treated with n-BuLi (4 mL, 5.91 mmol; 1.5 N hexane solution) dropwise. After 30 min., a solution of anhydride 53 (0.78 g, 4.54 mmol) in THF (5 mL) was added and stirred at the same temperature for 2 hours. The reaction mixture was quenched with aq. NH$_4$Cl solution (10 mL) and extracted with EtOAc (2×25 mL). Organic layer was washed with brine (25 mL), dried (Na$_2$SO$_4$), evaporated and purified the residue by column chromatography (Si-gel, 8:1 Hexane-EtOAc) to afford non-8-ene-1-p-methoxy phenyl methyl—5oxo-3-yn-1-ol (54; 0.35 g) in 27% yield as a colorless syrup. $^1$HNMR (CDCl$_3$, 200 MHz): δ 2.32–2.46 (m, 2H, H-7), 2.56–2.69 (m, 4H, H-6,2), 3.59 (t, 2H, J 8.37 Hz, H-1), 3.8 (s, 3H, -OMe), 4.47 (s, 2H, —OCH$_2$), 4.95–5.11 (m, 2H, H-9), 5.67–5.9 (m, 1H, H-8), 6.84, 7.22 (2d, 2H each, J 9.3 Hz, Ar—H).

Part 2: 1,2-Epoxy-9-p-methoxy phenyl methyl-5-oxon-non-6-yn-9-ol (Scheme XVI; 55)

A solution of non-8-ene-1-p-methoxy phenyl methyl-5-oxo-3-yn-1-ol 54 (0.2 g, 0.73 mmol) in acetone (5 mL) was sequentially treated with solid NaHCO$_3$ (0.306 g, 3.65 mmol), water (5 mL) followed by a solution of oxone (0.448 g, 073 mmol) in aqueous. 4×10$^{-4}$ M EDTA disodium solution (10 mL) dropwise at 0° C. and stirred at room temperature for 4 h. The reaction mixture was filtered and washed with EtOAc (10 mL). The aqueous layer was extracted with EtOAc (2×10 mL) and combined organic layers were washed with brine (20 mL) and dried (Na$_2$SO$_4$). Evaporation of solvent and purification of residue by column chromatography (Si-gel, 15% EtOAc in hexane) gave 1,2-epoxy-9-p-methoxy phenyl methyl—5-oxo-non-6-yn-9-ol 55 (0.1 g) in 48% yield as a colorless syrup. $^1$HNMR (CDCl$_3$, 200 MHz): δ 1.62–1.82 (m, 1H, H-3), 1.9–2.1 (m, 1H, H-3'),2.41–2.57 (m, 1 H, H-1), 2.57–2.74 (m, 5H, H-1',4,8), 2.85–2.96 (m, 1H, H-2), 3.58 (t, 2H, J 8.13 Hz, H-9), 3.8 (s, 3H, —OMe), 4.45 (s, 2H, —OCH$_2$), 6.84, 7.22 (2d, 2H each, J 9.3 Hz, Ar—H).

Part 3: (2S,5RS)-2-(Hydroxymethyl)-5-(1-p-methoxyphenyhnethylenoxy-but-3-yn-4-yl)-tetrahydrofuran (Scheme XVI; 56)

To a stirred and cooled −78° C. solution of 1,2-epoxy-9-p-methoxy phenyl methyl—5-oxo-non-6-yn-9-ol 55 (0.075 g. 0.26 mmol) in CH$_2$Cl$_2$ (52 mL; 0.005M solution), a solution of BH$_3$-DMS (0.25 mL, 0.26 mmol; 1 M solution in CH$_2$Cl$_2$) was added dropwise. After 3 hours, the reaction mixture was quenched with aq. NH$_4$Cl solution (10 mL) at 0° C. and extracted with EtOAc (2×10 mL). Organic layer was washed with water (2×10 mL), brine (10 mL) and dried (Na$_2$SO$_4$). Evaporation of solvent and purification of residue by column chromatography (Si-gel, 25% EtOAc in hexane) gave racemic 2-(Hydroxymethyl)5-(1-p-methoxyphenyhnethylenoxy-but-3-yn- 4-yl)-tetrahydrofuran 56 (0.025 g) in 34% yield as a colorless syrup. The compound 56 thus obtained by this approach is comparable to compound 39 (Scheme IX) by TLC analysis as well as $^1$HNMR data.

EXAMPLE 13

Di-hydroxy Compound

References in this Example 13 to compound numerals (generally underlined) designate the compounds depicted structurally in Scheme XVII above.

Mannose diacetonide 70 is converted to the corresponding sulfide 72 on reaction a 10 with diphenyl sulfide and tributyl phosphone in dichloromethane. The 5,6-acetonide group of the reaction product is hydrolyzed with 60% aqueous acetic acid to afford the diol, which on cleavage with sodium periodate gives the aldehyde. Reaction of the aldehyde with sodium borohydride gives the alcohol 73 which on reaction with tosyl chloride gives the tosylate. Reaction of the tosylate with the sodium salt of p-fluorophenol in dimethyl formamide gives the aryl ether 74. The sulfide is oxidized with oxone to sulfone. The resulting sulfone on further reaction with magneium acetylide of 4-OPM-but-1-yn-4-ol (prepared from ethyl magnesium bromide and homoproargyl alcohol MPM ether) in the presence of zinc bromide gives the acetylene 75. The acetylene compound is reacted with DDQ to give the alcohol, which in turn on reaction with N-hydroxy urea derivative and further reaction with ammonia provides compound 76.

EXAMPLE 14

Human Whole Blood Assay

The following compound of the invention was tested for Leukotriene $B_4$ inhibition in the human whole blood assay detailed below.

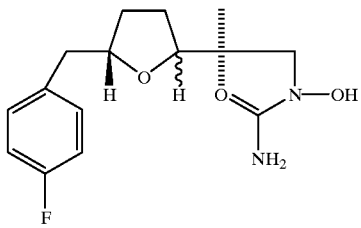

Heparinized human whole blood was pre-incubated with selected concentrations of the test compound for 15 minutes at 37° C. and stimulated with 50 µM calcium ionphor for 30 minutes at 37° C. The reaction was stopped by placing samples on ice and cold centrifugation at 4° C. for 10 minutes at 1100×g. Test sample plasma was diluted in buffer and assayed for $LTB_4$ content. Test compound activity was determined as per Cayman LTD EIA and evaluated as $IC_{50}$ [nM]. The compound had an $IC_{50}$ of 148 nM. Other tested stereoisomers of the above compound exhibited differing $IC_{50}$ values.

The invention has been described in detail including preferred embodiments thereof. However, it will be understood that those skilled in the art, upon consideration of this disclosure, may make modifications and improvements thereon without departing from the spirit and scope of the invention as set forth in the following claims.

What is claimed is:

1. A compound of the following Formula I:

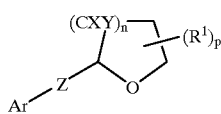

wherein Ar is optionally substituted aryl or optionally substituted heteroaryl;

each $R^1$, X and Y is independently hydrogen or a non-hydrogen substituent;

Z is a chemical bond, optionally substituted alkylene, optionally substituted alkenylene, optionally substituted alkynylene, optionally substituted heteroalkylene, optionally substituted heteroalkenylene, optionally substituted heteroalkenylene, or a hetero atom;

n is an integer from 2 to 11;

p is an integer from 0 to 4; and pharmaceutically acceptable salts thereof.

2. A compound of the following Formula III:

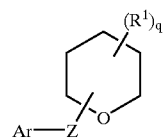

wherein Ar is optionally substituted carbocyclic aryl or optionally substituted heteroaryl;

Z is a chemical bond, optionally substituted alkylene, optionally substituted alkenylene, optionally substituted alkynylene, optionally substituted heteroalkylene, optionally substituted heteroalkenylene, optionally substituted heteroalkylene, or a hetero atom;

each $R^1$ is independently hydrogen or a non-hydrogen substituent;

q is an integer of from 0 to 9; and pharmaceutically salts thereof.

3. A compound of the following Formula IV:

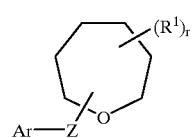

wherein Ar is optionally substituted carbocyclic aryl or optionally substituted heteroaryl;

Z is a chemical bond, optionally substituted alkylene, optionally substituted alkenylene, optionally substituted alkynylene, optionally substituted heteroalkylene, optionally substituted heteroalkenylene, optionally substituted heteroalkylene, or a hetero atom;

each $R^1$ is independently hydrogen or a non-hydrogen substituent;

r is an integer of from 0 to 11; and pharmaceutically acceptable salts thereof.

4. A compound of the following Formula V:

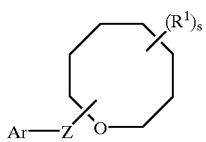

wherein Ar is optionally substituted carbocyclic aryl or optionally substituted heteroaryl;

Z is a chemical bond, optionally substituted alkylene, optionally substituted alkenylene, optionally substituted alkynylene, optionally substituted heteroalkylene, optionally substituted heteroalkenylene, optionally substituted heteroalkylene, or a hetero atom;

each $R^1$ is independently hydrogen or a non-hydrogen substituent;

s is an integer of from 0 to 9; and pharmaceutically salts thereof.

5. A compound of any one of claims 1–4 wherein at least one $R^1$ group is hydroxy or alkoxy.

6. A compound of any one claims 1–4 wherein at least two $R^1$ groups is hydroxy or alkoxy.

7. A compound of any one claims 1–4 wherein two $R^1$ are present as hydroxy groups on adjacent ring positions.

8. A compound of any one claims 1–4 wherein two $R^1$ are present as alkoxy groups on adjacent ring positions.

9. A pharmaceutical composition comprising a compound of claim 1 and a pharmaceutically acceptable carrier.

10. A method of treating a disorder or disease associated with 5-lipoxygenase, comprising administering to a subject suffering from or susceptible to such a disease or disorder an effective amount of a compound or composition of any one of claims 1–4.

11. A method of treating an immune, allergic or cardiovascular disorder or disease, comprising administering to a subject suffering from or susceptible to such a disease or disorder an effective amount of a compound or composition of any one of claims 1–4.

12. A method of treating a disorder or disease associated with 5-lipoxygenase, comprising administering to a subject suffering from or susceptible to such a disease or disorder an effective amount of a compound or composition of claim 5.

13. A method of treating an immune, allergic or cardiovascular disorder or disease, comprising administering to a subject suffering from or susceptible to such a disease or disorder an effective amount of a compound or composition of claim 5.

14. A method of treating a disorder or disease associated with 5-lipoxygenase, comprising administering to a subject suffering from or susceptible to such a disease or disorder an effective amount of a compound or composition of claim 6.

15. A method of treating an immune, allergic or cardiovascular disorder or disease, comprising administering to a subject suffering from or susceptible to such a disease or disorder an effective amount of a compound or composition of claim 6.

16. A method of treating a disorder or disease associated with 5-lipoxygenase, comprising administering to a subject suffering from or susceptible to such a disease or disorder an effective amount of a compound or composition of claim 7.

17. A method of treating an immune, allergic or cardiovascular disorder or disease, comprising administering to a subject suffering from or susceptible to such a disease or disorder an effective amount of a compound or composition of claim 7.

18. A method of treating a disorder or disease associated with 5-lipoxygenase, comprising administering to a subject suffering from or susceptible to such a disease or disorder an effective amount of a compound or composition of claim 8.

19. A method of treating an immune, allergic or cardiovascular disorder or disease, comprising administering to a subject suffering from or susceptible to such a disease or disorder an effective amount of a compound or composition of claim 8.

20. A compound of claim 2 wherein the compound is of the following Formula IIIa:

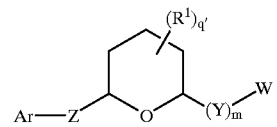

IIIa wherein in Formula IIIa, Ar is optionally substituted carbocyclic aryl or optionally substituted heteroaryl;

W is —AN(OM)C(O)N($R^3$)$R^4$, —N(OM)C(O)N($R^3$)$R^4$, —AN($R^3$)C(O)N(OM)$R^4$, —N($R^3$)C(O)N(OM)$R^4$, —AN(OM)C(O)$R^4$, —N(OM)C(O)$R^4$, —AC(O)N(OM)$R^4$, —C(O)N(OM)$R^4$, or —C(O)NHA; and A is lower alkyl, lower alkenyl, lower alkynyl, alkylaryl or arylalkyl, wherein one or more carbons optionally can be replaced by N, O or S, however —Y—A—, —A—, or —AW— should not include two adjacent heteroatoms;

Y is O, S, S(O), S(O)$_2$, N$R^3$ or CH$R^5$; m is 0 or 1;

Z is a chemical bond, optionally substituted alkylene, optionally substituted alkenylene, optionally substituted alkynylene, optionally substituted heteroalkylene, optionally substituted alkenylene, optionally substituted heteroalkylene, optionally substituted heteroalkenylene, optionally substituted heteroalkenylene, or a hetero atom;

$R^3$ and $R^4$ are independently hydrogen, alkyl, alkenyl, alkynyl, aryl, arylalkyl, $C_{1-6}$alkoxy-$C_{1-10}$alkyl, $C_{1-6}$alkylthio-$C_{1-10}$ alkyl, heteroaryl, or heteroarylalkyl;

$R^5$ is hydrogen, lower alkyl, lower alkenyl, lower alkynyl, arylalkyl, alkaryl, —AN(OM)C(O)N($R^3$)$R^4$, —AN($R^3$)C(O)N(OM)$R^4$, —AN(OM)C(O)$R^4$, —AC(O)N(OM)$R^4$, —AS(O)$_x$$R^3$, —AS(O)$_x$CH$_2$C(O)$R^3$, —AS(O)$_x$CH$_2$CH(OH)$R^3$, or —AC(O)NH$R^3$, wherein x is 0–2; s is an integer of from 0 to 10; q' is an integer of from 0 to 6; and pharmaceutically acceptable salts thereof.

21. A pharmaceutical composition comprising a compound of claim 20 and a pharmaceutically acceptable carrier.

22. A compound of claim 3 wherein the compound is of the following Formula IVa:

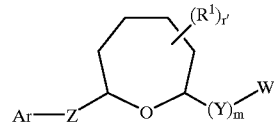

IVa wherein in Formula IVa, Ar is optionally substituted carbocyclic aryl or optionally substituted heteroaryl;

W is —AN(OM)C(O)N($R^3$)$R^4$, —N(OM)C(O)N($R^3$)$R^4$, —AN($R^3$)C(O)N(OM)$R^4$, —N($R^3$)C(O)N(OM)$R^4$, —AN(OM)C(O)$R^4$, —N(OM)C(O)$R^4$, —AC(O)N(OM)$R^4$, —C(O)N(OM)$R^4$, or —C(O)NHA; and A is lower alkyl, lower alkenyl, lower alkenyl, alkylaryl or arylalkyl, wherein one or more carbons optionally can be replaced by N, O or S, however —Y—A—, —A—, or —AW— should not include two adjacent heteroatoms;

Y is O, S, S(O), S(O)$_2$, N$R^3$ or CH$R^5$; m is 0 or 1;

Z is a chemical bond, optionally substituted alkylene, optionally substituted alkenylene, optionally substituted alkynylene, optionally substituted heteroalkylene, optionally substituted alkenylene, optionally substituted heteroalkylene, optionally substituted heteroalkenylene, optionally substituted heteroalkynylene, or a hetero atom;

$R^3$ and $R^4$ are independently hydrogen, alkyl, alkenyl, alkynyl, aryl, arylalkyl, $C_{1-6}$alkoxy-$C_{1-10}$alkyl, $C_{1-6}$ alkylthio-$C_{1-10}$ alkyl, heteroaryl, or heteroarylalkyl;

$R^5$ is hydrogen, lower alkyl, lower alkenyl, lower alkynyl, arylalkyl, alkaryl, —AN(OM)C(O)N($R^3$)$R^4$, —AN($R^3$)C(O)N(OM)$R^4$, —AN(OM)C(O)$R^4$, —AC(O)N(OM)$R^4$, —AS(O)$_x$$R^3$, —AS(O)$_x$CH$_2$C(O)$R^3$, —AS(O)$_x$CH$_2$CH(OH)$R^3$, or —AC(O)NH$R^3$, wherein x is 0–2; s is an integer of from 0 to 10; r' is an integer of from 0 to 4; and pharmaceutically acceptable salts thereof.

23. A pharmaceutical composition comprising a compound of claim 22 and a pharmaceutically acceptable carrier.

24. A compound of claim 4 wherein the compound is of the following Formula Va:

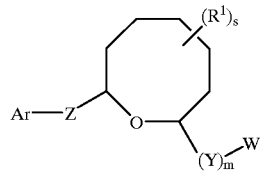

Va wherein in Formula Va, Ar is optionally substituted aryl or optionally heteroaryl;

W is —AN(OM)C(O)N($R^3$)$R^4$, —N(OM)C(O)N($R^3$)$R^4$, —AN($R^3$)C(O)N(OM)$R^4$, —N($R^3$)C(O)N(OM)$R^4$, —AN(OM)C(O)$R^4$, —N(OM)C(O)$R^4$, —AC(O)N(OM)$R^4$, —C(O)N(OM)$R^4$, or —C(O)NHA; and A is lower alkyl, lower alkenyl, lower alkynyl, alkylaryl or arylalkyl, wherein one or more carbons optionally can be replaced by N, O or S, however —Y—A—, —A—, or —AW— should not include two adjacent heteroatoms;

Y is O, S, S(O), S(O)$_2$, NR$^3$ or CHR$^5$; m is 0 or 1;

Z is a chemical bond, optionally substituted alkylene, optionally substituted alkenylene, optionally substituted alkynylene, optionally substituted heteroalkylene, optionally substituted alkenylene, optionally substituted heteroalkylene, optionally substituted heteroalkenylene, optionally substituted heteroalkynylene, or a hetero atom;

$R^3$ and $R^4$ are independently hydrogen, alkyl, alkenyl, alkynyl, aryl, arylalkyl, $C_{1-6}$alkoxy-$C_{1-10}$alkyl, $C_{1-10}$ alkylthio-$C_{1-10}$ alkyl, heteroaryl, or heteroarylalkyl;

$R^5$ is hydrogen, lower alkyl, lower alkenyl, lower alkynyl, arylalkyl, alkaryl, —AN(OM)C(O)N($R^3$)$R^4$, —AN($R^3$)C(O)N(OM)$R^4$, —AN(OM)C(O)$R^4$, —AC(O)N(OM)$R^4$, —AS(O)$_x$$R^3$, —AS(O)$_x$CH$_2$C(O)$R^3$, —AS(O)$_x$CH$_2$CH(OH)$R^3$, or —AC(O)NH$R^3$, wherein x is 0–2; s is an integer of from 0 to 4; and pharmaceutically acceptable salts thereof.

25. A pharmaceutical composition comprising a compound of claim 24 and a pharmaceutically acceptable carrier.

26. A method of treating a disorder or disease associated with 5-lipoxygenase, comprising administering to a subject suffering from or susceptible to such a disease or disorder an effective amount of a compound or composition of any one of claims 20 through 25.

27. A method of treating an immune, allergic or cardiovascular disorder or disease, comprising administering to a subject suffering from or susceptible to such a disease or disorder an effective amount of a compound or composition of any one of claims 20 through 25.

28. A compound of claim 1 wherein n is 2, 3 or 4.

29. A compound of claim 1 wherein each $R^1$, X and Y is independently hydrogen, halogen, hydroxyl, optionally substituted alkyl, optionally substituted alkenyl, optionally substituted alkynyl, optionally substituted alkoxy, optionally substituted alkylthio, optionally substituted alkylsulfinyl, optionally substituted alkylsulfonyl, optionally substituted aminoalkyl, optionally substituted alkanoyl, optionally substituted carbocyclic aryl having at least about 6 ring carbons, or substituted or unsubstituted aralkyl having at least about 6 ring carbons.

30. A compound of claim 1 wherein Ar is optionally substituted carbocyclic aryl.

31. A compound of claim 1 wherein Ar is optionally substituted phenyl.

32. A compound of claim 1 wherein Ar is optionally substituted carbocyclic aryl.

33. A compound of claim 1 wherein Ar is optionally substituted pyrryl, furyl, pyridyl, 1,2,4-thiadiazolyl, pyrimidinyl, thienyl, isothiazolyl, imidazolyl, tetrazolyl, pyrazinyl, pyrimidyl, quinolyl, benzofuranyl, isoquinolinyl, benzothienyl, isobenzofuryl, pyrazolyl, indolyl, purinyl, carbazolyl, benzimidazolyl, or isoxazolyl.

34. The method of claim 10 wherein the subject is a mammal.

35. The method of claim 10 wherein the subject is a mammal.

36. A method for treating inflammation, hypertension, skeletal-muscular disorders, osteoarthritis, gout, asthma, lung edema, adult respiratory distress syndrome, pain, aggregation of platelets, shock, rheumatoid arthritis, psoriatic arthritis, psoriasis, autoimmune uveitis, allergic encephalomyelitis, systemic lupus erythematosis, acute necrotizing hemmorrhagic encephalopathy, idiopathic thrombocytopenia, polychondritis, chronic active hepatitis, idiopathic sprue, Crohn's disease, Graves ophthalmopathy, primary biliary cirrhosis, uveitis posterior, interstitial lung fibrosis, or asthma, comprising administering to the subject an effective amount of a compound or composition of any one of claims 1–9.

37. The method of claim 36 wherein the subject is a mammal.

38. A compound of claim 2 wherein the compound has a structure of Formula IIIa:

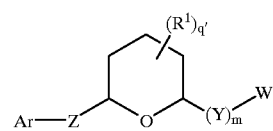

IIIa wherein Ar is optionally substituted aryl or optionally substituted heteroaryl;

Z is a chemical bond, optionally substituted alkylene, optionally substituted alkenylene, optionally substituted alkynylene, optionally substituted heteroalkylene, optionally substituted heteroalkenylene, optionally substituted heteroalkynylene, or a hetero atom;

each $R^1$ is independently hydrogen or a non-hydrogen substituent;

m is 0 or 1

W is —AN(OM)C(O)N($R^3$)$R^4$, —N(OM)C(O)N($R^3$)$R^4$, —AN(R)C(O)N(OM)$R^4$, —N($R^3$)C(O)N(OM)$R^4$, —AN(OM)C(O)$R^4$, —N(OM)C(O)$R^4$, —AC(O)N(OM)$R^4$, —C(O)N(OM)$R^4$, or —C(O)NHA; and A is lower alkyl, lower alkenyl, lower alkynyl, alkylaryl or arylalkyl, wherein one or more carbons optionally can be replaced by N, O or S, however —Y—A—, —A—, or —AW— should not include two adjacent heteroatoms;

M is hydrogen, a pharmaceutically acceptable cation or a metabolically cleavable leaving group;

Y is O, S, S(O), S(O)$_2$, $NR^3$ or $CHR^5$;

Z is O, S, S(O), S(O)$_2$, or $NR^3$;

$R^3$ and $R^4$ are independently hydrogen, alkyl, alkenyl, alkynyl, aryl, arylalkyl, $C_{1-6}$alkoxy-$C_{1-10}$alkyl, $C_{1-6}$alkylthio-$C_{1-10}$ alkyl, heteroaryl, or heteroarylalkyl;

$R^5$ is hydrogen, lower alkyl, lower alkenyl, lower alkynyl, arylalkyl, alkaryl, —AN(OM)C(O)N($R^3$)$R^4$, —AN($R^3$)C(O)N(OM)$R^4$, —AN(OM)C(O)$R^4$, —AC(O)N(OM)$R^4$, —AS(O)$_x$$R^3$, —AS(O)$_x$CH$_2$C(O)$R^3$, —AS(O)$_x$CH$_2$CH(OH)$R^3$, or —AC(O)NH$R^3$, wherein x is 0–2;

and pharmaceutically acceptable of such compounds.

39. A compound of claim 38 wherein q' is an integer of from 0 to 4.

40. A compound of claim 38 wherein at least one $R^1$ group is hydroxy or alkoxy.

41. A compound of claim 38 wherein at least two $R^1$ groups are hydroxy or alkoxy.

42. A compound of claim 38 wherein two $R^1$ groups are present as hydroxy groups on adjacent ring positions.

43. A compound of claim 38 wherein two $R^1$ groups are present as alkoxy groups on adjacent ring positions.

44. A compound of claim 38 wherein Ar is optionally substituted carbocyclic aryl.

45. A compound of claim 38 wherein Ar is optionally substituted phenyl.

46. A compound of claim 38 wherein Ar is optionally substituted heteroaryl.

47. A compound of claim 38 wherein Ar is is optionally substituted pyrryl, furyl, pyridyl, 1,2,4-thiadiazolyl, pyrimidinyl, thienyl, isothiazolyl, imidazolyl, tetrazolyl, pyrazinyl, pyrimidyl, quinolyl, benzofuranyl, isoquinolinyl, benzothienyl, isobenzofuryl, pyrazolyl, indolyl, purinyl, carbazolyl, benzimidazolyl, or isoxazolyl.

48. A pharmaceutical composition comprising a compound of claim 38 and a pharmaceutically acceptable carrier.

49. A compound of claim 3 wherein the compound has a structure of Formula IVa:

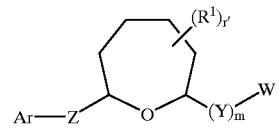

IVa wherein Ar is optionally substituted aryl or optionally substituted heteroaryl;

Z is a chemical bond, optionally substituted alkylene, optionally substituted alkenylene, optionally substituted alkynylene, optionally substituted heteroalkylene, optionally substituted heteroalkenylene, optionally substituted heteroalkynylene, or a hetero atom;

each $R^1$ is independently hydrogen or a non-hydrogen substituent;

m is 0 or 1

W is —AN(OM)C(O)N($R^3$)$R^4$, —N(OM)C(O)N($R^3$)$R^4$, —AN($R^3$)C(O)N(OM)$R^4$, —N($R^3$)C(O)N(OM)$R^4$, —AN(OM)C(O)$R^4$, —N(OM)C(O)$R^4$, —AC(O)N(OM)$R^4$, —C(O)N(OM)$R^4$, or —C(O)NHA; and A is lower alkyl, lower alkenyl, lower alkynyl, alkylaryl or arylalkyl, wherein one or more carbons optionally can be replaced by N, O or S, however —Y—A—, —A—, or —AW— should not include two adjacent heteroatoms;

M is hydrogen, a pharmaceutically acceptable cation or a metabolically cleavable leaving group;

Y is O, S, S(O), S(O)$_2$, $NR^3$ or $CHR^5$;

Z is O, S, S(O), S(O)$_2$, or $NR^3$;

$R^3$ and $R^4$ are independently hydrogen, alkyl, alkenyl, alkynyl, aryl, arylalkyl, $C_{1-6}$alkoxy-$C_{1-10}$alkyl, $C_{1-6}$alkylthio-$C_{1-10}$ alkyl, heteroaryl, or heteroarylalkyl;

$R^5$ is hydrogen, lower alkyl, lower alkenyl, lower alkynyl, arylalkyl, alkaryl, —AN(OM)C(O)N($R^3$)$R^4$, —AN($R^3$)C(O)N(OM)$R^4$, —AN(OM)C(O)$R^4$, —AC(O)N(OM)$R^4$, —AS(O)$_x$$R^3$, —AS(O)$_x$CH$_2$C(O)$R^3$, —AS(O)$_x$CH$_2$CH(OH)$R^3$, or —AC(O)NH$R^3$, wherein x is 0–2;

and pharmaceutically acceptable of such compounds.

50. A compound of claim 49 wherein r' is an integer of from 0 to 4.

51. A compound of claim 49 wherein at least one $R^1$ group is hydroxy or alkoxy.

52. A compound of claim 49 wherein at least two $R^1$ groups are hydroxy or alkoxy.

53. A compound of claim 49 wherein two $R^1$ groups are present as hydroxy groups on adjacent ring positions.

54. A compound of claim 49 wherein two $R^1$ groups are present as alkoxy groups on adjacent ring positions.

55. A compound of claim 49 wherein Ar is optionally substituted carbocyclic aryl.

56. A compound of claim 49 wherein Ar is optionally substituted phenyl.

57. A compound of claim 49 wherein Ar is optionally substituted heteroaryl.

58. A compound of claim 49 wherein Ar is is optionally substituted pyrryl, furyl, pyridyl, 1,2,4-thiadiazolyl, pyrimidinyl, thienyl, isothiazolyl, imidazolyl, tetrazolyl, pyrazinyl, pyrimidyl, quinolyl, benzofuranyl, isoquinolinyl, benzothienyl, isobenzofuryl, pyrazolyl, indolyl, purinyl, carbazolyl, benzimidazolyl, or isoxazolyl.

59. A pharmaceutical composition comprising a compound of claim 49 and a pharmaceutically acceptable carrier.

60. A compound of claim 4 wherein the compound has a structure of Formula Va:

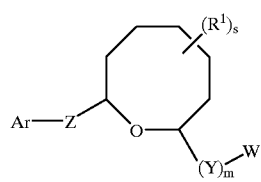

Va wherein Ar is optionally substituted aryl or optionally substituted heteroaryl;
Z is a chemical bond, optionally substituted alkylene, optionally substituted alkenylene, optionally substituted alkynylene, optionally substituted heteroalkylene, optionally substituted heteroalkenylene, optionally substituted heteroalkynylene, or a hetero atom;
each $R^1$ is independently hydrogen or a non-hydrogen substituent;
m is 0 or 1
W is —AN(OM)C(O)N($R^3$)$R^4$, —N(OM)C(O)N($R^3$)$R^4$, —AN($R^3$)C(O)N(OM)$R^4$, —N($R^3$)C(O)N(OM)$R^4$, —AN(OM)C(O)$R^4$, —N(OM)C(O)$R^4$, —AC(O)N(OM)$R^4$, —C(O)N(OM)$R^4$, or —C(O)NHA; and A is lower alkyl, lower alkenyl, lower alkynyl, alkylaryl or arylalkyl, wherein one or more carbons optionally can be replaced by N, O or S, however —Y—A—, —A—, or —AW— should not include two adjacent heteroatoms;
M is hydrogen, a pharmaceutically acceptable cation or a metabolically cleavable leaving group;
Y is O, S, S(O), S(O)$_2$, NR$^3$ or CHR$^5$;
Z is O, S, S(O), S(O)$_2$, or NR$^3$;
$R^3$ and $R^4$ are independently hydrogen, alkyl, alkenyl, alkynyl, aryl, arylalkyl, $C_{1-6}$alkoxy-$C_{1-10}$alkyl, $C_{1-6}$ alkylthio-$C_{1-10}$ alkyl, heteroaryl, or heteroarylalkyl;
$R^5$ is hydrogen, lower alkyl, lower alkenyl, lower alkynyl, arylalkyl, alkaryl, —AN(OM)C(O)N($R^3$)$R^4$, —AN($R^3$)C(O)N(OM)$R^4$, —AN(OM)C(O)$R^4$, —AC(O)N(OM)$R^4$, —AS(O)$_x$$R^3$, —AS(O)$_x$CH$_2$C(O)$R^3$, —AS(O)$_x$CH$_2$CH(OH)$R^3$, or —AC(O)NHR$^3$, wherein x is 0–2;
and pharmaceutically acceptable of such compounds.

61. A compound of claim 60 wherein q' is an integer of from O to 4.

62. A compound of claim 60 wherein at least one $R^1$ group is hydroxy or alkoxy.

63. A compound of claim 60 wherein at least two $R^1$ groups are hydroxy or alkoxy.

64. A compound of claim 60 wherein two $R^1$ groups are present as hydroxy groups on adjacent ring positions.

65. A compound of claim 60 wherein two $R^1$ groups are present as alkoxy groups on adjacent ring positions.

66. A compound of claim 60 wherein Ar is optionally substituted carbocyclic aryl.

67. A compound of claim 60 wherein Ar is optionally substituted phenyl.

68. A compound of claim 60 wherein Ar is optionally substituted heteroaryl.

69. A compound of claim 60 wherein Ar is is optionally substituted pyrryl, furyl, pyridyl, 1,2,4-thiadiazolyl, pyrimidinyl, thienyl, isothiazolyl, imidazolyl, tetrazolyl, pyrazinyl, pyrimidyl, quinolyl, benzofuranyl, isoquinolinyl, benzothienyl, isobenzofuryl, pyrazolyl, indolyl, purinyl, carbazolyl, benzimidazolyl, or isoxazolyl.

70. A pharmaceutical composition comprising a compound of claim 60 and a pharmaceutically acceptable carrier.

71. A method of treating a disorder or disease associated with 5-lipoxygenase, comprising administering to a subject suffering from or susceptible to such a disease or disorder an effective amount of a compound or composition of any one of claims 38 through 70.

72. A method of treating an immune, allergic or cardiovascular disorder or disease, comprising administering to a subject suffering from or susceptible to such a disease or disorder an effective amount of a compound or composition of any one of claims 38 through 70.

73. A method for treating inflammation, hypertension, skeletal-muscular disorders, osteoarthritis, gout, asthma, lung edema, adult respiratory distress syndrome, pain, aggregation of platelets, shock, rheumatoid arthritis, psoriatic arthritis, psoriasis, autoimmune uveitis, allergic encephalomyelitis, systemic lupus erythematosis, acute necrotizing hemmorrhagic encephalopathy, idiopathic thrombocytopenia, polychondritis, chronic active hepatitis, idiopathic sprue, Crohn's disease, Graves ophthalmopathy, primary biliary cirrhosis, uveitis posterior, interstitial lung fibrosis, or asthma, comprising administering to the subject an effective amount of a compound or composition of any one of claims 38 through 70.

74. A method of claim 71 wherein the subject is a mammal.

75. A method of claim 72 wherein the subject is a mammal.

76. A method of claim 73 wherein the subject is a mammal kel catalyst.

* * * * *